(12) United States Patent
Gjerde

(10) Patent No.: US 9,920,294 B2
(45) Date of Patent: Mar. 20, 2018

(54) DEVICES AND METHODS FOR PURIFICATION, DETECTION AND USE OF BIOLOGICAL CELLS

(71) Applicant: Douglas T. Gjerde, Saratoga, CA (US)

(72) Inventor: Douglas T. Gjerde, Saratoga, CA (US)

(73) Assignee: Douglas T. Gjerde, Saratoga, CA (US)

( * ) Notice: Subject to any disclaimer, the term of this patent is extended or adjusted under 35 U.S.C. 154(b) by 0 days.

(21) Appl. No.: 14/806,571

(22) Filed: Jul. 22, 2015

(65) Prior Publication Data

US 2016/0017272 A1    Jan. 21, 2016

Related U.S. Application Data

(63) Continuation-in-part of application No. PCT/US2015/024374, filed on Apr. 3, 2015, and a continuation-in-part of application No. 14/563,994, filed on Dec. 8, 2014, now Pat. No. 9,637,719, and a continuation-in-part of application No. PCT/US2014/016637, filed on Feb. 15, 2014.

(60) Provisional application No. 62/061,636, filed on Oct. 8, 2014, provisional application No. 61/974,950, filed on Apr. 3, 2014, provisional application No. 61/913,190, filed on Dec. 6, 2013, provisional application No. 61/765,541, filed on Feb. 15, 2013, (Continued)

(51) Int. Cl.
| | | |
|---|---|---|
| *C12M 1/00* | (2006.01) | |
| *C12N 1/02* | (2006.01) | |
| *C12N 5/00* | (2006.01) | |
| *C12N 5/076* | (2010.01) | |
| *C12N 5/0789* | (2010.01) | |
| *C12N 5/09* | (2010.01) | |

(52) U.S. Cl.
CPC ............... *C12M 47/02* (2013.01); *C12N 1/02* (2013.01); *C12N 5/0081* (2013.01); *C12N 5/061* (2013.01); *C12N 5/0647* (2013.01); *C12N 5/0693* (2013.01)

(58) Field of Classification Search
None
See application file for complete search history.

(56) References Cited

U.S. PATENT DOCUMENTS

| | | | |
|---|---|---|---|
| 5,225,353 A | | 7/1993 | Berenson et al. |
| 5,773,224 A | * | 6/1998 | Grandics .......... G01N 33/56966 435/7.1 |

(Continued)

OTHER PUBLICATIONS

Zeng, Cheng-Ming; et al; "Immobilization of human red cells in gel particles for chromatographic activity studies of the glucose transporter Glut1" Biochimica et Biophysica Acta, 1325, 91-98, 1997.*

(Continued)

*Primary Examiner* — David W Berke-Schlessel
(74) *Attorney, Agent, or Firm* — Sue S. Kalman

(57) ABSTRACT

This invention relates to devices and methods for purifying, detecting and using biological cells. A variety of cell types including viable tumor, stem, immune and sperm cells can be purified from a complex biological sample using a column, including a pipette tip column. Methods of the invention can aid research, diagnosis and treatment of cancer. Purified viable cells can be detected on the column or eluted from the column and detected. Cells on a column can be used as a stationary phase for liquid chromatography. Cells may be removed, recovered and analyzed.

13 Claims, 18 Drawing Sheets

Beads packed into flow-through column capture living cells on surface

Related U.S. Application Data provisional application No. 61/832,501, filed on Jun. 7, 2013, provisional application No. 61/858,054, filed on Jul. 24, 2013, provisional application No. 61/873,828, filed on Sep. 4, 2013, provisional application No. 61/913,154, filed on Dec. 6, 2013.

(56) References Cited

U.S. PATENT DOCUMENTS

| 7,482,169 B2 | 1/2009 | Gjerde et al. |
|---|---|---|
| 2005/0255604 A1 | 11/2005 | Gjerde et al. |

OTHER PUBLICATIONS

Tugcu, Nihal; "Purification of Proteins Using Displacement Chromatography" Affinity Chromatography: Methods and Protocols, 2nd Ed., 71-89, 2008.*

Kim, Hee Seung; Hage, David S; "Immobilization Methods for Affinity Chromatography" Handbook of Affinity Chromatography, 35-78, 2006.*

Bickerstaff, Gordon F; "Immobilization of enzymes and cells: some practical considerations" Methods in Biotechnology, vol. 1; 1-11, 1997.*

Nelson, David L; Cox, Michael M; Lehninger's Principles of Biochemistry, 4th Ed., WH Freeman and Company, New York, 2005.*

R Braun et al. Rapid Separation of T Cell Subpopulations with Monoclonal Antibodies and Affinity Chromatography.1982 Journal of Immunological Methods, vol. 54, pp. 251-258.

Jean-Claude Bonnafous et al. Cell Affinity Chromatography with Ligands Immobilized through Cleavable Mercury-Sulfur Bonds. 1983 Journal of Immunol Methods, vol. 58, pp. 93-107.

H Ohba et al. Fractionation of Normal and Leukemic T-Cells by Lectin-Affinity Column Chromatography. 2002 Cancer Letters vol. 184, pp. 207-214.

\* cited by examiner

Elution at physiological temperature
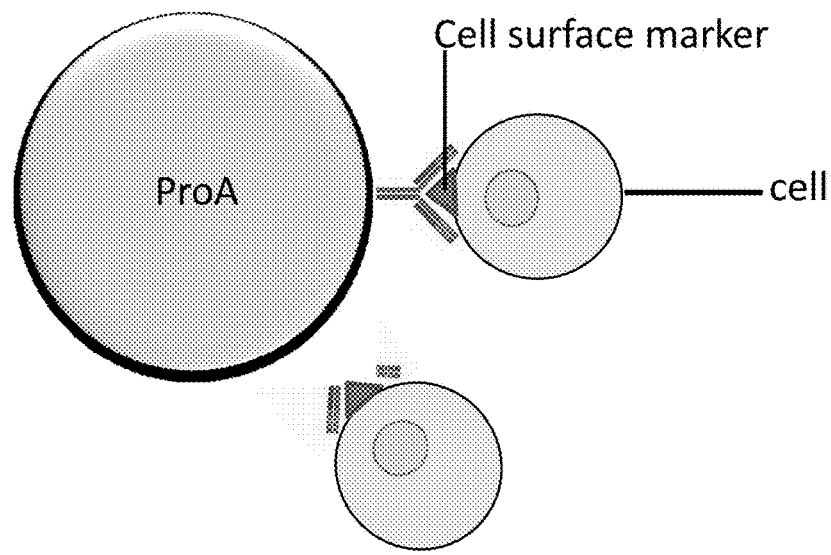
Figure 5
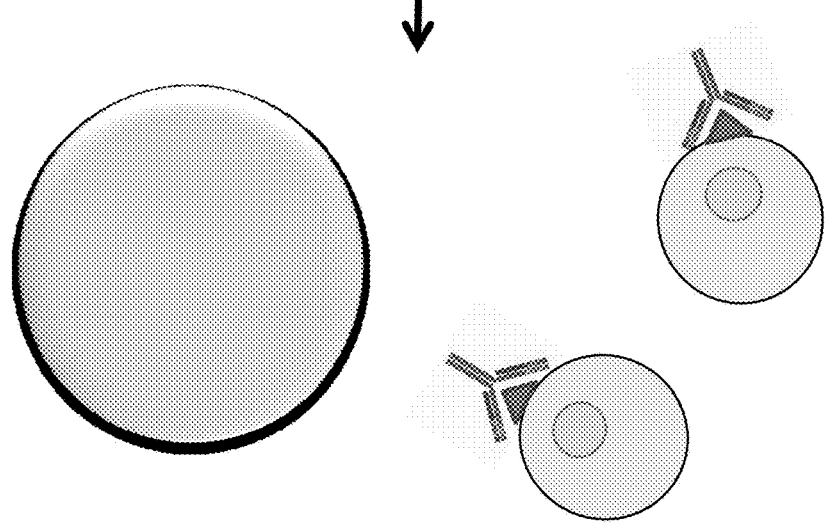

DEVICES AND METHODS FOR PURIFICATION, DETECTION AND USE OF BIOLOGICAL CELLS

FIELD OF THE INVENTION

This invention relates to devices and methods for purifying, detecting and using biological cells. A variety of cell types can be purified from a complex biological sample using a column. The method can be performed quickly and viable cells can be recovered. Purified viable cells can be detected on the column or eluted from the column and detected. Cells on a column can be used as a stationary phase for liquid chromatography. Cells may be removed, recovered, used and analyzed.

BACKGROUND OF THE INVENTION

The primary technology in use today for capturing and purifying cells is magnetic beads. In this technology, a suspension of beads is used to treat a sample containing cells. The magnetic beads contain a tag or chemical entity that is selective for cells or for a certain cell type within the sample. After the cells become associated with the magnetic beads, a magnet is used to collect the magnetic beads and captured cells. The magnetic beads may be re-suspended several times with wash solutions to clean the cells. Finally, a solution can be used to release the cells from the beads and a magnet separates the magnetic beads from the cells.

However, magnetic beads can negatively impact cell viability. This problem is mitigated somewhat by the use of magnetic nanoparticles. The magnetic-activated cell sorting (MACS) method available from Miltenyl Biotec utilizes magnetic nanoparticles to isolate cells. Cells expressing particular surface antigens attach to the magnetic nanoparticles.

For example, the isolation of circulating tumor cells (CTCs) from blood is an area of very active interest at present. These cells which are shed into the vasculature from a primary tumor circulate in the bloodstream and constitute seeds for subsequent growth of additional tumors (metastasis) in vital distant organs. CTCs present in the bloodstream of patients with cancer provide a potentially accessible source for detection, characterization, and monitoring of non-hematological cancers.

Magnetic bead methods are slow and do not always produce pure cell populations. In addition, cells isolated on magnetic beads are may not be viable. There exists a need for a column technology that rapidly captures high concentrations of cells, particularly viable cells and then recovers the cells at high purity for research, detection and for other uses.

In the instant invention, it was discovered that living cells can be used as a stationary phase for a new type of liquid chromatography. In this application, analyte reagents flow through a column in which cells attached to the column medium serve as a stationary phase. Analytes interact with the cell-based stationary phase. The extent of interaction of the analytes with the stationary phase can be measured and used. Later, the cell stationary phase may be recovered and analyzed. It is remarkable that in this type of chromatography, both mobile phase analytes and the stationary phase groups can be analyzed and measured. No previously-described chromatography systems have this capability.

Cells may vary in size and can be vulnerable to shear forces and stress which are exerted by a chromatographic device. These forces may be present while the cells are traveling through the chromatographic system including the tubing, frits and column media. The forces may be present while the cells are present on the column media.

Cells may be susceptible to contamination of various sorts including chemical and biological contamination. However a chromatographic device with shielding for cells in the device is unknown. Chromatographic devices cannot restrict or constrict the flow of liquid in any portion of the flow path including the inlet flow into the pump or column or the exit flow from the column. To restrict or constrict flow would make flow of liquid through the column impossible or at the very least, unpredictable, uncertain and uneven. Cells may be subjected to additional shear forces and biological and mechanical stress when the chromatographic device is sealed. In addition to keep cells alive, they must have nutrients, oxygen and removal of waste gas. Sealing a chromatographic system may cause harm to cells, again in unpredictable ways. There exists a need for a chromatographic system that prevents contamination of cells without harming the operation of the chromatographic system or harming the cells.

SUMMARY OF THE INVENTION

In the present invention, cells are purified from a biological sample using a column. The sample is passed through the column and cells are captured on the solid phase within the column. In some embodiments, the column is within a sealed system that is not open to the ambient surroundings. Sealing means that contaminants may not enter the chromatographic system. Contaminants cannot penetrate the device or enter the liquid phase. In some embodiments, gases may leave the chromatographic device by means of one directional check valves or similar one directional means. After construction of the sealed system and after loading the buffers and sample into the column within the system, and during use of the device, the sample, buffers, fluid lines and reservoirs are not exposed. Contaminants from surroundings cannot penetrate the device or enter the liquid phase. The sample is passed through the column and cells are captured on the solid phase within the column. The solid phase can be a chromatography medium such as a gel resin or an impermeable resin. Following capture, the column is washed to remove material that is not specifically bound to the column medium. In some embodiments, cells can be recovered by passing an eluent through the column, while in other embodiments cells can be manipulated or interrogated on the column.

Cells may be tagged for detection while attached to the column or may be recovered and subject to further manipulation, measurement or detection. In still other embodiments, cells pass through the column while desirable contaminants are captured.

Columns, methods and instruments of the invention may be used to capture and purify cells, clean reagents from solutions containing cells, or detect or use cells. Practice of the invention facilitates the capture of living cells in a flow through column and keeping the cells in a stable form, while the cells are flowing through the column and after the cells have been reversibly captured by the column. This is due to the ability of being able to control the external chemical and physical environment of the cells in a stable, non-disruptive manner. Once the cells are captured, flow through of reagents through the column can be used to allow interaction of reagents and cells to perform, optional on-column manipulation of the cells. These manipulations include interrogation or measurement of interaction of reagents with the cells or of the reagents that interact with the cells. The cells may be tagged with a reagent. Tagging is the attachment of a chemical to the cell to make the cell more detectable with different detectors. Optionally, the cells may be analyzed on the column through direct detection of the cells or materials within the cells. Or the cells may be destroyed and materials removed and analyzed. The cells may be recovered from the column for further detection or interrogation.

In the methods of the invention, whole cells are isolated using a column that contains a bed of medium. In some embodiments, viable cells are isolated from the column. Cells are quite fragile and can rupture easily from a variety of physical conditions such as encountering an object, shearing force, turbulence or incorrect solute concentration. Mechanical cell lysis can be induced by a collision of the cells with micro beads or with tubing and pumping devices associated with a sealed system including peristatic pumps, positive or negative pressure pumps or gravity pumps. Even one breach of the cell membrane is enough to cause catastrophic damage to a cell. Viable cells can die in vitro simply from incorrect storage, processing, transport, exposure to incorrect temperature (heat or cold), pH, medium, vessel, collision with a sharp edge or small passage, etc. Cells may not have oxygen or nutrients to live for a long time or may not be able to remove waste gases from biological function leading to build up of conditions harmful to cell viability. Yet, in order to purify cells quickly with a column process, it is important that cells are passed through a column rapidly to be able to capture, wash and recover cells as quickly as possible. This is especially true when the volume from which the cells are being captured is large.

It is quite remarkable that intact cells and even viable cells can be captured and purified using the columns and methods of the invention. It is surprising that cells can remain intact even after subjecting them to the methods of the invention. Specifically, cells purified via the instant invention are subjected battering motion through a fritted column containing a bed of medium, tubing and perhaps pumps, sometimes repeatedly.

The advantages of invention over prior art include the following active movement steps: 1. Active movement of cells to column bed functional site to capture live cells and to enable capturing cells in a rapid flowing stream: 2. Active movement of reagents to living cells while reversibly attached to the column, to perform on-column chemical reactions/interactions on living cells; to maintain cells in a living state, or to induce cells to perform biological activity and study biological activity: 3. Active movement of washing fluids through the column containing reversibly attached cells, to be able to rapidly and effectively remove nonspecific background cells and matrix molecules from column: 4. Active movement of reagent through the column containing reversibly attached cells, to elute and recover living cells for analysis or further use. All of the active movement steps are rapid with fast flowing fluids, but surprisingly do not harm the cells when the columns and methods of the invention are used. There exists a need for such a column technology that rapidly captures cells, particularly viable or living cells, concentrates them and then recovers the cells at high purity.

In still other embodiments, cells that are captured on the column may be used as a stationary phase. Reagents may be introduced into the column in a mobile liquid phase. Reagents may interact or be retained by the cell stationary phase. These interactions may be measured. Analyte reagents that interact with the stationary phase may be recovered and measured. Later, the cells may be removed from the column and analyzed.

The devices, columns, methods and instruments of the invention can be used with cells, including viable cells and cancer cells. In some embodiments, the column is a pipette tip column. In some embodiments, the column contains a solid medium. Cells can be manipulated or interrogated while bound to the solid phase or cells can be eluted from the column. In some embodiments the flow of sample through the column is bidirectional. In some embodiments the flow rate is high so that the cell purification can be performed in 3 hours or less. In certain embodiments, cells can be isolated, purified, detected or used from a sample in less than 30 minutes or even less. The methods of the invention are quite versatile; many cell types can be isolated and a wide variety of applications are possible.

Columns, method and instruments of the invention can be used in two ways or modes. In one mode the column the flow-through column may be used to capture, tag, measure and recover living cells which may be further processed or analyzed. These cells may be recovered for R&D or diagnostic and analytical purposes. In another mode, the column captured living cells may be used as a liquid chromatography column stationary phase to measure and distinguish analyte reagent interactions with the stationary phase. After serving as a stationary phase, the cells may be recovered for R&D or diagnostic and analytical purposes. Cells of various organ types may be contained on the column for study of the organ and study of how chemicals interact with organ cells.

The devices and methods of the invention can be used for the purification of cells, including viable cells, T cells, organ cells of various types, stem cells and cancer cells and also including biological cells from organisms. A biological sample containing cells is passed through a column containing a solid phase and cells are captured on the solid phase. In some embodiments, the column is a pipette tip column. Cells can be manipulated or interrogated while bound to the solid phase or cells can be eluted from the column. In some embodiments the flow of sample through the column is bidirectional. In some embodiments the flow rate is quite high so that the cell purification can be performed in 3 hours or less. In certain embodiments, cells can be purified from a sample in less than 30 minutes. The methods of the invention are quite versatile; many cell types can be isolated and a wide variety of applications are possible.

BRIEF DESCRIPTION OF THE DRAWINGS

FIG. 1A depicts an aspiration step. FIG. 1B depicts an expulsion step.

FIG. 3A depicts and aspiration step and FIG. 3B depicts and expulsion.

FIG. 5 is a depiction of an embodiment of an antibody capture and release strategy.

DETAILED DESCRIPTION OF THE INVENTION

Figures 1A, 1B:
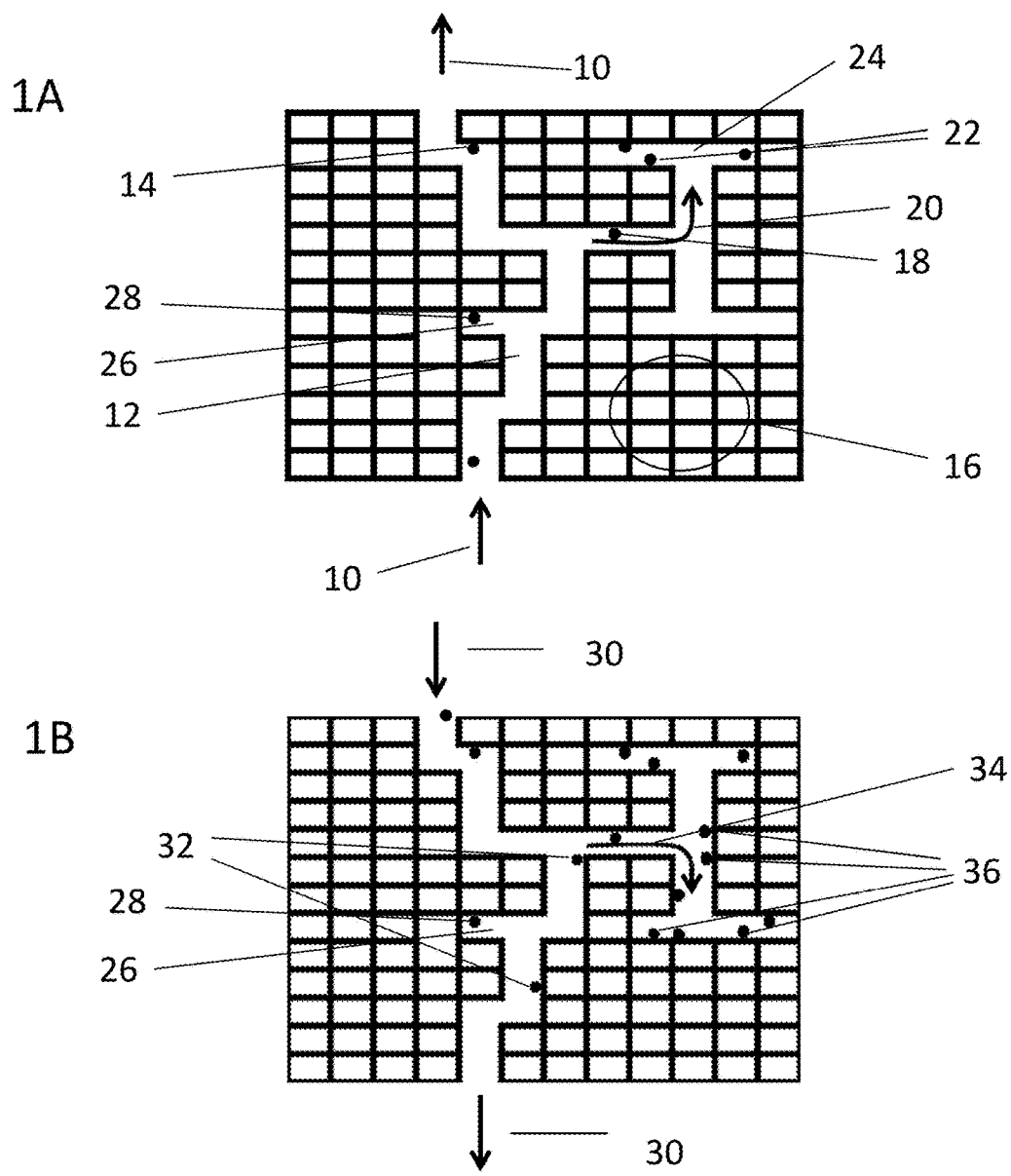
FIGS. 1A-B. Stylistic depiction of flow path, nooks and traps in a column.

In the methods of the invention, whole cells are isolated using a column that contains a bed of medium. In some embodiments, viable cells are isolated from the column. Cells are defined herein as membrane-bound structures that occur as functional units of life (such as in unicellular organisms, e.g. bacteria, protozoa, etc.), or as structural or fundamental units in a biological tissue specialized to perform a particular function in multicellular organisms (e.g. plants and animals). Self-replication is not a necessary property of cells as defined herein; the definition includes entities such as viruses, parasites and exosomes.

Cells are quite fragile and can rupture easily from a variety of physical conditions such as encountering an object, shear force, turbulence or incorrect solute concentration, temperature and many other conditions. Mechanical cell lysis can be induced by a collision of the cells with micro beads. In fact, this is a common method for cell lysis. However, even a little damage, even one breach of the cell membrane is enough to cause catastrophic damage to a cell. Viable cells can die in vitro simply from incorrect storage, processing, transport, exposure to incorrect temperature (heat or cold), pH, medium, vessel, collision with a sharp edge or small passage, etc. Yet, in order to purify cells quickly with a column process, it is important that cells are passed through a column rapidly to be able to capture, wash and recover cells as quickly as possible. This is especially true when the volume from which the cells are being captured is large.

Even though it is important to pass cells through a column quickly, prior art columns have not been able to do this (Braun, R., et al., Journal of Immunological Methods 1982 54, 251-258, Bonnafous et al., J. Immunol. Methods 1983 Mar. 11; 58 (1-2):93-107 and Ohba, H., et al, Cancer Letters (2002) 184, 207-214). In a few cases, cells have been captured on a column using an incubation process where a small sample is applied to the column and then the sample/column is held or incubated in order to capture cells onto the column. Remarkably and in contrast to the prior art, the instant method of passing cells through the column rapidly without harm may also help or facilitate the improved capture of the cells from flowing samples and large samples.

It is remarkable that intact cells and even viable cells can be captured and purified using the columns and methods of the invention. It is surprising that cells can remain intact even after subjecting them to the methods of the invention. In certain embodiments, cells purified via the instant invention are subjected to a repeated back and forth flow battering motion through a fritted column containing a bed of medium. That is, cells can be passed rapidly through a column containing a bed of medium. Furthermore, it is surprising that cells can be manipulated and reacted while captured on the column. The cells can remain attached to the column while undergoing tagging or other reactions. The cells may be used as a stationary phase for liquid chromatography. Analyte reagents may interact with the attached cell stationary phase. Finally, the liquid chromatography stationary phase may be removed and recovered. It is remarkable the stationary phase cells may be recovered in a living, viable state for further use or analysis.

The use of whole cells is an excellent format for cell-based assays for a number of reasons. First, it's possible to work with viable cells, which are closer to an in vivo environment than working with for example, a single protein. In whole cells, targets such as cell surface proteins or protein complexes are likely to be intact and in their native state with respect to folding, etc. Interactions between cells can be studied in some embodiments. Cell signaling pathways can be targeted.

In addition, using cells with column processes has a number of advantages. Columns can be operated in parallel and their operation can be automated. Columns can be sterilized and operated in a sterile environment such as a laminar flow hood. Column processes are relatively gentle; there is no shaking, spinning or exposure to magnets. The kinetics of drug-target interactions can be examined in a column as described below. Cells, molecules or compounds can be added to columns serially to examine the results of each addition. Cells can be isolated quickly on the columns of the invention which aids in the retention of viability.

Column processes with cells give an increased signal to noise ratio when compared to other cell-based assays. Due to the large surface area of the beads, cells can be concentrated at the capture step to increase signal. Wash steps remove non-specifically bound material, reducing noise in a more consistent and complete manner. As a result, these processes are more sensitive because of reduced noise and yield better statistical data because of the increased signal.

Another method to improve the sensitivity and signal to noise ratio is to improve the detectability of the cell. This is performed by reacting and attaching a detecting reagent to the cell while the cell is attached to the column. By performing the tagging process in this manner, the reaction can be done more completely, which increases the sensitivity, and reproducibly, which reduces the noise, both of which increase the signal to noise coming from the cells.

As described above, the columns of the invention contain a bed of medium onto which the cells are captured. The bed can be comprised of beads or particles held in the column by at least one frit below the bed. In certain embodiments, the bed is retained in the column with two frits; one below the bed and one above the bed. It is quite surprising that cells can pass through the frit(s) and the bed of medium and maintain their integrity and in some cases, even their viability.

Consider the physical environment of a liquid sample comprised of cells passing through the frit and bed of medium within a column. The channels through which a cell might flow are not open or linear. Instead, the flow path would consist of a variety of interwoven channels, each with varying and perhaps restrictive diameters, and many possible dead ends marked by repeated turns, bends, winding and twisting. This tortuous path environment is advantageous for the capture of small molecule analytes because the fluid (containing the analyte) gets extensive exposure to the column matrix. However, a cell travelling through this environment could easily be trapped which can kill, damage and/or prevent the cell from being recovered. Adding one or two frits to the column makes the flow path even more tortuous and restrictive. Of course, physically trapping cells within the column matrix is an undesirable outcome quite distinct from targeted cell capture strategies such as affinity binding. Cells that become physically trapped cannot be recovered with an eluent or desorption solvent. Furthermore, if cells are trapped, even temporarily, they could readily rupture or die. This trapping phenomenon was referred by Bonnafous et al. (supra) and teaches away from successful purification of cells by the instant invention.

The columns of this invention have very low back pressures. The columns are packed and constructed to produce these very low backpressures. The columns of the invention have lower backpressures even compared to columns having low back pressure screen frits similar used in previous column technology in which smaller column bed sizes and column body sizes were used (U.S. Pat. No. 7,837,871. However, the backpressure of the columns of the invention is significantly lower than these earlier columns. In addition, the columns are packed in such a way that the flow of cells through the column flow paths is less restricted and does not harm the cells.

Larger columns usually have higher backpressure than smaller columns. This problem is compounded when the columns are operated with low pressure pumps. Pumps such as syringe pumps or pipette pumps apply positive pressure (head pressure) or vacuum to the column to force the flow of fluid through the column. The pressures applied are low and pumping fluids through large columns is limited. As a result, it is more difficult to pump sample and buffers through large bed column resulting in slower flow rates and longer separation times. This can be problem for capturing and recovering cells. Longer residence times in a column will harm the quality of the cells recovered and could prevent the recovery of cells, particularly viable cells.

FIGS. 1A and 1B illustrate the surprising nature of the invention. It is a stylistic depiction of the many potential hazards and pitfalls that could be encountered by cells travelling through a column using bidirectional flow. FIG. 1A depicts an aspiration step in which the flow direction 10 is upward. The matrix of the material (e.g., a polymer) is depicted by closed squares 16. Cells cannot penetrate matrix 16. The flow path through a column bed contains many potential nooks and traps for cells. A clear unrestricted flow path 12 enters and exits the bed. Some cells (e.g., 14) may be captured by the column in flow path 12. As the flow proceeds, many or most of the cells 18 enter dead end flow paths 20 to trap the cells 22 in dead end or restricted passages 24. There are also nooks (e.g., 26) just off flow path 12 that may trap cell 28.

FIG. 1B depicts the fate of cells resulting from back and forth flow through the column. The flow direction 30 is in a downward direction, reversed from upward direction 10 shown in FIG. 1A. Although increased residence time may allow a greater number of cells 32 to be captured, especially from a flowing stream, this reversal of the flow direction 34 can also exacerbate the undesired trapping of many cells 36. It should be noted that cell 28 remains trapped in nook 26.

Figure 2:
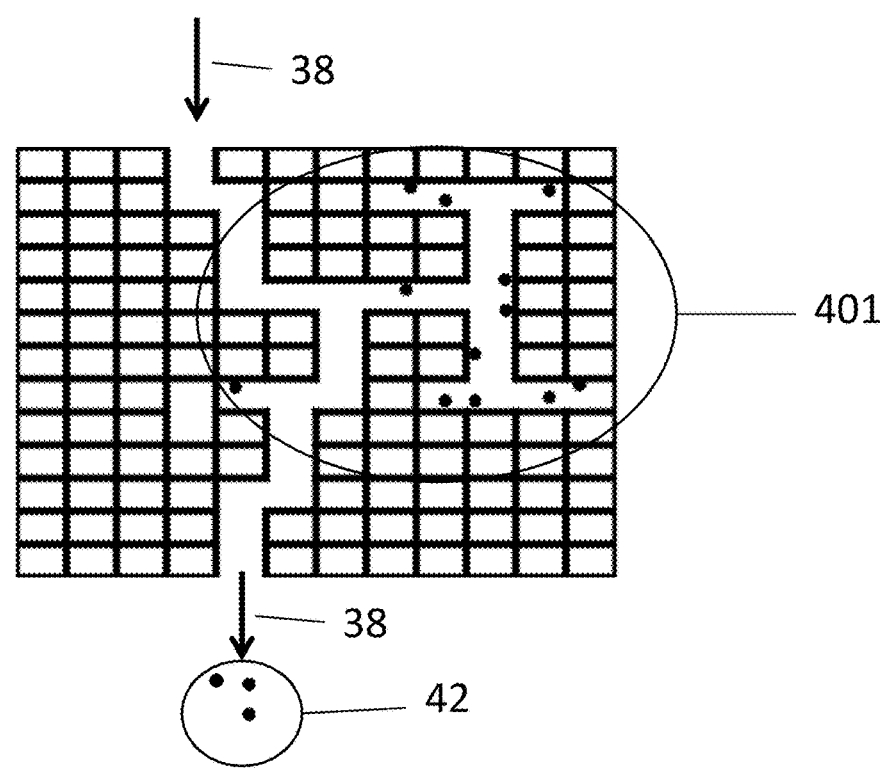
FIG. 2. Elution of cells from the column shown in FIG. 1B.

FIG. 2 depicts the elution of cells from a column. The recovery of cells from a column is attempted with a downward flow direction 38. Most of the cells 401 remain irreversibly trapped. A few cells 42 may be recovered but may or may not be intact. In addition to the risk of cell trapping, a person of skill in the art would expect the column environment or materials to be inhospitable to cells. It is desirable to recover intact and even viable cells. Intact cells are defined herein as cells having no holes or ruptures in their membrane. The column materials or surfaces, such as the frit or column walls might be incompatible with the cell integrity or viability. Protrusions present in the column wall, bed or frit could easily damage or rupture cells.

Figure 3:
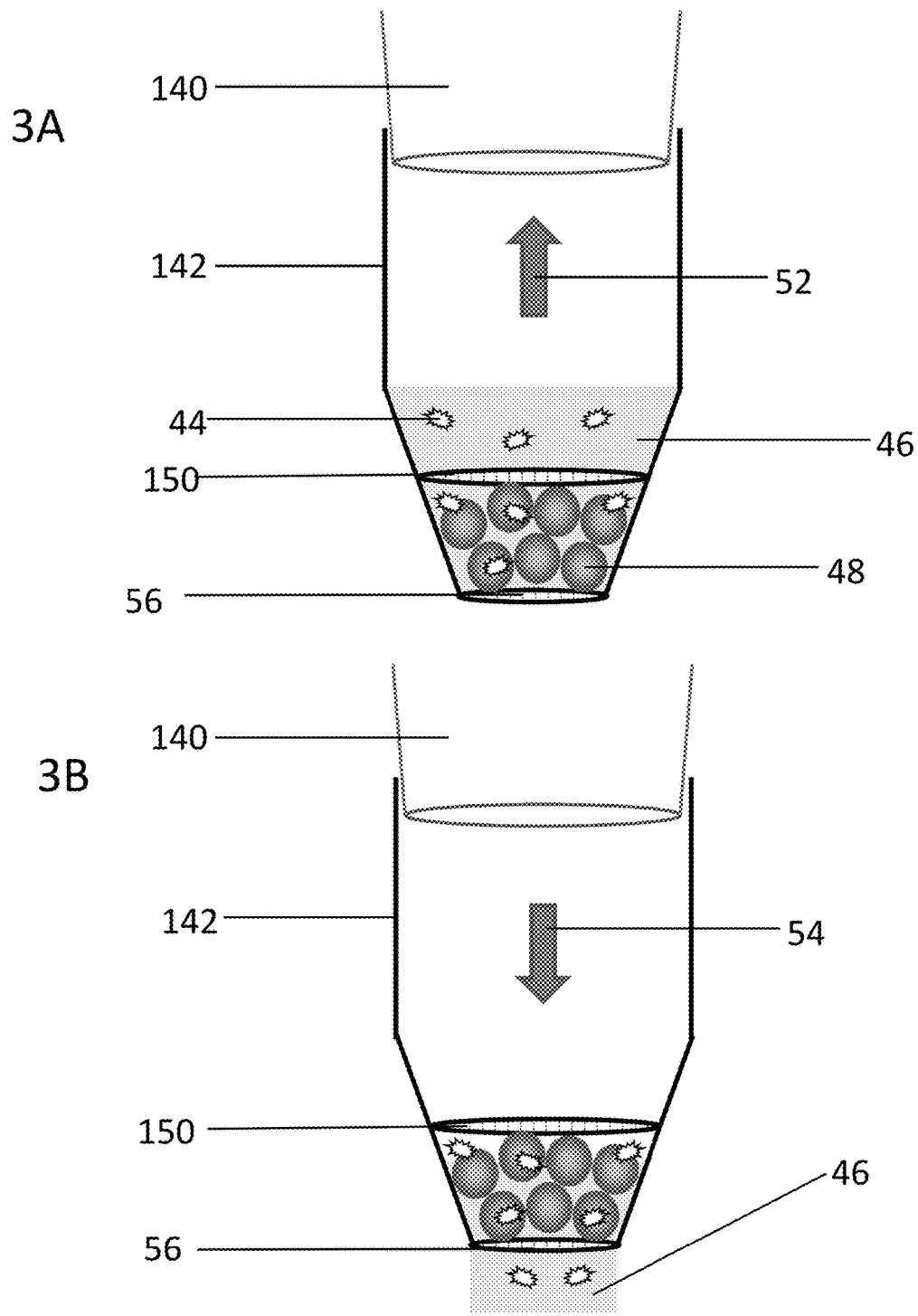
FIGS. 3A-B Depiction of the column and method of the invention.

FIGS. 3A and 3B depict a column and method of the invention. Because the column is packed according to the methods of the invention and because the column is comprised of the frits described herein, it is not subject to the pitfalls described above and shown in FIGS. 1 and 2. Cells in a liquid sample are passed through the column using back and forth flow. In these embodiments, the upper end of column 142 is operatively engaged with pump 140 and sample 46 containing cells 44 is aspirated and expelled through the lower end of the column. During the aspiration step, the sample travels in direction 52, upwards in through lower frit 56 into the bed of beads 48 and then continues through upper frit 150 (FIG. 3A). During expulsion, the sample 46 travels back downward in direction 54, through upper frit 150, into the bed of medium, through lower frit 56 and exits the bottom of column 142 (FIG. 3B). These aspirations and expulsions can be repeated multiple times, the desired result being that intact cells are captured by the medium.

However, columns of the invention capture cells in a reversible process. A vast majority of cells either flow through the column or are reversibly captured. Almost no cells are captured in restrictive channels or dead end channels. The process of cell capture is reversible and the cells are recoverable.

Almost no cells are damaged as they flow through the column, even repeatedly. Intuitively, it seems that the flow paths resulting from back and forth flow would be even more perilous for cells than unidirectional flow, especially when the goal is recovery of viable cells or even intact cells. Cells would pass through the column bed and frit(s) multiple times from both directions, increasing the probability of cell damage or death.

This invention provides devices and methods for isolation of cells using a column format. The cells can be eukaryotic or prokaryotic. The term cells, as used herein is not limited to self-replicating entities. Included in the definition are viruses, exosomes and parasites.

In certain embodiments, the isolated cells are viable. In some applications, the maintenance of cell viability is less important. For example, cells purified on the column may be counted, labeled, analyzed by DNA sequencing, PCR or other assays.

The Sample

The starting sample is usually a heterogeneous mixture from which cells are purified. The sample can be from any biological source and can contain viable cells. For example, cells can be captured from biological fluids such as blood, urine, saliva, spinal fluid or semen, tissues such as brain or tumor tissue and other samples such as fecal (stool) or hair. In certain embodiments, sample preparation steps are performed prior to the isolation of cells on a column. For example, when cells are captured from blood, the blood can be fractionated by centrifugation and only the buffy coat loaded on the column. Alternatively, whole blood can be diluted or loaded directly on the column. In certain embodiments, the devices and methods can be used for the analysis of cells from crime scene samples.

In some samples, cells are free and exist individually in solution. There are other samples, such as tissues in which cells are aggregated or form cell-cell adhesions. In addition there are cells that start off as tissues but then slough off to form free cells. Circulating tumor cells for example exist in blood and may form an adhesion to other places in the body. Sample preparation techniques exist that can mechanically or chemically disrupt and dissociate cells in order to form single cell suspensions. These methods are gentle and in wide use. Kits are available that use enzymatic digestion in combination with mechanical disruption and the option of heat. There are products available from Miltenyi Biotec and Roche Life Sciences for example.

Cells isolated using methods and devices of the invention are not limited to a particular cell type; cells captured by the methods of the invention can be eukaryotic or prokaryotic cells. Eukaryotic cells can be from protozoa, chromists, plants, fungi or animals such as mammals, amphibians, birds, fish, reptiles and invertebrates. Cells can be engineered or wild type.

A non-limiting list of cells that can be isolated by the columns of the invention includes epithelial cells, hormone secreting cells, sensory transducer cells, neuron cells, glial cells, lens cells, metabolic cells, storage cells, barrier function cells such as lung, gut, exocrine glands and urogenital tract, kidney cells, extracellular matrix cells, contractile cells, blood and immune system cells, germ cells, nurse cells, interstitial cells, activated B-cells, mature B-cells, cytotoxic T-cells, helper T-cells, activated T-cells, natural killer (NK) cell, monocyte and macrophage, activated macrophage, endothelial cell, smooth muscle cell, dendritic cell, mast cell, fibroblast (stromal), epithelial cell, adipocyte, stem cells, granulocytes, platelets, erythrocytes circulating tumor cells, Alexander cells, astroglia, B Lymphoblast, B Lymphocyte, basophil, cortical neurons, cutaneous T cells, lymphocytes, embryonic cells, enterocytes, epithelial cells, transformed cells, immortalized cells, large T antigen, epithelial neuroendocrine, erythroblast, fetal, fibroblast, glial cell, glioblastoma, Hela cells, histocyte, human papillomavirus, hybridoma: e.g., helper T lymphocyte, keratinocyte, killer cell, large cell, lymphoblast, lymphoblast B lymphocyte, lymphoblast Human Immunodeficiency Virus, lymphocyte, medulloblastoma, megakaryoblast, melanocyte, melanoma, monoblast, myeloblast, neuroblast, neuroendocrine, osteoblast, pluripotent stem cell, pre-B lymphoblast, promyeloblast, retinoblastoma, Schwann cell, squamous cell, T lymphoblast, T lymphocyte, T-cell.

Cells isolated can be from any tissue. A non-limiting list of tissue type examples follows. lung, ascites, bone marrow, bone, brain, cervix, colon, connective tissue, duodenum, eye, kidney: skin, kidney, liver, lung, lung: pleural effusion, mammary gland, ovary: ascites, ovary, pancreas: lymph node, pancreas, peripheral blood, pharynx, placenta, prostate, retinal pigmented epithelium, skin, spleen, stomach: derived from metastatic pleural effusion, stomach, submaxillary salivary gland, testes, thyroid, tongue, urinary bladder, uterus, adrenal gland, airway epithelium, aorta, bladder, blood, bone marrow, brain, breast, breast derived from metastatic site: pleural fluid, bronchiole, bronchus, carcinoma, cecum, cord blood, cornea, ectocervix, embryo, embryonic kidney, endocervix, endometrium, epithelium, esophagus, eye, fetus, foreskin, gingival biopsy, heteromyeloma, intestine, kidney, lung adenocarcinoma, lymph node, lymph node derived from metastatic site: peritoneal effusion, mammary gland, marrow, mesencephalon, mesothelium, muscle, nasal septum, nervous, palatal, palatal mesenchyme, pancreas, peripheral blood, peritoneal effusion, peritoneum, peritonial effusion, pharynx: derived from metastatic site: pleural effusion, pleura, prostate, rectum, retina, retroperitoneal embryonal tumor, retroperitoneum, skin: derived from metastatic axillary node, skin: derived from metastasis on skin of thigh, small intestine, somatic cell hybrid, stomach, submaxillary, synovium, testis, thymus, thyroid, tonsil, trachea, trunk, umbilical vein, ureter, uterine, vagina, vascular, vein, vertebral epitheloid carcinoma and vulva.

Cells of a particular organ type or part of the body can be loaded onto a column. These include cells from the heart, liver, kidney, bone marrow, gut or from a spectrum of human tissues, including the circulatory, endocrine, gastrointestinal, immune, integumentary, musculoskeletal, nervous, reproductive, respiratory, urinary systems and other types. The cells may be from a specific individual or from the general population. Columns with these cells may be operated alone or in concert with other columns containing cells from other organs or biological systems. The columns can be operated in the chromatographic system in parallel or in series to mimic biological functions. Reagents can be introduced into the columns to determine the interaction of the reagents and the effect on the cells or to study or use the cells as organs.

The Columns

Columns used in the invention contain material capable of reversibly capturing cells. Cells can be captured and eluted from the column. In some embodiments, the eluted cells are viable.

The columns of the invention can be made in a wide range of sizes. Column bodies can range from a 10 µL pipette tip to a 200-mL column. These large volume columns are described in more detail below. Of course, larger columns can be used to process larger liquid volumes. For example, a 20-ml pipette tip column containing 1 ml of resin can accommodate approximately 19 ml of a biological liquid sample. Column bed volumes can be in the range of 10 µL to 100 mL, 20 µL to 50 mL, 30 µL to 10 mL, 40 µL to 5 mL, or 50 to 1 mL.

The columns can be comprised of beads or particles. In certain embodiments, the column medium can be a monolith, a filter or a combination of materials. In those embodiments which utilize beads, the bead size can be quite large, on the order of 100-900 microns or in some cases even up to a diameter of 3 mm. In other embodiments, the bead size is comparable to that used in conventional columns, on the order of 45-150 microns. The average particle diameters of beads of the invention can be in the range of about 10 to 20 µm to several millimeters, e.g., diameters in ranges having lower limits of 10 µm, 20 µm, 30 µm, 40 µm, 50 µm, 60 µm, 70 µm, 80 µm, 90 µm, 100 µm, 150 µm, 200 µm, 300 µm, or 500 µm, and upper limits of 20 µm, 30 µm, 40 µm, 50 µm, 60 µm, 70 µm, 80 µm, 90 µm, 100 µm, 150 µm, 200 µm, 300 µm, 500 µm, 750 µm, 1 mm, 2 mm, or 3 mm.

Column formats and methods for use can vary significantly. In some embodiments, the columns are pipette tip columns. Pipette tip columns are defined herein as columns capable of operative engagement with a pipette, syringe, peristaltic, pressure, syringe pump or liquid handing robot, or any pumping device that can impart positive and negative pressures to liquids or gases above the liquid to force the liquid through the column. Pipette tip columns have a lower end in which liquids can be aspirated and expelled. In most embodiments, pipette tip columns have a frit to retain media located at the lower end and an optional frit at the upper end. In certain embodiments, liquids are passed through the column in a back and forth manner.

In other embodiments, the column can be in a cartridge or a column with end fittings. In this embodiment, of the column end fittings connect to liquid flowing tubes in and out of the column. If necessary, the ends of the columns contain frits to hold media in the column chamber. In other embodiments, the columns have inlet and outlet fittings attached to the ends. Tubing can be attached to these inlet and outlet fittings.

In other embodiments, the column is a non-compressed packed bed column. Non-compressed packed bed columns are used with unidirectional flow or they can be used in bidirectional flow.

The columns may be used with any pumping device including the pumps listed above and including pumping devices used in liquid chromatograph instruments including piston pumps and pressure type pumps.

In certain embodiments, the columns can be integrated into a multi-well plate. In other embodiments, the column can be positioned within a syringe.

It was discovered that although bed compression was low with light force packed columns, the bed was still compressed and the beads were compressed, restricting the flow of cells through the column. We improved capture of cells with affinity columns of the invention by packing columns to form physical channels without constrictions or dead ends. The bed can be positioned between two frits using a packing method in which pressure is not used to compact the bed. Columns of the invention do not have bed compression. With bed compression, beads are deformed which causes them to fill the interstitial space. Column beds can be compressed with a force to pack the column into the column space. This force can be applied with vacuum or pressure of liquid containing the packing beads for physical compression of the beads into the column chamber. With columns of the invention, the beads are not pressed together to form flow constrictions or dead-end flow spaces. The volume packing density of the bed can be measured as a ratio of the volume of beads without having any direct contact causing the deformation of the bead divided by the volume of same amount of beads where the bed has been compressed. As the volume of the column is decreased for the same amount of beads, the volume packing density increases. A bed that has been compressed 10% has a volume packing density of 1.00/0.90 which equals 1.11. A bed that has been compressed 20% has a volume packing density of 1.00/0.80 which equals 1.25. A bed that has not been compressed is 1.00/1.00 which equals 1.00. Columns of the invention that contain compressible beads have a volume packing density within the range of 1.00 to 1.05.

In certain embodiments, the columns are comprised of a more compressed packed bed of medium. For example, a packed bed of medium might be used for enrichment columns in which cells pass through but contaminants are captured.

The space between the resin particles can be important. The space can increase with a non-compressed packing of the column. This space may provide flow channels suitable for capture, washing and recovery of cells without trapping the cells within the packing material. In many embodiments, the columns can contain a mobile bed or a bed that packed in such a way that the beads are not compressed and the flow path will not be restricted. Using this method, the resin can pack and form channels in such a way that cells can move through the resin with reduced chance of damage and an increased chance of capture.

The column packing of the invention can be described functionally. Columns that are packed properly allow cells to pass through the bed without being trapped within the resin. In a column packed for use with cells (and lacking an affinity group for capture), at least 90% of the cells can pass through the column bed without being trapped. In some embodiments, at least 90%, at least 95%, at least 96%, at least 97%, at least 98% or at least 99% of the cells can pass through the column without being trapped. These numbers reflect the percentage of cells that can make it through the column in a single pass without being trapped.

In certain embodiments, the column medium is a hydrated gel resin. Gel resin is non-rigid and must be packed carefully. Also, in these embodiments, the resin may be coated with a high boiling point liquid prior to use as described in U.S. Patent Application US20050045543.

It some embodiments, an impervious resin is used. The use of an impervious resin can be an improvement because cells are large and in many cases, they cannot enter resin bead pores. Most prokaryotic cells range in size from 0.2 to 5.0 µm in diameter and most eukaryotic cells range in size from 1.0 to 100 µm in diameter. The reduction in non-usable surface area will decrease reagent costs as the capacity of the column is decreased. The use of a resin with the rigid structure will also facilitate easier column packing procedures.

Example 18 describes the synthesis of a biotinylated silica resin. First, hydroxyl groups were added to the bead surface. Then, amine groups were produced by reacting silanol with the hydroxyl groups. In a third step, biotin is reacted with the amine groups.

In most embodiments, cells are captured on the surface of the beads and not in the interior of the beads however, in certain embodiments, this may not be the case. Cells can be captured in large pore media. The number of cells that can be captured depends on the diameter of shape of the cells and the available surface to which cells can be reversibly captured as a monolayer. Beads that are compressed not only restrict or eliminate the flow path through which cells can move without getting trapped. Compressed beads reduce the effective surface area of the bead which in turn, reduces the effective capacity of the resin to reversibly capture cells.

The effective capacity of the column of the invention can be dependent upon accessible surface of the beads of the column. The effective capacity of a column should be distinguished from the actual capacity of the column, which is based on the total number of functional groups. As the beads become compressed and touch each other, some of the functional groups that are located on the surface of a bead may be inaccessible to cells flowing through the column and are not available for capture. Since columns of the invention contain beads that have limited or no compression, the effective capacity of the column approaches the capacity based on the total surface area of the media contained within the column. This is another improvement of columns of the invention over previously-described columns.

Column Frits

In certain embodiments of the invention, one or more frits are used to contain the bed of medium within a column. The frits of the invention are porous, since it is necessary for fluid to be able to pass through the frit. The pore size should be large enough to prevent plugging with cells or cell debris. It is important that the frit does not provide dead-end or restricted-end flow paths that could potentially trap or damage cells. It is desirable that the frit have little or no affinity for liquids or cells with which it will come into contact during the column use.

In certain embodiments, one frit (e.g., a lower, or bottom, frit) extends across the open channel of the column body. Often, the bottom frit is attached at or near the open lower end of the column. A bed of separation medium is positioned inside the open channel and in contact with the bottom frit. In many embodiments, a top frit is employed, however it is not mandatory. In certain embodiments, there is a gap between the bed of medium and the top frit. This gap is referred to as a bed-frit gap.

Frits of various pores sizes and pore densities may be used provided the free flow of liquid is possible and the solid phase is held in place. However, the frits must have specific porosity characteristics. It is not only a matter of having sufficiently large pores. The pore shape is important as well. Pores cannot be destructive or restrictive to cells.

Frits of the invention preferably have pore openings or mesh openings of a size in the range of about 5-500 µm. In certain embodiments, the pore size is in the range of 10-200 µm, 33-150 µm, e.g., about 33-43 µm. Frit pore sizes of 20, 33, 37 and 43 um pore size are acceptable. Of course, increasing the frit pore size can only be done if the packing material retained.

The frits of the invention can be made from any material that has the required physical properties as described herein. Examples of suitable materials include polymers, fiber, fabric, plastic (including sintered plastic), nylon, polyester, polyamide, polycarbonate, cellulose, polyethylene, nitrocellulose, cellulose acetate, polyvinylidine difluoride, polytetrafluoroethylene (PTFE), polypropylene, polysulfone, PEEK, PVC, metal and glass. However, any suitable material that meets the above functional requirements can be used for the frit.

Certain embodiments of the invention employ a membrane screen as the frit. The use of membrane screens can provide low resistance to flow and hence better flow rates, reduced back pressure and minimal distortion of the bed of medium. The membrane can be a woven or non-woven mesh of fibers that may be a mesh weave, a random orientated mat of fibers i.e. a "polymer paper", a spun bonded mesh, an etched or "pore drilled" paper or membrane such as nuclear track etched membrane or an electrolytic mesh.

Some embodiments of the invention employ a relatively thin frit. The frit or frits should be sufficiently thin such that cells will not become trapped or die within the frit during column operation. In most embodiments, the frit thickness is less than 6000 µm or less than 4000 µm (e.g., in the range of 20-4000 µm, 40-2000 µm, or 50-350 µm). In certain embodiments, the frits are less than 200 urn thick (e.g., in the range of 20-200 µm, 40-200 µm, or 50-200 µm), or less than 100 urn in thickness (e.g., in the range of 20-100 µm, 40-100 µm, or 50-100 µm). However, thicker frits can also be used in some embodiments, frits up to 1 mm, 2 mm, 3 mm, 4 mm, 5 mm and even 6 mm thick may be used if the pore size of the frit can be increased dramatically.

The frit can be attached to the column body by any means which results in a stable attachment. For example, the screen can be attached to the column body through press fit, welding or gluing.

Frit and Column End Design for Cells for Different Types of Chromatography

Partitioning and frontal breakthrough chromatography are performed using unidirectional flow while step gradient or displacement chromatography can be done using either unidirectional or bidirectional flow.

Since flow is unidirectional for partitioning and frontal/breakthrough chromatography, there are specific design considerations necessary for the frits and column ends. Specifically, the column end dead volume and flow distributor and the frit are critical to performing the separations to prevent diffusion of the chromatographic analyte band and without trapping cells. In addition, in order to load the column, the column end flow diffusors and frits must accommodate back and forth flow without trapping the cells. Cells must be able to travel through the frits in either direction without getting trapped. Conventional liquid chromatographic column ends and frits are not compatible with cells because they will trap cells. Using a screen frit does not solve the problem because this frit is flexible and the bed may move with the reverse direction flow. This will cause the column bed to move into the column end flow distributor when the flow is reversed and could cause the cells to be damaged. The flow distributor must be deeper and compatible with cells (not damage them) to prevent this even though this design will result in band broadening.

The design described above can also be used for step gradient and displacement chromatography. In a liquid chromatographic format, the flow is likely to be unidirectional although the column flow could be used in unidirectional or bidirectional flow format and cell loading of the stationary phase is likely to be bidirectional. The dead volume of the column end and frit is not critical to performing the separations since there is no chromatographic analyte band to diffuse. Nevertheless, the frit and column end should not trap cells.

Sterile Columns and System

In certain embodiments, the columns, reservoirs, tubing and flow paths are sterile. In these embodiments, the columns materials can be assembled from sterile components in a sterile setting such as a clean room. Components can be sterilized by methods known in the art such as filtration, irradiation, chemicals and heat.

Alternatively, terminal sterilization can be performed. Terminal sterilization is defined herein as sterilization of the manufactured columns. In this embodiment, the columns and system can be sterilized prior to use. Once the system with column is made sterile, the system may be sealed to maintain sterility. A sealed system does not let outside materials enter the flow path of the system. There may be venting valve or other types of valves or membranes in the system but these would only allow the out flow of materials and not allow contamination of the system.

Column sterilization after manufacture can be performed by a number of methodologies. In one embodiment, columns can be assembled and then sterilized by autoclaving as described in the examples below. Alternatively, terminal sterilization treatment can be performed for example, by irradiation.

The column hardware, media and system can be sterilized. For example, water swollen gels and other column media may be sterilized. Impervious organic and inorganic column materials may be sterilized. Substrates based on silica and other inorganic materials may be sterilized.

Column Operation

In the methods of the invention, a sample containing cells is passed through a bed of medium or solid phase within a column. The cells are captured on the column medium while other sample constituents pass through the column. The column with captured cells is washed and the purified cells can be released from the column or manipulated on the column.

Although it is not required, columns of the invention may be operated using back and forth flow. In some embodiments, liquids are aspirated and expelled through the lower end of the column. This method is referred to as back and forth flow or bidirectional flow. In these embodiments, a pump, such as a liquid handling robot is operatively engaged with the upper end of the column and liquids (such as the sample, wash and eluent) are aspirated and expelled through the lower end of the column, such as a pipette tip column. Multiple aspirate expel steps are often used with back and forth flow. Back and forth flow can also be used in a packed bed column such as those used in a liquid chromatograph.

In other embodiments, unidirectional flow is used to pass liquids through the column. In these embodiments, fluids are added to the upper end of the column and flow is in a downward direction through the column and out the lower end. In some embodiments, the unidirectional flow is used to pass liquids from one end of the column to the other end. In some embodiments, the inlet and outlet of the column may be interchanged.

The sample can be passed through the column with the use of a pump, a vacuum or even gravity. When unidirectional flow is used, liquids can be passed through the column multiple times. That is, the flow-through can be collected and loaded onto the column again.

The method can be performed in an automated or semi-automated fashion. In some embodiments, the method can be performed manually using a hand-held pipette or a syringe. The term "semi-automated" is defined as a process by which some steps are performed under electronic control while other steps, such as moving the column from well to well are performed manually. For example, a semi-automated method could be performed using the electronic E4 pipette (Mettler-Toledo International Inc.) which is installed with firmware and software. The semi-automated process can be performed in parallel with two or more columns.

The term "automated" is defined as a process by which sample processing is performed by a robotic system controlled by a computer program. In these embodiments, the timing for each processing step and programming of the pumping device can be programmed such that the purification can be performed in a walkaway fashion. This automation process may be performed with columns in parallel. Even though backpressures are low and the capture, wash and purification of cells is a difficult process, columns of the invention may be operated in parallel with automation.

Because of the very demanding design and performance requirements of capturing the cells in a reversible fashion, columns of the invention may have different flow properties. For example the backpressure of the column may be very low. However, the backpressure may increase as the column becomes loaded with cells that have been captured. Nevertheless, automated methods can be used successfully to purify and recover live cells with column, methods and apparatus of the invention.

Often, it is desirable to process a large volume of a liquid, e.g., a biological fluid. Sample volumes larger than the column bed or larger than the column body can be processed by repeated aspiration and expulsion of the sample. It is surprising that repeated aspiration and expulsion can be performed without harming the sample. Alternatively, large sample volumes can be loaded onto the columns through the open upper end and collected from the open lower end. Sample loading can be performed repeatedly as described above.

In some embodiments, the sample is comprised of a flowing stream. In these embodiments, the cells are captured by the column from a stream that is pumped into the column and flows through the column. Because the capture process is from a flowing stream, samples larger than the bed volume of the column can be captured.

Columns of the invention are capable of capturing cells from large sample volumes, i.e. samples larger than one bed volume or one column volume. In some embodiments, the sample is comprised of a flowing stream. This is in contrast to previously-described columns which require small volume samples limited to one bed volume and smaller (Braun et al., Bonnafous et al. and page Ohba et al. (supra)). In addition, Braun and Bonnafous teach that it is necessary to incubate the sample for several minutes before the separation process can begin. It appears that their columns required incubation time for the cells to become captured by the resin and therefore were not capable of capturing cells from a flowing sample. Without being bound by theory, it appears the cells had to diffuse or undergo orientation to the affinity site in order for the capture process to occur.

Intuitively, it seems that a slow flow rate would be advantageous for the capture of cells on a column. There are several reasons for this. First, the cell surface protein must have the correct orientation to be captured by the antibody (or other capturing group) on an affinity resin. Second, there must be sufficient time for the affinity group to bind and capture the cells. These two parameters improve as the flow rate is decreased. Furthermore, a slow flow rate would be gentler, lessening the chance of damage to the cells by the solid surface of the medium and/or column hardware.

However, even when slow flow rates are used, cells travel through the column at relatively high linear velocities. A high linear velocity would be expected to exacerbate the potential problems listed above. For example, a cell could become lodged in a dead end with greater force, making it more difficult to free the cell. While a cell travelling at a relatively slow velocity might slide or sidle around an obstacle, a cell travelling at a high velocity might be ruptured.

However, in the columns of the invention, rapid flow rates are possible. The use of rapid flow rates decreases separation time which positively impacts cell viability. Although the cells may be subjected to more frequent and harder collisions within the column body, they are able to survive even with repeated passes through the column and even with the use of back and forth flow. Even through rapid flow rates would be expected to decrease the opportunity for the cell capture, they allow capture of the cells without damage.

Columns of the invention can accommodate a variety of flow rates, and the invention provides methods employing a wide range of flow rates, oftentimes varying at different steps of the method. In various embodiments, the flow rate of liquid passing through the media bed falls within a range having a lower limit of 0.1 mL/min, 0.5 mL/min, 1 mL/min, 2 mL/min, or 4 mL/min and upper limit of 0.1 mL/min, 0.5 mL/min, 1 mL/min, 2 mL/min, 4 mL/min, 6 mL/min, 10 mL/min, 20 mL/min, 30 mL/min, 40 mL/min, 50 mL/min or greater.

A faster flow rate reduces the time for purification which is advantageous for cell viability. On the other hand, a fast flow rate is more likely to damage the cells.

It can be important to purify cells rapidly to maintain viability. Isolation of cells can be performed remarkably fast using the columns and methods of the invention. Cells can be isolated in less than 3 hours, less than 2½ hours, less than 2 hours, less than 90 minutes, less than 75 minutes, less than 60 minutes, less than 50 minutes, less than 45 minutes, less than 40 minutes, less than 35 minutes, less than 30 minutes, less than 30 minutes, less than 25 minutes, less than 20 minutes, less than 15 minutes or less than 10 minutes. In other embodiments, cell purification can take longer, particularly when viability is not as important.

Columns of the invention have flow paths that allow the cells to be captured from flowing streams. Capture is a fast process and so can be performed with a flowing sample. This is a great improvement over the previously-described columns because capture from a flowing stream allows the capture of samples from volumes that are larger than the bed volume and in some cases, larger than the column volume. In one embodiment, the flowing sample stream is aspirated and expelled back and forth through the column at least once. In many embodiments, the sample is passed back and forth through the column bed multiple times. There is no practical limit to the number of back and forth cycles although lengthy procedures may be harmful to the cells, particularly viable cells.

Cells can be captured from multiple sample aliquots processed in series or from multiple cycling from a large volume sample aliquot. Capture from a flow stream may be performed with unidirectional flow. In some embodiments, the capture is performed using slow flow rates, 100-200 µL/min but the capture process is still successful with faster flow rates, up to 10 to 40 bed volumes/minute.

Cells traversing the column several times before being captured have a greater chance of becoming damaged or trapped. With each flow through of the sample through the column, 95%, 96%, 97%, 98%, 99%, 99.5%, 99.9%, 99.99% percent of the cells are either captured or travel through the column and are not trapped or injured. With each cycle, additional cells may be trapped. For example if 99% of cells are unharmed with each pass through the column, this number is reduced to 99% of 99% or 98% with the second pass (or one full back and forth cycle). With each additional cycle, the reduction is another 2%.

When a sample containing cells is passed through the column, at least a portion of the cells are captured by the material within the column. The sample may comprise a variety of cell types, e.g., blood and it may be desirable to capture only one cell type. In some cases, rare cells such as circulating tumor cells are captured on the column medium. In these cases, the cells captured can be a very small percentage of the total number of cells in the sample. In some embodiments, the number of cells captured can be relatively small.

In some embodiments, viable cells can be recovered from the column. In these embodiments, it is important to maintain the appropriate conditions for cell viability. Factors such as pH, buffering carbon dioxide concentration, temperature and osmolarity must be considered in order to keep cells alive and healthy. For example, viable cells can be stored in sterile buffers such as phosphate buffered saline (Ca/Mg$^{++}$ free) or HEPES (N-2-hydroxyethylpiperazine-N'-2-ethanesulfonic acid) or others known in the art. These buffers can contain EDTA, HBSS (Hank's balanced salt solution), heat-inactivated fetal bovine serum and other constituents. One reference for such media can be found on the UCSF Cell Culture Facility website.

However, viable cells are not required for all applications. For instance, it may be desirable to determine whether a particular cell type is present in a sample or to perform PCR on cells isolated using the columns and methods of the invention.

After the capture step, the columns can be washed with buffer or water to remove any material that is not specifically bound to the column medium. The wash liquid can be passed through the column by any means or rate described above for the sample. The volume of the wash liquid can be greater than that of the column. The wash step may be repeated once or several times.

Following the column wash, the cells can be eluted from the column by passing an eluent through the column. A variety of elution strategies are described below. However, when viable cells are desired, the eluent and elution conditions must be chosen carefully to avoid or minimize harm to the cells. The eluent can be passed through the column by any means described above for the sample. The elution step may be repeated once or several times. In certain embodiments, the eluent can be incubated on the column for a period of time to increase the efficiency of cell elution. After the purified cells are eluted from the column, they can be analyzed by any means desired.

Because the columns are packed to minimize cell trapping, they can be very efficient in isolating the desired cell type. It is possible to capture at least 50%, at least 60%, at least 70%, at least 80%, at least 85%, at least 90%, at least 95% and possible even 100% of the desired cells from a particular sample.

After cells are isolated, an assay may be performed to determine cell viability or to count the number of viable cells.

In the columns and methods of the invention, cells can be captured from rapidly flowing streams. As an example, for column with diameters ranging from 2 mm-4 mm, capture is from cells moving through the column at 0.05-20 mm/sec, 0.1-10 mm/sec, 0.2-5 mm/sec, 0.3-3 mm/sec, 0.4-2 mm/sec and 0.5-1 mm/sec. The linear velocity at 0.1-10 mm/sec corresponds to absolute flow rates of about 100 µL/min to 10 mL/min respectively. As an example, for column with diameters ranging from 4 mm-4 mm, capture is from cells moving through the column at 0.05-20 mm/sec, 0.1-10 mm/sec, 0.2-5 mm/sec, 0.3-3 mm/sec, 0.4-2 mm/sec and 0.5-1 mm/sec. For some commonly used columns, the linear velocity at 0.1-10 mm/sec corresponds to absolute flow rates of about 500 µL/min to 5 mL/min respectively. As another example, for column with diameters ranging from 10 mm-15 mm, capture is from cells moving through the column at 0.05-20 mm/sec, 0.1-10 mm/sec, 0.2-5 mm/sec, 0.3-3 mm/sec, 0.4-2 mm/sec and 0.5-1 mm/sec. For these columns, linear velocity at 0.1-10 mm/sec corresponds to absolute flow rates of about 1 mL/min to 100 mL/min respectively. As yet another example, for column with diameters ranging from 15 mm-40 mm, capture is from cells moving through the column at 0.05-20 mm/sec, 0.1-10 mm/sec, 0.2-5 mm/sec, 0.3-3 mm/sec, 0.4-2 mm/sec and 0.5-1 mm/sec. For these columns, linear velocity at 0.1-10 mm/sec corresponds to absolute flow rates of 5 mL/min to 500 mL/min respectively. Columns of the invention of other diameters operate at linear and absolute flow rates corresponding relative to the examples given.

The following steps are example of a chromatographic procedure for purification of cells for recovery and detection.
1. Treat or activate column or cells to make the column suitable to be able to capture cells.
2. Load cells onto column from a flowing stream.
3. Wash nonspecific bound materials from the column using a flowing stream.
4. Optionally tag cells with a reagent that reacts with a group on the surface of the cell. The tag reacts with an attachment group or entity that is optionally different than the attachment group used to capture the cell to the column.
5. Optionally measure cells with the cells attached to the column. Optional detectors are infrared, surface and transmission VIS/UV, fluorescence, chemiluminescence spectrophotometers.
6. Optionally lyse cells or elute the components of the cells for analysis. The lysing may be done partially, or over a long time period using gentle conditions to remove components of the cell for processing and/or analysis.
7. Remove and recover cells for analysis of the cells and/or further R&D processing, growing or transforming of the cells or further R&D and/or therapeutic use of the cells.

Active Movement

The movement of reagents and cells in cell-based assays and magnetic bead assays is based on diffusion. Reagent and cells travel through solution by diffusion. This process is attractive because it is not disruptive to cells i.e. the processes treat cells gently. This is important because rapid changes in the chemical and physical environment of the cells can injure or kill the cells.

But with diffusion, fine control of the chemical environment can be difficult to attain because the addition and removal of reagents is slow and residual materials cannot be removed easily. It may be difficult to change reagents that are in contact with the cells or control changes in the buffer concentration or pH. The diffusion process can be slow and cells can die simply through natural causes.

We use the term active movement to describe the use of pumps to force cells, by a fluid pumping action, to travel in a flowing stream to and from tubing and column connections, fittings, frits and column media. Active movement can be performed by unidirectional flow and bi-directional flow. The term active movement is also used to describe the pumping of reagents to immobilized cells.

The danger of active movement is killing cells by rapid changes to their environment. Cells can be trapped or injured by shearing forces produced by the rapid movement of cells or fluids moving to and past cells. One advantage of active movement is being able to perform an operation of cell manipulation rapidly. Another advantage is ability to have a rapid and fine control of the chemical environment surrounding the cells. These advantages also allow new manipulation and control of cells and reactions of cells with reagents. In addition, active movement allows the cells to be used as a stationary phase in a chromatographic column.

There are several types of cell active movement. These include:
1. Active movement of cells to and from a column, to the column medium and to capture functional groups, all without damage to the cells. This allows the opportunity of the column to capture live cells in a reversible form.
2. Active movement of reagents to live cells on the column to able to perform chemical reactions and interactions with the live cells. Rapid and fine control of the concentration of the reagents is possible while removing other reagents that may have side reactions. Even finer control is achieved with the use the cell-compatible, low dead volume frits and impervious column media. Through control of chemical or physical changes such as pH or concentration, interrogation of reagents and cells is performed. Reagents and interactions can be driven to completion rapidly and completely.
3. Active movement and recovery of biological products from the live cells on the column. The products may change depending on how the cells are treated or by changing the materials that may contact the cells. The products may be studied or used.
4. Active movement removal of non-specific materials (background cells and other nonspecific or undesired molecules) from cells of interest. This removal it possible to accurately distinguish between cells of interest and background cells to dramatically improve purity, detection, chemical interrogation, chemical reactions, etc.
5. Active movement of reagents to add and to remove analyte reagents from cell stationary phase column. Analyte reagents can be added and recovered rapidly from the cell stationary phase column for analysis or further operations under controlled chemical elution conditions.
6. Active movement of reagents to remove cells from column. Living cells can be recovered rapidly from the capture column for analysis or further operations under controlled chemical elution conditions. Removal can be complete and rapid. Cells can be detected on line for real-time quantification and interaction measurements.

Active movement is rapid but gentle and can help cells to remain alive. Living cells can be tagged on column under controlled chemical conditions. Living cells and reagents that interact with living cells can be interrogated on column under controlled chemical conditions.

Another aspect of active movement for living cell columns is the precise and accurate control flow of reagents through the column. With columns of the invention, the concentration of the reagents flowing to and flowing from the cells on the column is controllable and predictable. One means of being able to accomplish this using low dead volume frits to hold the media in the column that does not contain dead spaces or spaces that trap liquids or materials. Another means of being able to accomplish this is by using media that is impervious. This means reagent concentrations are not diluted or changed unpredictably in concentration by penetration of reagents or cells into the media matrix. These changes in reagent concentration by penetration are explained in a later section.

Dilution Prevention for Reagents and Eluents

In some embodiments of the invention, reagents are introduced into a column in a unidirectional flow. Introduction of a reagent into a column forms the wave front of the reagent traveling through the column. It was discovered that for some embodiments of the columns of the invention, the wave front for an eluent slug traveling through the column would travel at slower speed than expected. Furthermore, the shape of the wave front was diffuse and the width of the wave front was broad. Cells could not be eluted quickly and effectively. Then, it was discovered that the time necessary for adding reagents to a column was also slower than expected. For example, the process of adding an antibody capable of capturing a cell required an appreciable time to react all of the functional group sites. Also, eluting a captured cell from a column required a large amount of eluting reagent and an appreciable amount of time and flow to effectively elute cells from the column. Performing the reaction by adding reagents in a unidirectional flow can be slow due to slow reaction kinetics. But it was discovered that an additional factor appeared to contribute to the slow reactions.

It was discovered that some reagents would enter the interior of the bead whereas the cells would penetrate very little or remain on the surface of the bead. Because of this, reagents were being used or consumed in locations within in the columns where cells were not present. Thus, some reagents were consumed but did not serve any useful function with regard to capture of cells, reacting with cells or release of cells.

It was further discovered that this uneven distribution of reagents depended on the type and size of reagent. Very large materials such as cells or biomolecules such as DNA, RNA or other (bio) polymers); smaller materials such as biomolecules including antibodies, fragments of antibodies, lipids, nucleic acids, aptamers; smaller materials such as buffer reagents including organic compounds, salts, bases, and acids; and finally very small materials such as the molecules of the solvent itself water all entered or penetrated columns of the invention to different degrees and depths, depending primarily on the size of the reagent and property of the substrate. Furthermore, it was discovered that when a solution containing these materials was pumped into a column, the localized concentration of some reagent materials would change depending on whether or not the material entered the matrix of the column media. If the reagent entered the bead matrix, then the localized concentration of the reagent would decrease, especially relative to a reagent that did not enter the resin matrix. The degree to which the concentration decreased depended on the degree the reagent could enter the resin phase. The smallest reagents were diluted most while intermediate reagents were diluted to a smaller degree and the largest reagents, cells, normally did not decrease the localized concentration of the material introduced into the column.

The reagent concentration and amount needs to be considered carefully for each step of the purification method including 1) activating a column for capture, 2) capturing a cell from solution 3) washing non-specific materials away from a column containing captured cells, 3) reacting a tag to cells contained within or captured by a column, 4) washing away unreacted tagging reagent from a column, 5) introducing an eluting reagent to release captured cells from a column, 6) introducing reagents to controllably lyse cells captured by a column, 7) introducing analyte reagents to a column containing a cell stationary phase and 8) eluting or displacing analyte reagents from a cell stationary phase column.

It was discovered that the concentration profile of a material pumped through a column is a wave front that travels through the column as it is being pumped. The concentration profile of reagent that penetrates the resin matrix will decrease and be lower than the concentration profile of a reagent that does not penetrate the bead. That is, the wave front is delayed if the reagent penetrates the column medium.

Two methods for controlling the localized reagent concentration of reagents introduced to columns of the invention were developed. For the consideration of this discussion, the term reagent may refer to very large materials (e.g. cells, DNA, RNA), larger materials (e.g. antibodies, fragments of antibodies, lipids, nucleic acids, aptamers) smaller materials (e.g. buffer reagents, organic compounds, salts, bases, and acids) or very small materials (e.g. solvent molecules). The first method involves changing the reagent concentrations relative to each other depending on whether or not a reagent (or material or molecule type) penetrates the resin matrix. If any particular reagent penetrates the resin, then the concentration of that reagent concentration is increased in correspondence to the degree of penetration into the resin. That is, for reagents that penetrated the resin matrix, the concentration of the reagent can be increased to compensate for dilution of the reagent. For a fully penetrating reagent, the concentration can be increased by up to almost 100% because the resin matrix occupies approximately 50% of the column volume. If the reagent only penetrates 50%, then the concentration of reagent would be increased 50% to maintain the localized concentration relative to a non-penetrating reagent.

A second method is to control and limit the penetration of reagents and solvent into regions of the media where cells do not reside. One way to accomplish this is to use a resin impervious to the specified reagent in the same manner that cells are impervious. For example, in certain embodiments, a resin can have very small pores that don't allow entry of most reagents. In some embodiments, the resin is impervious.

In still other embodiments, the resin contains large pores, big enough for cells to reversibly enter. If it is desired to control or increase the concentration of any particular reagent as the wave front is passed through the column, then the column solid phase is chosen to be or reacted to be made impervious to that particular reagent.

The cell penetration of a media substrate can be less than 10%, less than 5%, less than 1% or is none or zero penetration into the impervious resin matrix. The reagent penetration into a medium substrate can be less than 50%, less than 20%, less than 10%, less than 5%, less than 1% or it is possible to have no penetration when using an impervious resin matrix. Reactions in which controlling reagent penetration into the substrate should be considered include 1) activating a column for capture, 2) capturing a cell from solution 3) washing non-specific materials away from a column containing captured cells, 3) reacting a tag to cells contained within or captured by a column, 4) washing away unreacted tagging reagent from a column, 5) introducing an eluting reagent to release captured cells from a column, 6) introducing reagents to controllably lyse cells captured by a column, 7) introducing analyte reagents to a column containing a cell stationary phase and 8) eluting or displacing analyte reagents from a cell stationary phase column and other reagents used in a cells purification, cell detection and cell stationary phase chromatography.

Affinity resins have a gel like, hydrophilic structure that swells in the presence of water or polar solvents. The swollen polymers contain pores that allow solvent to diffuse in and out of the resin bead. The swelling can be significant. For example a cellulose, agarose or Sepharose substrate will swell 5-10 times its original size when contacted with water. In the swelling process pores are opened up producing beads with a pore diameter up to 500 angstroms and larger allowing biomolecules to migrate and diffuse into the bead along with the solvent.

In some embodiments of the invention, a polymer substrate is used that does not swell upon exposure to water. In substrates which do not swell in water (solvent), buffer molecules, bio molecules and/or cells cannot enter pore in the substrate. The substrate may be polystyrene, polyacrylate type, polyester, or other olefin polymer or other polymer, or inorganic substrate material. Inorganic polymers include polysiloxane and polyphosphazene, silicone, etc. Inorganic materials include aluminum oxide, zirconia, silica, etc. Organic polymers include low density polyethylene (LDPE), high density polyethylene (HDPE), polypropylene (PP), polyvinyl chloride (PVC), polystyrene (PS, nylon, nylon 6, nylon 6,6, Teflon (Polytetrafluoroethylene), thermoplastic polyurethanes (TPU), polytetrafluoroethylene (PTFE), polychlorotrifluoroethylene (PCTFE) and other polymers. When exposed to water, the particle size increase of these substrates is less than 5%, 4%, 3%, 2%, and 1%. Swelling may be controlled by controlling the polarity of the interior of the substrate to be nonpolar or non-hydrophilic. Water is limited in entering the interior of the bead and hydrating the bead.

In other embodiments of the invention, the swelling of the substrate upon exposure to water may be more, but still limited. In these cases the interior of the bead or substrate may be more hydrophilic, but swelling is limited because the polymer beads are crosslinked or held physically together. In some embodiments water may not enter the substrate. Buffer molecules, biomolecules and cells also may not enter the substrate. In some embodiments, some limited amount of water and buffer molecules may enter the substrate, but bio molecules and cells may not enter the substrate. When exposed to water, the particle size increase of these substrates is less than 50%, 40%, 30%, 20%, 10% 5%, 4%, 3%, 2%, and 1%.

Another counterintuitive method for increasing the effectiveness of reagents was developed for columns of the invention. Consider a column in which cells are connected to a streptavidin resin via a biotinylated antibody. Cells can be eluted from such a column with biotin in a first order replacement reaction. First order means that there is a one-to-one replacement of the eluent molecule to the biotinylated antibody holding the cell to the media. The reaction is an equilibrium reaction. The equilibrium of the reaction shifts as the biotin concentration is increased.

However, another way to increase the effectiveness of the reaction is to lower the capacity of the resin. With a lower capacity resin, a lower concentration of biotin can be used to drive the equilibrium reaction to same extent. In a related manner, if the same biotin concentration is used in a pervious higher capacity resin versus a less pervious lower capacity resin, then the lower capacity resin will respond faster. The lower capacity resin will also respond to a greater extent with the same concentration of biotin because the equilibrium reaction will be shifted to more complete reaction. That is, a reaction can be driven to completion by adjusting either the resin capacity or the reagent concentration. More complete elution or displacement of the biotinylated antibody occurs with the effectively higher amount of reagent. Also, if the reagent is consumed in the reaction, as they are in displacement reactions, then the mass amount of the reagent needed is also lower with the lower capacity of the resin.

In another embodiment, an antibody attached to a cell is bound to a protein A resin. The antibody can be displaced by competition with a protein A molecule.

Finally, there is another factor that controls the amount of each reagent needed and the effectiveness of reagents added to the column. The actual capacity of the resin is determined by the actual number of functional groups in a resin. This can be expressed for example as milliequivalents of functional group per mL of bed volume of a column or milliequivalents of functional groups per gram of resin, etc. But the effective capacity of a resin can be much different and often lower than the actual capacity. The effective capacity of the column is a measure of sites that function in capturing, processing, using and recovering cells in the column. The effective capacity does not include functional sites that do not capture cells. In some columns of the invention, the ratio of actual capacity to effective capacity is quite high because most of the sites are not accessible to the cells. In the columns of the invention, the ratio of actual capacity to effective capacity can be in the range of 1000 to 1 or 100 to 1. However, if the column does not contain functional groups that are impervious to cells, then the ratio is much lower, which can be desirable. In some columns of the invention, the ratios are much lower and require lower reagent concentrations. Desired ratios of actual capacity to effective capacity for cells for columns of the invention include 10 to 1, 5 to 1, 3 to 1, 2 to 1, 1.5 to 1, 1.2 to 1 and is 1.1 to 1, 1.05 to 1 and 1 to 1.

In some embodiments, a more impervious resin is beneficial. By limiting placement of the functional groups to sites that are accessible to the cell, two things are accomplished. First the capacity per unit volume or mass of the column is lowered making the reagents introduced into the column more effective per unit concentration. In some embodiments, improved columns of the invention have capacities in the range of 100,000 cells per mL of column bed volume, 500,000 cells per mL, 750,000 cells per mL, 1,000,000 cells per mL, 2,000,000 cells per mL, 5,000,000 cells per mL, 10,000,000 cells per mL, 20,000,000 cell per mL, 50,000,000 cells per mL, 100,000,000 cells per mL, 200,000,000 cells/mL or 500,000,000 cells per mL of column bed volume. Second, the ratio of actual capacity to effective capacity for cells becomes lower. This also increases the effectiveness of reagents introduced into the column because they are interacting only with functional group sites that are accessible or useable by cells. In some embodiments, this means placing or having the sites on the surface of the bead or surface of the media. Still, from a standpoint of recovering as many purified cells as possible, it is desirable to increase the column capacity to as high as possible. One way of accomplishing this is to increase the total surface area of a column by decreasing the bead diameters contained in the column. However, increasing the capacity by decreasing the bead size may not be possible because this may also increase the restrictions to flow with smaller spaces between the resin beads. Therefore, although it is counterintuitive, low capacity resins of the invention are more desirable for this reason as well.

Temperature

In some embodiments, the column is operated in a cold room while in other embodiments, the column can be operated at room temperature or at a temperature greater than room temperature. The optimum temperature for running the column will depend on parameters such as the application, the column medium and the cell type. In some embodiments, the columns are operated in a hood such as a laminar flow hood to maintain sterility.

1. Temperature may be used to help preserve cells. These can be sample cells, cells captured on the column or cells eluted from the column.

2. Temperature may also be used to change the nature of the cells being captured and control selectivity of the column to capture particular cells.

For example incubation of red blood cells at 37° C. may affect the expression of some antigens, such as CD35 and CD11b. While temperature may not affect expression of CD15s, CD44, or CD62L, maintaining a temperature of 37° C. may accelerate apoptosis of neutrophils with subsequent shedding and decreased expression of CD16. Peripheral blood neutrophils prepared at 4° C. may express less CD35 and CD11b than those prepared at room temperature, suggesting release of some granular contents at higher temperatures. It has been found that changes in surface marker expression of CD11/CD18 occurred with temperature change, such as warming neutrophils from 4° C. to 37° C.

In some embodiments, the sample and the column are maintained at a lower temperature such as 4° C. to retain the integrity of the sample and maintain a constant selectivity. In some embodiments, the sample and/or column are maintained at a higher temperature up to 35° C., 37° C., 40° C., 45° C., 50° C. and even higher. In some embodiments, the sample and/or column are maintained at sub-ambient temperatures or higher than ambient temperatures depending on the particular property studied or used.

Capture and Elution Strategies

Various mechanisms can be used for cell capture on the medium. Non-limiting examples include a functional group that has affinity for the cells, use of a tagged antibody, ion exchange, a tagged aptamer and an antibody loaded resin (Pro A, G etc.) covalent bonded linkers (alkyl thio, etc.), hydrogen bonded linkers. In some embodiments, a biotinylated antibody binds a cell surface marker and cells are isolated using a streptavidin resin. In certain embodiments, the resin can be comprised of an antibody. Other capture mechanisms such as hydrophobic interaction, reverse phase, normal phase, ion pairing and ion exchange can be used as long as the cells are not damaged.

Antibodies used with the invention can bind cell surface markers. There are many commercially-available antibodies that bind cells. One list of over 2800 antibodies can be found using the product finder on the Miltenyi Biotec website.

The following is a non-limiting list of human cell surface markers that can be identified by PCR (see the SABiosciences website). http://www.sabiosciences.com/rt_per_product/HTML/PAHS-055A.html). Lists are also available for mouse and rat cell surface markers.

B-Cell Surface Markers:
Activated B-cells: CD28, CD38, CD69, CD80, CD83, CD86, DPP4, FCER2, IL2RA, TNFRSF8, CD70 (TNFSF7).
Mature B-cells: CD19, CD22, CD24, CD37, CD40, CD72, CD74, CD79A, CD79B, CR2, IL1R2, ITGA2, ITGA3, MS4A1, ST6GAL1.
Other B-cell Surface Markers: CD1C, CHST10, HLA-A, HLA-DRA, NT5E.
T-Cell Surface Markers:
Cytotoxic T-cells: CD8A, CD8B.
Helper T-cells: CD4.
Activated T-cells: ALCAM, CD2, CD38, CD40LG, CD69, CD83, CD96, CTLA4, DPP4, HLA-DRA, IL12RB1, IL2RA, ITGA1, TNFRSF4, TNFRSF8, CD70 (TNFSF7).
Other T-cell Surface Markers: CD160, CD28, CD37, CD3D, CD3G, CD247, CD5, CD6, CD7, FAS, KLRB1, KLRD1, NT5E, ST6GAL1.
Natural Killer (NK) cell Surface Markers: CD2, CD244, CD247, CD7, CD96, CHST10, IL12RB1, KLRB1, KLRC1, KLRD1, NCAM1.

Monocyte and Macrophage Cell Surface Markers:
Activated Macrophages: CD69, ENG, FCER2, IL2RA.
Other Monocyte and Macrophage Surface Markers: C5AR1, CD163, CD40, CD63, CD74, CD86, CHST10, CSF1R, DPP4, FCGR1A, HLA-DRA, ICAM2, IL1R2, ITGA1, ITGA2, S100A8, TNFRSF8, CD70 (TNFSF7).
Endothelial cell Surface Markers: ENG, ICAM2, NOS3, PECAM1, SELP, TEK, VCAM1, VWF.
Smooth Muscle cell Surface Markers: MYH10, MYH9, MYOCD.
Dendritic cell Surface Markers: CD1A, CD209, CD40, CD83, CD86, CR2, FCER2.
Mast cell Surface Markers: C5AR1, FCER1A, FCER2, TPSAB1.
Fibroblast (Stromal) Surface Markers: ALCAM, COL1A1, COL1A2.
Epithelial cell Surface Markers: CD1D, KRT18, KRT5, KRT8, EPCAM.
Adipocyte Surface Markers: REIN.

Figure 4:
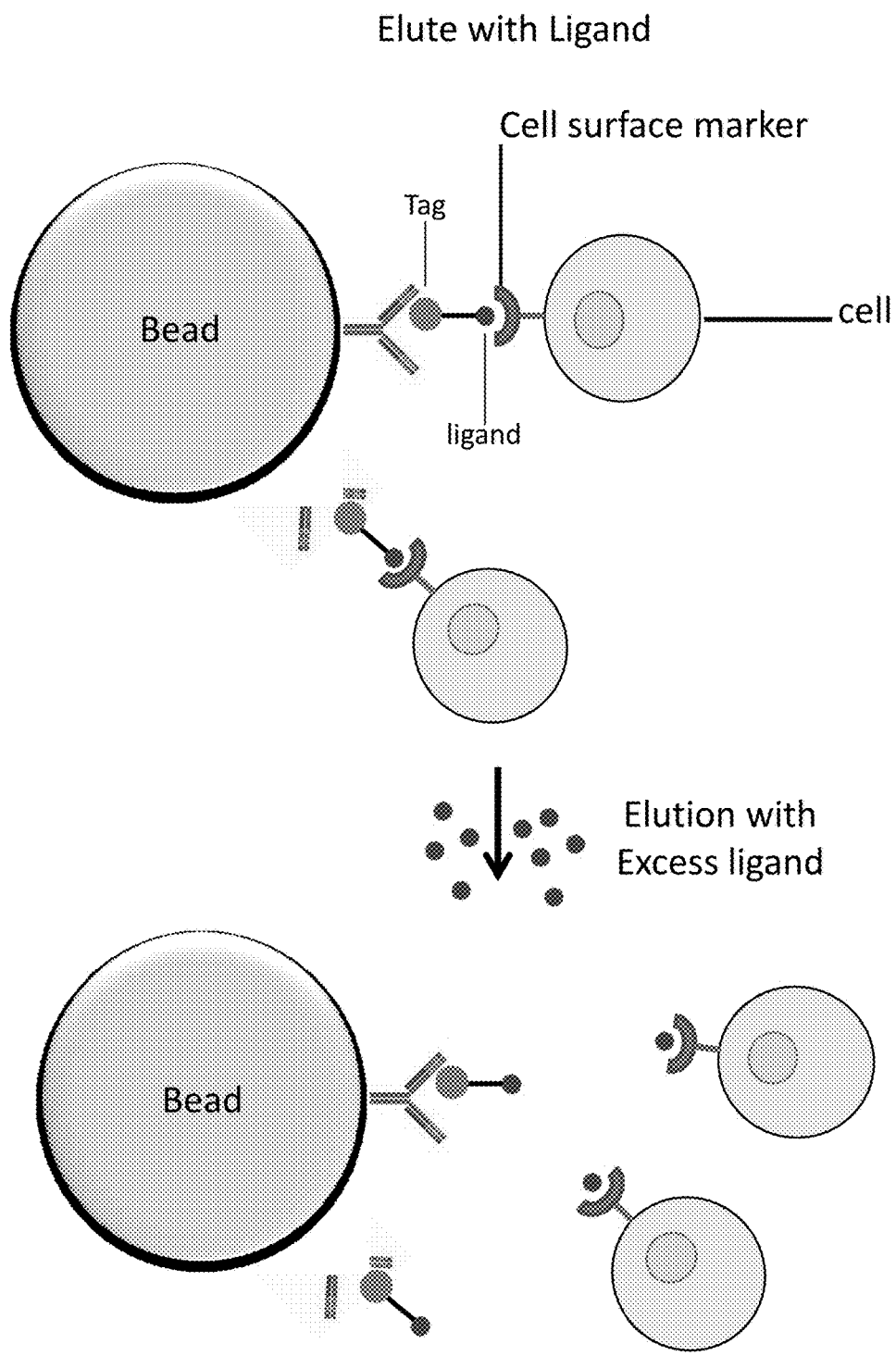
FIG. 4 is a depiction of an embodiment of a competition elution strategy.

One strategy involves competition. Cells are captured with a ligand that binds a cell surface marker and then eluted with the same ligand. In another example, cells bound to antibodies captured on ProA resin can be eluted with ProA or a similar molecule. Alternatively, the ligand could be bound to a tag which in turn, binds an antibody as shown in FIG. 4.

Another competition strategy utilizes ANTI-FLAG resin. A FLAG-labeled Fab or Antibody that binds a cell surface marker could be engineered e.g., in *E. coli*. Many other types of functional groups can be used for competitive, equilibrium type reactions to capture and optionally elute and recover cells.

Alternatively, cells can be eluted by a physical change such as a change in pH or temperature as shown in FIG. 5. Preferably, an eluent can be selected that does not harm the cells, particularly when the recovery of viable cells is desired. In one example, a temperature-sensitive ProA resin can be used such as Byzen Pro resin made by Nomadic Bio Science. Using this type of resin, cells can be eluted at neutral pH by increasing the temperature as shown. In a second example, cells can be captured by antibodies specific to cell surface markers and eluted using a low-pH eluent. In this example, the elution step could be performed rapidly followed by a quick transfer of the purified cells to a neutral-pH solution.

A variety of affinity strategies can be used to capture cells on the column. However, it is also possible to use ion exchange. In alternate embodiments, cell capture may not be desired. Gel filtration (size-exclusion chromatography) can be used to enrich a particular cell type by separating cells away from non-cell components or by separating cells from each other based on their size. For example, circulating tumor cells (CTCs) are larger than other cell types and can be separated from other cells using size exclusion chromatography. Gel filtration could also be used to clean up a sample, e.g. a diagnostic sample. Non-cell material could be removed or taken up by the column.

In some embodiments, cells captured on a column can be eluted using enzymatic cleavage. For example, cells could be captured using proA resin charged with antibodies that bind a cell surface marker. The antibody could then be cleaved with an enzyme such as papain or pepsin to elute the cells.

The columns and methods of the invention can be used to capture and elute viable healthy cells or diseased cells. In certain embodiments, cells can be captured using an aptamer specific to a cell surface marker. Aptamers can be single- or double-stranded RNA or DNA oligonucleotides. Aptamer sequences can be determined using Systematic Evolution of Ligands by Exponential Enrichment (SELEX) or other selection processes (see for example Base Pair BioTechnologies, Inc., Houston, Tex.). The aptamers can contain non-standard or modified bases. As used herein, a "modified base" may include a relatively simple modification to a natural nucleic acid residue, which confers a change in the physical properties of the nucleic acid residue. Such modifications include, but are not limited to, modifications at the 5-position of pyrimidines, substitution with hydrophobic groups, e.g., benzyl, iso-butyl, indole, or napthylmethyl, or substitution with hydrophilic groups, e.g., quaternary amine or guanidinium, or more "neutral" groups, e.g., imidazole and the like. Additional modifications may be present in the ribose ring, e.g., 2'-position, such as 2'-amino (2'-NH$_2$) and 2'-fluoro (2'-F), or the phosphodiester backbone, e.g., phosphorothioates or methyl phosphonates.

Aptamers have been shown to be capable of cell capture. For example, Shen et al. used DNA aptamer-functionalized silicon nanowires to capture and release non-small cell lung cancer cells (Shen, et al. Advanced Materials, Volume 25, Issue 16, pages 2368-2373, Apr. 24, 2013).

Figure 6:
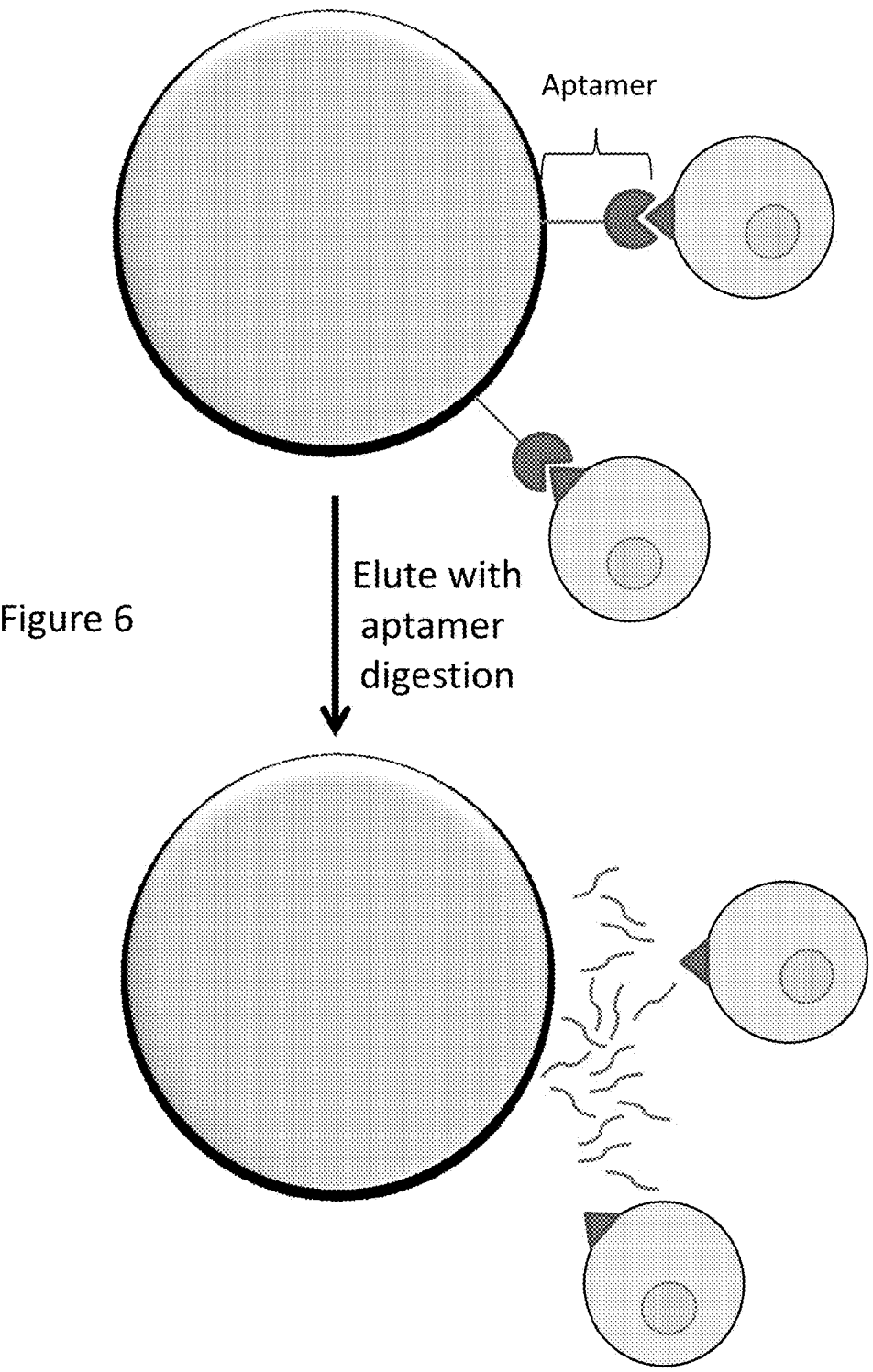
FIG. 6 is a depiction of an embodiment of an aptamer capture and release strategy.

Aptamers can be chemically conjugated to chromatographic beads. For example, see Zhou et al., Trends in Analytical Chemistry. 2012 41:46-57. Alternatively, biotin-labeled aptamers could bind streptavidin resin. Cell elution can be performed by a means with disrupts the aptamer or the aptamer-cell bond. For example, RNase could be used to perform elution from an RNA-based aptamer as shown in FIG. 6. Other elution strategies that can be employed with aptamers are anti-sense, photocleavage (at an appropriate wavelength), use of an enzyme, heat, denaturing solution or chemical cleavage. An aptamer comprised of a disulfide bond could be treated with a reducing agent to disrupt the bond and release a bound cell. An aptamer containing a magnesium-dependent fold could unfold and release a bound cell with the addition of a chelator.

The capture of cells is difficult, especially under flowing stream, especially under high flow rates, especially under high linear velocity of fluid containing cells traveling through the column.

Cell surface markers can be used to capture the cells. However different cell surface markers may have different uses or functions in methods of the invention. For example, a cell may be captured with one type of marker and tagged with another type of marker. A third marker or more and/or combination of markers may be interrogated, measured or studied.

Elution of the cell can be accomplished using a strategy directed toward release of the capture marker without disrupting any of the other markers. However, if the cell is used in a cell stationary column, then capture and elution of analytical reagents can be performed with a third type of marker, without disrupting any of the other markers.

Once the cell stationary phase/analyte reagent measurements are performed, the cells of the stationary phase may be analyzed. A tag may be introduced into the column to give a detectable signal to the cell. In these cases a suitable marker on the cell may be targeted to react with the cell to make the cell detectable. A tag may be introduced before cell elution or after cell recovery.

Removal of the Solid Chromatography Medium from the Column

In some embodiments, the resin with cells attached can be removed from the column after the capture and wash steps. In these embodiments, the resin (with cells attached) can be placed in a well. Cell lysis can be performed if desired. PCR can be performed either on whole cells or lysed cells. Nucleic acids can be isolated and analyzed e.g., by sequencing.

Removal of the resin can be performed by piercing the bottom frit of the column and then pushing the resin into a well with air or liquid. A frit piercing tool can be used for this purpose. In some embodiments, the frit piercing tool is comprised of a handle and a piercing point however, a wide variety of geometries are possible. The tool can be used manually by grasping the handle and pushing the piercing point of the tool through the column frit and into the bed. Then the tool is removed and the column is placed above a tube or microplate well which will receive the resin. Air or liquid can be used to push the resin into the well.

In another embodiment, the frit piercing tool can be recessed in a well, handle side down into the well of a microplate. The column is positioned above the well and pushed down into the well to pierce the frit. The piercing tool can be removed or remain in the well. Air or liquid can be used to push the resin into the well.

These embodiments can be performed in automated parallel fashion.

Large Column Operation

Large columns are defined herein as those columns having a bed size of at least 100 µL and a capacity between 2 mL and 100 mL. In some embodiments, large columns can be pipette tip columns while in other embodiments, the large columns are not pipette tip columns. Large columns that are not pipette tip columns have a body and bed volume of 1-100 mL.

Larger columns of the invention have a number of different properties from the smaller columns. It is not simply a matter of scaling up small columns to produce large body affinity columns. First, larger columns can have a different geometry than the smaller columns. Specifically, the ratio of the column diameter to the resin bed height can be greater in the large columns.

Second, it is possible to use smaller liquid volumes relative to the bed volume. For example, in the smaller, previously-described columns a minimum of 2 bed volumes could be aspirated. But in the larger columns, it is possible to aspirate one bed volume of liquid.

Furthermore, higher flow rates can be used with the larger columns. Columns that have a body size of at least 2 mL and a bed volume in the range of 200 µL to 50 mL can be operated using significantly faster flow rates than columns having a smaller column body and bed volume. Flow rates in the range 1 mL/min to 12 mL/min and faster can be used. In large column embodiments, the flow rate for passing liquids through the column can be within a range having a lower limit of 0.5 mL/min, 1 mL/min, 1.5 mL/min, 2 mL/min, 2.5 mL/min, 3 mL/min, 3.5 mL/min, 4 mL/min, 4.5 mL/min, 5 mL/min, 6.5 mL/min, 7 mL/min, 7.5 mL/min, 8 mL/min, 8.5 mL/min, 9 mL/min, 9.5 mL/min, 10 mL/min, 10.5 mL/min, 11 mL/min, 11.5 mL/min, 12 mL/min or greater. The upper limit of the flow rate can be in the range of 60 mL/min, 70 mL/min, 80 mL/min, 90 mL/min, 95 mL/min or 100 mL/min.

As a result of the higher flow rates, the separation times are shorter and cells can be isolated and recovered in a very short time. In some embodiments, cells can be isolated from a biological sample in less than 45 minutes, less than 30 minutes, less than 25 minutes, less than 20 minutes, less than 15 minutes, less than 10 minutes or even less than 5 minutes.

On-Column Lysis or Interrogation

In certain embodiments, the cells are not eluted but instead are manipulated or interrogated on the column. The cells can be labeled on column, for example with a fluorescent antibody or aptamer. Cells can be lysed on column and cell components (e.g., nucleic acids) can be eluted and analyzed.

In some embodiments, the cells are not eluted from the column. Instead the cells may be studied or used while on the column. The cells can be lysed on column or the column bed material with cells bound can be released from the column and subjected to further analysis such as a polymerase chain reaction. Nucleic acids, DNA or RNA associated within with the cells or that have bound to the cells or released from the cells may be measured.

In some cases it is desirable to label cells on the column for instance with an antibody, fluorescent tag or aptamer. On-column labeling can be useful for diagnostic applications by enhancing the signal to noise ratio.

In some embodiments, the columns of the invention can be used to distinguish live and dead cells. Reagents sold by Life Technologies and others can be useful for these methods.

On column lysis can be done slowly and with large volumes of lysis solution so that the column is not plugged.

Cell Therapy

The invention additionally includes devices and methods for treating diseases. In some embodiments, healthy cells can be transferred between organisms. For example, donor cells from a healthy pancreas can be isolated on a column and transplanted into a patient suffering from Type 1 Diabetes. Stem cells are used for bone marrow transplantation will likely have a variety of therapeutic applications in the future.

Stem cells and other cells may be captured, purified with packed bed column technology in an open system or a sealed system and then manipulated using CRISPR type genome editing methodologies and technologies. The cells may be collected for further downstream processing.

Crispr technology uses the cas9 enzyme with a guide RNA sequence to cleave and edit the genome at specific site while in the cell. This technology allows the researcher to specifically cut and insert/edit the genes at will. One of the major applications for this is gene therapy. Disease caused by one gene error can be fixed using Crispr to fix the gene to cure the disease. Another application is the manipulation of stem cells or early stage cells. Defective genes may be edited to control or eliminate disease or other genetic factors.

There are many research applications. Knock out organisms (knock out mice) can be created to facilitate researching genetic pathways. Similar knock out work can be performed with cell lines to create for example cell lines that function to perform specific things. You can create different strains of plants can be created by changing/editing the genes to create resistant strains, more fertile strains or strains with specific attributes.

Editing of the cells with Crispr technology may be performed while the cells are captured on columns of the invention or after they have been eluted and recovered from a column of the invention.

Samples containing donor cells can be obtained from a variety of sources including human, animal and cell culture. For example, donor cells can be obtained from cell culture, body fluids such as blood or lymph, organ tissue, bone marrow, etc. Donor cells can be engineered cells.

In other embodiments, cells are used to deliver gene therapies. Genes can be introduced into cells for example, by using a replication-defective adenovirus to produce engineered cells. These cells can perform a variety of therapeutic tasks such as delivering drugs, destroying cancer or regulating the immune system.

In one study, T cells were engineered to produce antibodies that bind cancerous cells (Grupp et al., N Engl J Med. 2013 Apr. 18; 368(16):1509-18). These engineered T cells were introduced into patients with leukemia to achieve remission or tumor size reduction. In this type of application, patients' T cells could be isolated using a column of the invention, engineered and then proliferated in cell culture. After the engineered T cells were grown, they could be isolated with a sterile column prior to introduction into a patient.

The columns and methods of the invention can be used to isolate cells used for cell-based therapy. In these embodiments, sterile columns can be used for cell isolation. One advantage to this approach is that the cell populations obtained will be free of contaminants. In certain embodiments, cells isolated from columns are administered to patients to treat diseases such as cancer, diabetes, heart disease, Parkinson's, Alzheimer's, liver disease and others. Healthy cells can be used to replace cells in damaged or diseased organs. Cells isolated from any source can also be transferred to a different individual or organism. For instance, cells can be transferred to a mouse or other animal model for research, diagnostic, characterization or medical purposes.

Organ Cells on a Column.

Cells isolated from any source can also be transferred to a different individual or organism and contained on a column. Cells contained in columns and the products from columns may be used for research and medical purposes. They may be interrogated chromatographically to determine what interacts with the cells and the manner in which they interact. These experiments may be performed in parallel or serially. The effects on the cells may be studied. The biological products released from the cells may be used for research and medical purposes.

Columns containing captured cells of specific organs can be used for drug testing. For example a column containing liver cells can be used to study the interactions and the effects these interactions of drug candidates with liver cells infected with hepatitis B, a viral infection of the liver.

Columns of the invention can capture kidney cells, intestine cells, muscle, cells, fat cells, bone cells, skin cells, pancreas cells, blood vein cells, etc. Furthermore, columns containing different organ cells can be studied together. For example, a drug candidate designed to interact with prostate cells might also interact with liver cells in such a way that might produce toxic products. The flow from columns may be collected and analyzed with mass spectrometry, infrared spectrometry, UV spectrometry or other analytical tools. Columns of the invention containing for example, parotid gland cells of the mouth or Eccrine sweat gland cells of the skin can be used to measure the interaction of several molecules. These molecules can be contacted with columns of the invention containing other cells such as liver cells, or kidney cells for example and the interactions and effect of interactions measured. The fluid that is pumped through the column or columns of the invention can be blood-mimicking fluids which bring sustenance to the cells.

Columns of the invention may be used to capture human induced pluripotent stem cells, adult stem cells that are treated to become embryonic state and then encouraged to become many different types of tissue. The use of stem cells on columns of the invention can be used to represent an individual. In this way, columns representing various organs could be derived from a single person. Or cells obtained from a biopsy from an individual can be captured onto columns of the invention. Experiments could then be carried out on the various columns to determine the interactions and effect of interaction of drugs at various concentrations or amounts (dosages), or combinations of drugs at various ratios, concentrations or amounts.

Therapeutics Screening

Columns and methods of the invention can be used to screen drug leads and identify drug targets. Disease cells can be immobilized on the column medium and challenged with pools of drug candidates such as small molecules, engineered proteins (such as engineered T-cell receptors), biologics or other entities. The column can be washed to remove species not tightly bound.

At this stage, the cells bound to drug candidates can be interrogated. Different solvent conditions can be applied to the column to test binding and dissociation conditions. Alternatively, cells bound to a drug candidate or other entity can be released from the column and studied. For example, cells can be disrupted to create membrane fragments consisting of cell surface components bound to drug targets. The drug targets and the drug leads can be identified using methods such as mass spectrometry.

Alternatively, drug candidates can be immobilized on a column and different cell types can be passed through the column to identify and then characterize interaction. In some embodiments, cells can be manipulated prior to passing them through the column. For example, cells can be mixed with a drug candidate and subjected to competition experiments with other drug candidates present on the column.

Cell Clean-Up

The columns and methods described herein can additionally be used for cell clean-up. For instance, it can be desirable to separate cells from contaminants, collect materials from cell populations or perform buffer exchange. Existing methods for cell clean-up include magnetic beads, dialysis and centrifugation which are time-consuming, single equilibrium procedures. The columns and methods of the invention provide a rapid alternative and offer the advantage of being a multi-equilibrium process.

In some embodiments, cells are purified away from contaminants by capturing contaminants on the column while cells pass through unencumbered. Contaminants can be captured on the solid phase using for example, an affinity group, aptamer capture, ion exchange or other strategies. Alternatively, size exclusion can be used to separate cells from contaminants. Using size exclusion, cells might pass through the column quickly while smaller contaminating molecules might enter the solid phase which would cause them to pass through the column more slowly.

Diagnostics

Some requirements of a good diagnostic procedure are that it is rapid, simple, enriches the sample before detection, removes nonspecific materials (that could give a signal), high sensitivity, high signal to noise, and linear signal.

The columns and methods of the invention can be used for a number of diagnostic applications including oncology, virology and infectious diseases. Diagnostic applications include isolation of any cell type and the option of additional cell characterization on column or post column. One application is the identification of pathogens such as viruses, bacteria, fungi and protozoa from a patient sample. Another application is the isolation and characterization of cancer cells, such as circulating tumor cells (CTCs) as described below in Example 3. Isolation of CTCs is useful for early cancer detection, characterization of tumor cells, monitoring disease treatment, monitoring progression or remission.

Diagnostic applications of the invention can be used in a variety of settings. In certain embodiments, diagnostics are utilized in a research setting such as academia, biotechnology or pharmaceutical company. In other embodiments, the columns and methods of the invention can be used in point of care settings including emergency rooms, intensive-care units, patients' bedsides, physician's offices, pharmacies and blood banks. In still other embodiments, diagnostic applications can comprise in-home tests. Diagnostics are also useful in a corporate setting such as the food industry.

Diagnostic target cells can be any cell type listed above. As described above, cells are not defined herein as limited to entities capable of self-replication. Included in the definition of cells are viruses, parasites and exosomes and organelles. A non-limiting list of diagnostic targets include mammalian cells, human cells, cancer cells, circulating tumor cells, viruses, bacteria fungi and parasites. A non-limiting list follows: *Shigella, Salmonella, E. coli, Helicobacter pylori, Campylobacter, Chlamydia, Gonococcus, Streptococcus, Staphylococcus, Mycoplasma, Trichomonas vaginalis, Clostridium botulinum*, HIV, Hepatitis A, B and C, Herpes, Amoeba/parasites, *Entamoeba histolytica, Acanthamoeba* and *Naegleria, Cryptosporidium, Giardia*, Fungi such as Coccidiodomycosis (Valley Fever), blastomycosis, histoplasmosis, yeast—*Candida albicans* and other *Candida* sp. (hospital infections, blood infections) and opportunistic pathogens such as Cryptococcosis and Aspergillosis.

Although it is not required for all diagnostic applications, a label can be employed. For example, cells can be captured and then labelled on the column. Alternatively, cells can be labelled prior to column capture. When cells are labelled prior to capture, the label can aid in cell capture. In some embodiments, the label can actually be the entity captured on the column. Labelled cells captured on the column can be washed, eluted and a detection step performed. In another embodiment, cells can be labelled following elution from the column. An advantage to this approach is that a homogeneous cell population can be obtained prior to the labelling step.

In some embodiments, only a few or relatively few of a particular cell surface markers are used to capture a cell on the medium. For this example, we will call these markers Type A. This leaves most of the captured cell markers Type A on the rest of the cell untouched. The labeling of a cell can be performed by reacting these remaining, excess Type A cell markers. In other embodiments, the labeling of a cell is performed by reacting a cell marker, Type B, which is not used for capturing the cell on the column. This strategy is especially useful for on-column tagging or labelling of the cells. By targeting a different cell marker for labeling, the cell is less likely to be removed or eluted in the tagging process.

In some embodiments, the tagged cells are eluted and then detected. In some embodiments, the elution of the tagged cell is performed by changing the chemical nature of the linking or capture reagent.

A label is defined herein as any entity that can aid detection. A variety of labels can be used for this purpose. For example a fluorescent dye-labelled antibody or Fab can be used. In addition, an antibody or Fab can be conjugated with any kind of tag that aids detection. In addition to dyes, non-limiting examples of tags include radioactive labels, proteins, enzymes (e.g., horse radish peroxidase), and metals including rare earth metals. Labels are not limited to tagged antibodies or Fabs; they include anything that can bind the cell surface such as a protein, a dye or other molecule.

Dye-labelled antibodies or Fabs can be used to label specific cell surface markers and viable versus dead cells. Dyes used to label proteins include Ellman's Reagent, Coomassie Blue, Lowry reagents and Sanger's reagent.

Post-column label detection can be carried out using a number of different methods. For instance, detection can be done with flow cytometry, a microscopy, a spectrophotometry, mass spectrometry, a colorimetric reader, a protein assay or a nucleic acid assay.

In alternate embodiments, on-column detection can be utilized. On-column detection can be performed for example, by reflectance (UV or visible), fluorescence, colorimetric detection (e.g., ELISA), chemiluminescence and others.

Cell-Based Stationary Phase for Liquid Chromatography

Columns of the invention can be used to produce and use a stationary phase comprised of cells, referred to herein as the cell-based stationary phase. The cells can be attached to a substrate and used to measure the interaction of analytes with a cell-based stationary phase. The cell stationary phase may be comprised of live or active cells. Active is defined herein as a cell that is not only living, but can undergo biological processes while attached to the column medium. Samples are injected into the mobile phase and enter the column and interact with the cell-based stationary phase. These interactions can be identified and quantified. Retention data and column interaction data can be collected and analyzed. In many cases, the liquid phase flow through the column is unidirectional however, in some cases, bi-directional flow may be employed.

Generally, cells that are placed on the cell-based stationary phase are viable however, it is not mandatory. Cells attached to affinity resins packed into a chromatographic bed have surface groups of various types that can interact with analytes flowing through the column. These groups include proteins including glycoproteins, carbohydrates, lipids, sugars and other groups. The proteins may contain phosphate groups, glycans, etc. Analytes such as drug candidates or antibody-drug conjugates can interact with these groups by pumping them or injecting them into a liquid phase flowing through columns. Examples of interactive entities include antibodies (e.g. from antibody libraries), antibody-drug conjugates, FABS, proteins, enzymes, sugars, nucleic acids, lipids, ion exchange and other groups. This interaction can be measured in different ways, depending on how the chromatography is performed and the kinetic rate constants of the on/off interaction of the cells with the stationary phase. Properties of the cells can be analyzed after they are removed from the column. For example, cells can be removed from the column after chromatography to measure chemical properties of the cells. They can be stained to count the numbers of live cells and dead cells.

The types of substrate used to form the cell-based stationary phase include affinity, ion exchange resins and others. In fact, any chemistry directed to cell surface markers can be used.

With living cell stationary phase chromatography, the types of interaction of an analyte with the cell stationary phase can be characterized. Types of measurement include the kinetics of interaction, the extent or magnitude of interaction, the relative selectivity of the interaction and other parameters. The column may be used to separate analyte materials that have different selectivity. For example, two different analyte materials may be associated or bound to a stationary phase. An eluent may be added to the column and one material may be removed from the column faster or more easily than the second material. This difference in selectivity may be measured.

In one example, cell chromatography may be used to determine which reagents interact with stem cells and the effect of that interaction on the cells. Stem cells are loaded onto a column to make a living cell stationary phase. Then, various analytes are introduced into the column under controlled chemical and physical conditions. The experiments may be performed in parallel. Using chromatography, it can be determined the extent of interaction of a reagent with the stationary phase and how the interaction can be controlled. The relative affinity of two or more analytes can be measured. Then after the chromatography is performed, the cells may be eluted and analyzed to determine the effect of the interaction on the stem cells.

Chromatography with a living cell stationary phase may be used to examine interaction of a particular type of cell and drug candidates. Cancer cells from a particular patient may be loaded onto a column. Existing drugs may be introduced into the column and the chromatographic interaction measured to determine if a particular drug, series of drugs or a mixture of drugs may be suitable for treatment of the patient. After exposure and chromatography measurement of the analytes, the cells can be removed and analyzed to determine the effect.

The cells are preferably living and stable in flowing fluid through the column. The cells are not sheared from the column beads or media by the stream of liquid flowing through the column. The cells remain alive while attached to the column and remain available for use as a liquid chromatographic stationary phase for at least 30 min, at least 1 hr, at least 2 hrs, at least at least 3 hrs, at least 4 hrs, at least 5 hrs, at least 6 hrs, at least 12 hrs, at least 1 day, at least 2 days, at least 3 days, at least 4 days, at least 5 days, at least 6 days or even longer.

Analytes of various types are introduced to the column of the invention with a mobile phase fluid flowing through the column. The analytes interact with the cell stationary phase to different extents depending on the kinetics and selectivity of stationary phase to the analyte. The extent of interaction is measured with individual analytes or under competitive conditions with two or more analytes in a matrix of background conditions. In addition, analyte materials of interest may interact with the cell stationary phase and be captured or removed from a complex matrix solution.

There are two general methods to prepare the system for capture of the cells by the column. In one method, the column medium contains sites that interact with the surface of the target cells. The medium may have the sites or may be conditioned to gain the sites that interact with the columns. An example of this is where the column contains nucleic acids, lipids, peptides, antibodies or Fabs that can capture cells through surface markers. In another example, the column contains chelating or ion exchange sites which can interact directly with a cell or may contain a reagent that interacts with cells. In another example, the column contains aptamer sites that interact with the surface of the cells.

Another method may be to treat the cells with antibodies or other reagent(s) that allow the cells to bind the column medium. For example, antibodies can interact with cells in solution. The cells attached to antibodies can be captured by a Protein A or Protein G column. In another example, each antibody molecule may contain another functional group such as a biotin. The biotin entity on the antibody (which is attached to the cell) may be captured by a streptavidin resin in the column.

Different protocols may be used to capture cells for purification. In one embodiment, the resin bead is activated or may be activated with an entity to be able to capture cells. After activation, a sample may be processed to capture the cells in the first step of purification. In another embodiment, cells may be treated or activated and then captured by flow cells through the column.

In order to produce the cell stationary phase columns, the column and substrate must have the same cell accessibility characteristics as columns used to capture and purify cells. That is, the cells are accessible to chemical interactions. Cells are not trapped in dead spaces and cells are not damaged by the frits or resin. The cell stationary phase columns are characterized by low backpressure, low dead volume, and very little dead space.

In one procedure, the cells are attached to the surface of the column packing resin and then the resin containing the cell stationary phase is packed into a column. The cells can be attached to the resin substrate in a slurry. This attachment step can also be accomplished in two ways. The cells may be activated with an antibody or other chemical entity that in turn, can attach to the resin. Or, the resin substrate may be activated with an antibody or other chemical entity that can in turn, allow attachment of the cells. The cells are then mixed with the resin and the cells attach to the substrate producing the cell stationary phase. Once the cell stationary phase is produced, the resin is packed into the column.

Resins can be activated to be able to capture cells to make a cell stationary phase. One example of this is to load an antibody onto Protein A column resin beads. The antibody is selective for surface proteins on the cells. Alternatively, cells can be activated to be able to attach to resin beads. An example of this approach is the attachment of a His-tagged Fab to cells. After removing excess Fab material by centrifugation, the cells can be introduced to an IMAC resin bead. The cells attach to the beads through the His-tagged Fab.

A resin substrate (not containing the cells) is packed into a column. The resin bead substrate contains an affinity group that can capture cells. The cells are introduced into the column and the cells attach to the substrate producing the cell stationary phase. This capture step can be accomplished in several ways. For example, the cells may be activated with an antibody, aptamer or other chemical entity that in turn, can attach to the resin. In another method, the resin substrate may be activated with an antibody or other chemical entity that can in turn, attach the cells.

In one example, a column was prepared by gluing a frit on one end, packing the column and then gluing a second frit on the top of the column. A 37-micron pore, 60 micron thick Nitex screen frit was attached to the end of an acrylic tube 0.750 inches long, 0.500 inch outer diameter and 0.375 inch inner diameter. Packing was accomplished by standing the column on a stand with deep-well plate beneath the column that allowed liquid to flow out of the lower end. An aqueous slurry of agarose resin, 45-165 micron particle size, was transferred to the column by pipette. The packing material was not compressed. Excess liquid drained away filling the column with resin. Additional slurry was added until the bed of the column reached the top of the column. A Nitex screen of the same material used for the other frit was glued onto the column end using a methylene chloride solvent.

Silicone tape was wrapped round the column to increase the diameter. Then, two 10 mL plastic syringe bodies and male luer connections were cut to the 1 mL volume mark and placed on the end of the column. The column body was wrapped with stretchable silicone tape to seal the column body. Male luer connections were connected to the inside of clear flexible Tygon tubing 0.250 inch outer diameter to connect to the injector and fraction collector.

Figure 7:
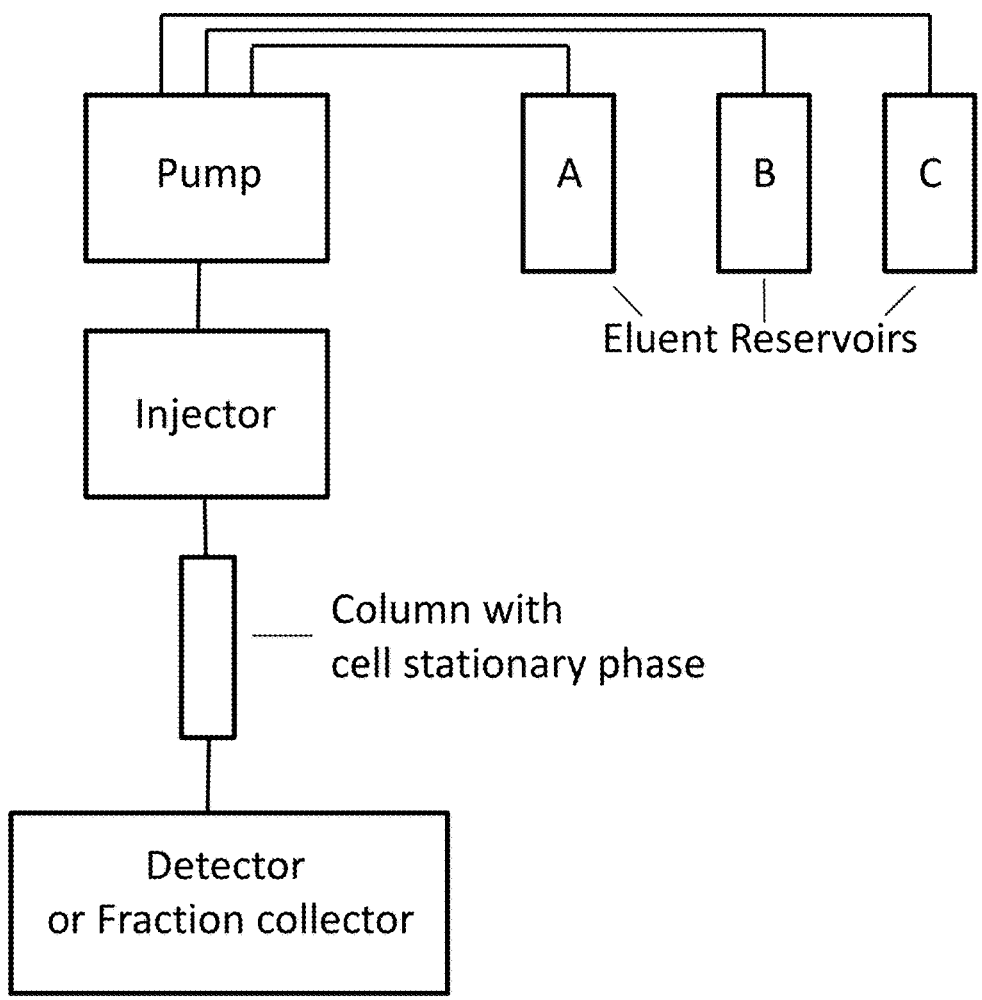
FIG. 7 is a depiction of one embodiment of a column having a cell stationary phase in a chromatographic system.
Figure 8:
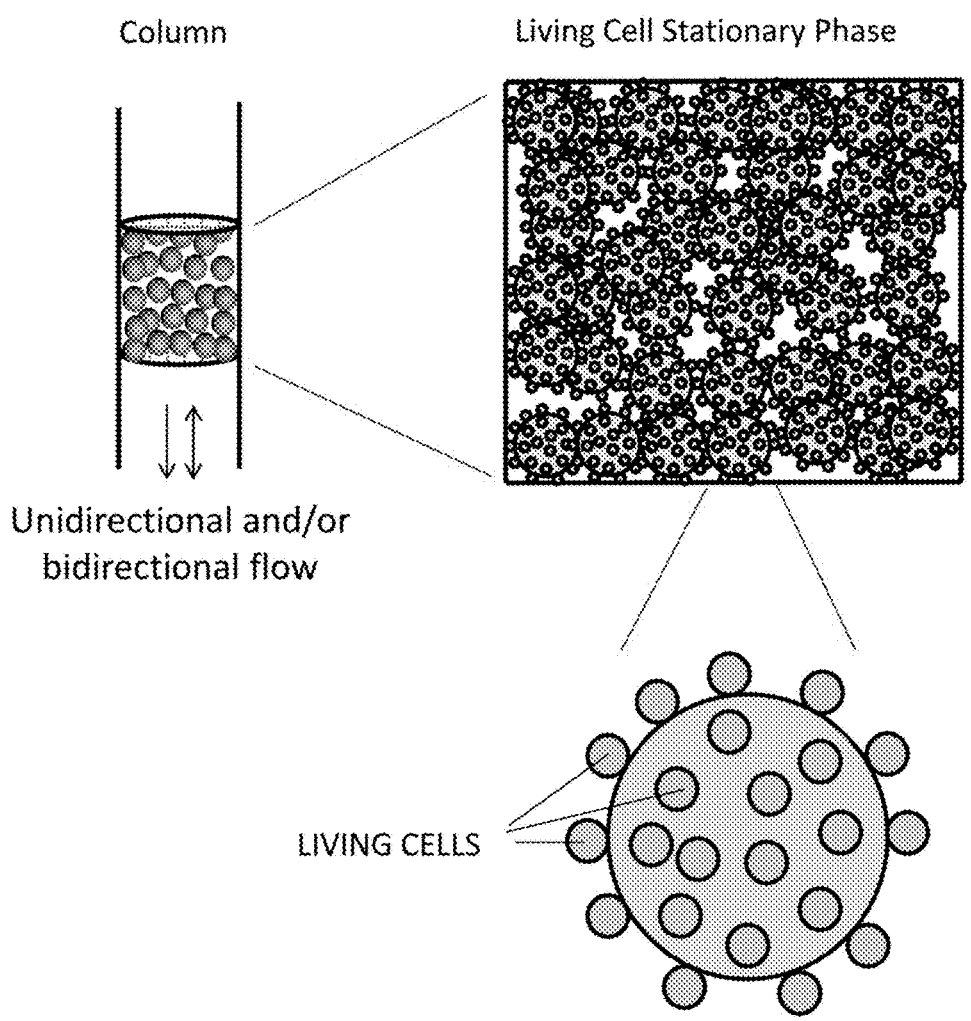
FIG. 8 is depiction of how cells are located on the surface of beads that are packed into a column to form cell stationary phase column.

In a second example, the cells are attached to the column. A His-tagged Fab is pumped through the column loading the column completely with the Fab. The Fab is selective for a surface protein on the HeLa cancer cell line. After washing the column, HeLa cells are pumped into the column loading cells onto the surface of the stationary phase. The column now contains a HeLa cell-based stationary phase. A chromatographic column in a chromatographic system is shown in FIG. 7. A column comprised of a cell stationary phase is shown in FIG. 8.

Once the cell stationary phase column is prepared, chromatography can be performed. Cells captured on the column can be interrogated with groups of compounds or analytes to identify those that bind cells with the desired affinity. For instance, a library of compounds can be added to the column to determine which materials in the library have an affinity for the cells on the column. The sample containing the library is added to the column. The column can be washed. The stringency of the wash may be varied to control capture of library materials. Then, the column can be washed at high stringency to elute the compounds or the cells with compounds attached.

Analysis to determine the identity of the compounds may be performed with mass spectrometry. The identity and concentration of the compounds recovered may be determined by liquid chromatography or mass spectrometry methods. The concentration of the various compounds may indicate the ability of the cells to capture a particular compound.

The interaction of different materials with the stationary phase is measured using various chromatographic techniques. The extent of interaction under different conditions may be measured. The identity of materials interacting may be determined. The ability of a reagent to bind to the cell may be measured. This measurement may be performed relative to an eluent reagent or may be performed relative to another analyte reagent.

The type of chromatography that can be performed depends on the kinetic rates of the analyte interaction with the cell stationary phase. For rapid kinetic interaction of analytes with the column, partitioning chromatography may be performed. Partitioning chromatography is performed using unidirectional flow. Measurement of the analyte interactions may performed using retention times or related values such as capacity factors. Partitioning chromatography is performed under isocratic and gradual gradient conditions.

Other types of chromatography that may be performed with rapid analyte kinetic interaction with the cell stationary phase include step gradient chromatography, displacement chromatography and frontal/breakthrough curve chromatography. Step gradient and displacement chromatography can be performed with either bidirectional or unidirectional flow. Frontal/breakthrough curve chromatography is performed with unidirectional flow.

For slower analyte kinetic rates of interaction with the cell stationary phase, step gradient chromatography, displacement chromatography or frontal/breakthrough curve chromatography can be employed. Also in these cases, step gradient and displacement chromatography can be performed with either bidirectional or unidirectional flow. The step gradient may be one step gradient, after an optional wash or multi step gradient. Frontal/breakthrough curve chromatography is performed with unidirectional flow.

Some interactions may be additive. For example, calcium may be added to membrane channels. In this case, the kinetic rate of uptake would be higher than release and breakthrough curve measurement may be more appropriate.

Partitioning chromatography may require an injection of a slug of analyte into a flowing eluent stream, provided the partitioning is rapid. But large injection volumes can be employed if the selectivity of the analyte for the column is high. Breakthrough chromatography requires a continuous uniform (injection) supply of analyte. Injection is at the top or inlet of the column for partitioning or gradual gradient chromatography. Displacement chromatography generally requires a large injection ensuring that the stationary groups are displaced with the eluent. Injection can be at the top of the column or at the bottom of the column for back and forth flow.

The following steps are an example of a partitioning chromatographic procedure using living cell stationary phase column.
1. Treat or activate column or cells to provide suitable conditions for the column media to be able to capture cells.
2. Load cells onto column from a flowing stream. Loading may be performed in a unidirectional or bidirectional mode.
3. Wash nonspecific bound materials from the column using a flowing stream.
4. Pump an eluent through the column and through the detector to ensure that all material has been washed from the column and a stable detection baseline is achieved.
5. Inject a single or mixture of analytes into the column.
6. Pump an eluent solution through the column and measure retention of analyte or analytes.
7. Optionally recover cells from column stationary phase after exposure to analytes and analyze.
8. Optionally lyse cells or elute the components of the cells for analysis. The lysis step may be done partially, or over a long time period using gentle conditions to remove components of the cell for processing and/or analysis.
9. Remove and recover cells for analysis of the cells and/or further research and development processing.

Detection may be continuous or fractions may be collected and analyzed. Analyte measurements include retention time, capacity factor, selectivity coefficient and others.

The bidirectional flow step gradient and displacement chromatography can be can be performed with the pipette, syringe, gas pressure/vacuum chamber, peristaltic pumps and living cell stationary phase columns of the invention. This type of chromatography can be operated with a manual or electronic controlled pipette or automated robotic liquid handler operated as a single channel or multiple columns in parallel or up to 96 channels are operated in parallel.

The following steps are an example of gradient chromatographic procedure using living cell stationary phase column.
1. Treat or activate column or cells to provide suitable conditions for the column media to be able to capture cells.
2. Load cells onto column from a flowing stream. Loading may be performed in a unidirectional or bidirectional mode
3. Wash nonspecific bound materials from the column using a flowing stream.
4. Pump an eluent through the column and through the detector to ensure that all material has been washed from the column and a stable detection baseline is achieved.
5. Pump a library mixture of analytes into the column.
6. Wash the column with an eluent to remove all excess non-attached analytes.
7. Optionally recover cells with analytes attached and analyze.
8. Optionally remove analytes from column with step gradient eluent solution. Recover, detect and analyze the analytes.
9. Optionally remove analytes from column with continuous gradient eluent solution. Recover, detect and analyze the analytes.
10. Optionally recover cells from column stationary phase after exposure to analytes and analyze.
11. Optionally lyse cells or elute the components of the cells for analysis. The lysis step may be done partially, or over a long time period using gentle conditions to remove components of the cell for processing and/or analysis.
12. Remove and recover cells for analysis of the cells and/or further research and development processing.

For slow kinetic interactions, the mobile phase flow rate and the linear flow velocity may be adjusted (lower) if necessary to compensate for the slower kinetic rates. These adjustments are options for all of the various types of chromatography.

The following steps are an example of displacement chromatographic procedure using living cell stationary phase column.
1. Treat or activate column or cells to provide suitable conditions for the column media to be able to capture cells.
2. Load cells onto column from a flowing stream. Loading may be performed in a unidirectional or bidirectional mode
3. Wash nonspecific bound materials from the column using a flowing stream.
4. Pump an eluent through the column and through the detector to ensure that all material has been washed from the column and a stable detection baseline is achieved.
5. Pump and capture analytes on the sites of the cells in the column.
6. Wash the column with an eluent to remove all excess non-attached analytes.
7. Introduce a second analyte and measure displacement of first analyte from column.
8. Optionally remove analytes from column with eluent solution. Recover and analyze the analytes.
9. Optionally recover cells from column stationary phase after exposure to analytes and analyze.
10. Optionally lyse cells or elute the components of the cells for analysis. The lysis step may be done partially, or over a long time period using gentle conditions to remove components of the cell for processing and/or analysis.
11. Remove and recover cells for analysis of the cells and/or further research and development processing.

Figure 9:
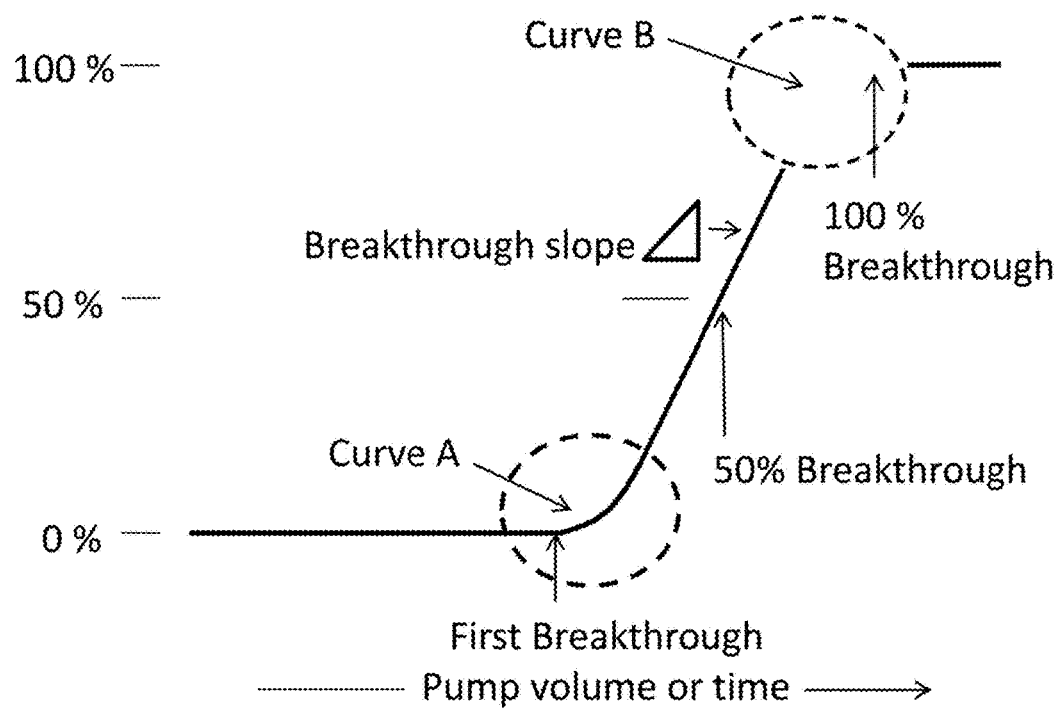
FIG. 9 shows the features of a curve obtained from breakthrough chromatography.

The geometry of a breakthrough curve is depicted in FIG. 9. The x-axis denotes the time the analyte is pumped or the volume of the analyte pumped. The y-axis shows the amount of analyte that exits the column relative the column input concentration. To start, analyte is pumped through the column and is taken up by the stationary phase. The first breakthrough is where the analyte is not completely taken up from the column. The curvature of slope A is an indication how fast the analyte is taken up by the stationary phase. A long extended slope of curve A indicates a slow on-rate of the analyte. The slope of the breakthrough is an indication of the kinetics of uptake and release and of how the column is packed. An ideal breakthrough is vertical, but in practice, all breakthrough curves have a slope. The 50% breakthrough point shows how much analyte is taken up by the column. This is calculated by multiplying the volume at which 50% breakthrough occurs by the concentration of the analyte being pumped through the column. Curve B is the curve leading into the point at which no analyte is being taken up by the column, 100% breakthrough. A long extended curve at this point indicates a slow off-rate and/or a slow on-rate of the analyte.

Competing materials can be added while performing breakthrough chromatography. Generally, small-diameter beads packed in columns with low dead volume will give breakthrough curves with steeper slopes. In these cases, the mass transfer and diffusion to the surface of the bead are decreased so that the kinetic interaction and the extent of interaction can be measured.

The following steps are an example of breakthrough chromatographic procedure using living cell stationary phase column.
1. Treat or activate column or cells to provide suitable conditions for the column media to be able to capture cells.
2. Load cells onto column from a flowing stream. Loading may be performed in a unidirectional or bidirectional mode
3. Wash nonspecific bound materials from the column using a flowing stream.
4. Pump an eluent through the column and through the detector to ensure that all material has been washed from the column and a stable detection baseline is achieved.
5. Pump an analyte into the column. The breakthrough of the analyte is measured by the initial breakthrough, shape and slope of the breakthrough, 50% breakthrough point and the shape of the slope to analyte plateau.
6. Optionally recover cell with analyte attached and analyze.
7. Optionally remove analyte with eluent solution. Monitor and analyze the removal of the analyte from the cell stationary phase.
8. Optionally recover cell after exposure to analyte and analyze.
9. Optionally repeat with a second analyte. Pump a second analyte through the column and measure breakthrough parameters. Measure the difference of selectivity cell stationary phase column of first and second analyte.
10. Optionally, repeat with several other analytes and measure the difference in selectivity of the different analytes.

Breakthrough curves measure effective capacity for a particular analyte, the kinetics of on interaction and the kinetics of off interaction. Analyte measurements include slope, starting and ending breakthrough shape, the breakthrough plateau shape and other parameters. Competing analyte materials can be combined while performing breakthrough chromatography.

When the analytes are dyes that bind to specific cell surface proteins, breakthrough curves can also be used to measure the expression of cell surface proteins. Proteins expressed on the surface of mammalian cells are often universal. Disease cells may express cell surface proteins in concentrations that are different from non-disease cells. In addition the ratio of one cell surface proteins to another cell surface protein has been shown to be different when comparing diseased versus non-diseased cells. This information can be used to either design new therapeutics directed at detecting the stoichiometry of cell surface proteins, guide the administration of drug cocktails to individual patients, and to diagnose disease.

In the columns and methods of the invention, cells can be captured from rapidly flowing streams. As an example, for columns having diameters ranging from 2 mm-4 mm, capture can be from cells moving through the column at 0.05-20 mm/sec, 0.1-10 mm/sec, 0.2-5 mm/sec, 0.3-3 mm/sec, 0.4-2 mm/sec and 0.5-1 mm/sec. The linear velocity at 0.1-10 mm/sec corresponds to absolute flow rates of about 100 μL/min to 10 mL/min respectively. For columns with diameters ranging from 4 mm-4 mm, capture can be performed from cells moving through the column at 0.05-20 mm/sec, 0.1-10 mm/sec, 0.2-5 mm/sec, 0.3-3 mm/sec, 0.4-2 mm/sec and 0.5-1 mm/sec. The linear velocity at 0.1-10 mm/sec corresponds to absolute flow rates of about 500 μL/min to 5 mL/min respectively. For columns with diameters ranging from 10 mm-15 mm, capture is from cells moving through the column at 0.05-20 mm/sec, 0.1-10 mm/sec, 0.2-5 mm/sec, 0.3-3 mm/sec, 0.4-2 mm/sec and 0.5-1 mm/sec. For these columns, linear velocity at 0.1-10 mm/sec corresponds to absolute flow rates of about 1 mL/min to 100 mL/min respectively. As yet another example, for column with diameters ranging from 15 mm-40 mm, capture is from cells moving through the column at 0.05-20 mm/sec, 0.1-10 mm/sec, 0.2-5 mm/sec, 0.3-3 mm/sec, 0.4-2 mm/sec and 0.5-1 mm/sec. For these columns, linear velocity at 0.1-10 mm/sec corresponds to absolute flow rates of 5 mL/min to 500 mL/min respectively.

The following steps are an example of a chromatographic procedure for purification of cells for recovery and detection.
1. Treat or activate column or cells to make the column suitable to be able to capture cells.
2. Load cells onto column from a flowing stream.
3. Wash non-specific bound materials from the column using a flowing stream.
4. Optionally tag cells with a reagent that reacts with a group on the surface of the cell. The tag reaches with an attachment group or entity that is optional different than the attachment group used to capture the cell to the column.
5. Optionally measure cells with the cells attached to the column. Optional detectors are infrared, surface and transmission VIS/UV, fluorescence, chemiluminescence spectrophotometers.
6. Optionally lyse cells or elute the components of the cells for analysis. The lysing may be done partially, or over a long time period using gentle conditions to remove components of the cell for processing and/or analysis.
7. Remove and recover cells for analysis of the cells and/or further R&D processing, growing or transforming of the cells or further research and development and/or therapeutic use of the cells.

Figure 10:
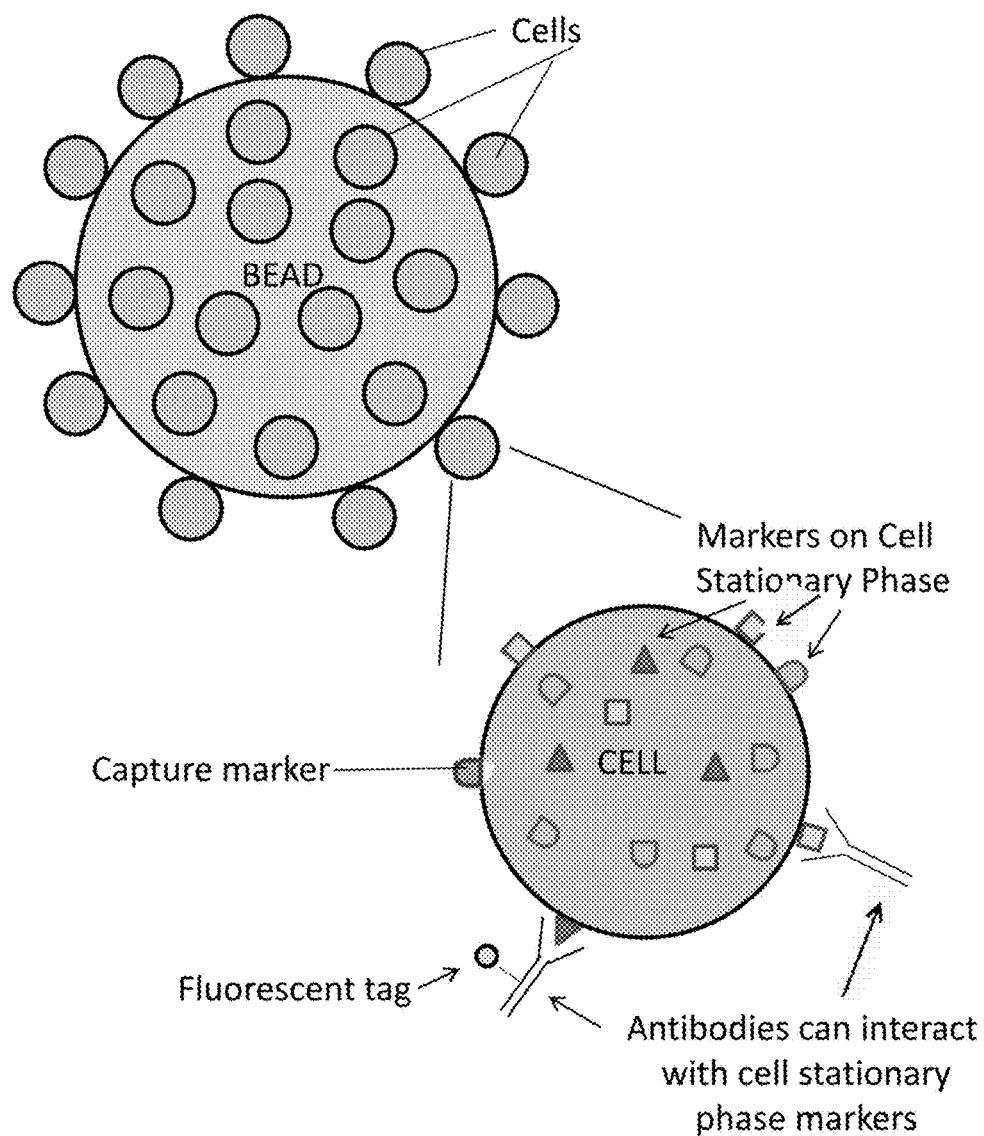
FIG. 10 is a depiction of the different markers on the cell surface. These cell markers can interact with antibody analytes for cell purification or forming a cell stationary phase. They can interact with a fluorescent tagged antibody. Cell markers may interact with analytes.

Cell surface markers are used in a number of ways in columns and methods of the invention as shown in FIG. 10. In some embodiments, cell markers are used to capture the cell to the bead for capture or to form a cell stationary phase. Other markers may be used to tagging the cells. This can be performed on the column or post column recover. Other markers are the basis for interaction of analytes with the cell stationary phase. In some embodiments, different markers are used for different purposes as shown in FIG. 10. For example, a different marker may be used for on column tagging the cell than the marker used for attaching the cell to the bead. In this way, the so that the cell. In this way, the tagging process is less likely to interfere with the attachment of the cell. Similar strategies are used for cell stationary phase experiments.

Figure 11:
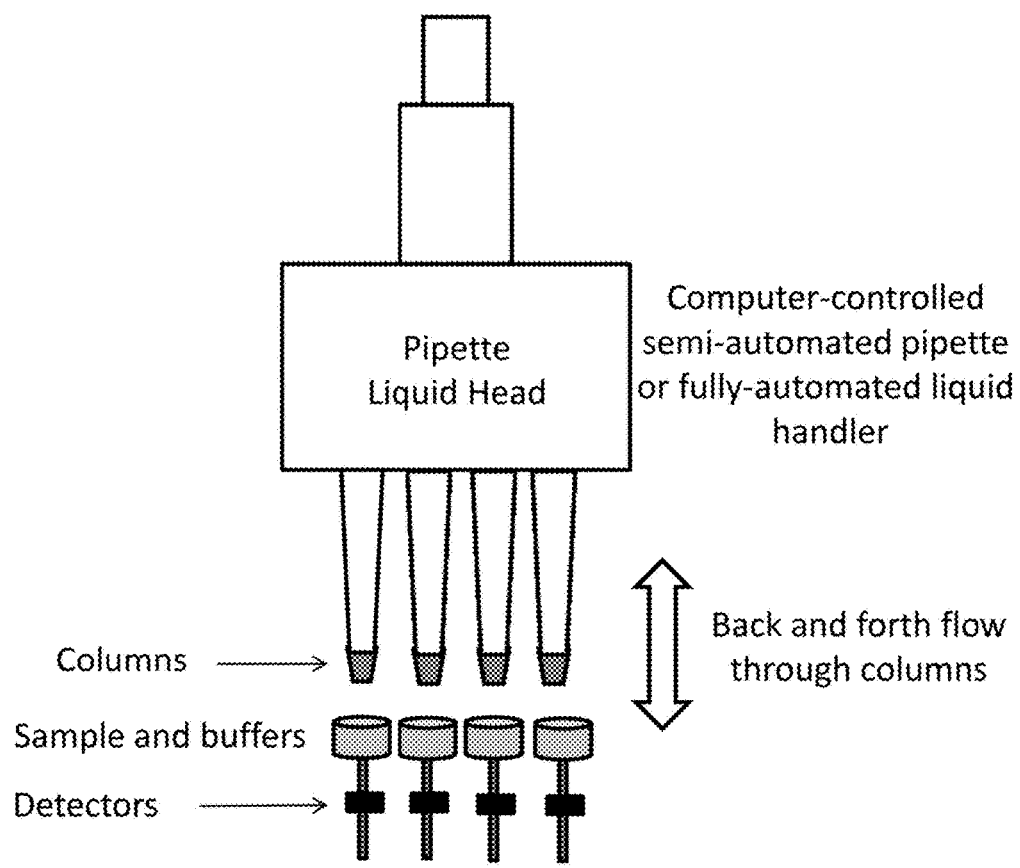
FIG. 11 is a depiction of a pipette tip chromatographic instrument with a pipette tip cell stationary phase column that can operate in a bidirectional mode. The instrument can be used for cell purification and diagnostic applications and cell stationary phase applications.

Columns, instruments and methods of the invention to purify and manipulate cells can be in different forms and configurations. An example of a general configuration is an instrument that operates primarily with back and forth fluid flow. This is shown by FIG. 11. The instrument may be used for cell purification, cell diagnostics or cell stationary phase chromatography.

In the figure a pipette is fitted to a column of the invention. In other examples, a syringe pump, gas pressurized/vacuum chamber pump or peristaltic pump can be fitted to a column of the invention. The pipette may be manual or electronic. The electronic pipette may be controlled with firmware and software contained within the pipette or may be controlled by an external computer or control. The pipette may be operated in a free standing mode with no hands or stand where the column end is inserted into a sample containing well or assembly and back and forth flow is operated electronically and semi automatically. The pipette is operates without manual intervention until placement into the next solution where the pipette again operates without manual intervention.

The pipette may be a single channel or multichannel pipette. The pipette, syringe pressure chamber or other pumping mechanism may be in the form of an automated robotic liquid handler where a single channel is operated, multichannel are operated in parallel, or up to 96 channels are operated in parallel. Columns of the invention may be operated one at a time or in parallel operation two or more at a time up to 96 at a time and optionally more.

The flow of fluids through the column is bi-directional back and forth with optional uni-directional flow for some methods. Semi-automated and automated refer to control of fluid through the column and placement and movement of the columns. Movement of the pipette or other pumping device from well to well can be performed manually. Optionally, the flow can be directed to a detector. The detector may measure a property of a well, or the detector may have flow through capability and a flowing stream is analyzed.

Columns of the invention may also be used with a fully automated liquid handler equipped to engage columns of the invention and process samples containing cells. The flow of fluids through the column is bi-directional back and forth with optional uni-directional flow for some operations. Movement of the column from well to well is performed automatically. Optionally, the flow coming out the end of the detector can be directed to a detector. The detector may measure a property of a fluid with a well where the fluid has been deposited, or the detector may have flow through capability and a flowing stream coming from the column is analyzed.

Figure 12:
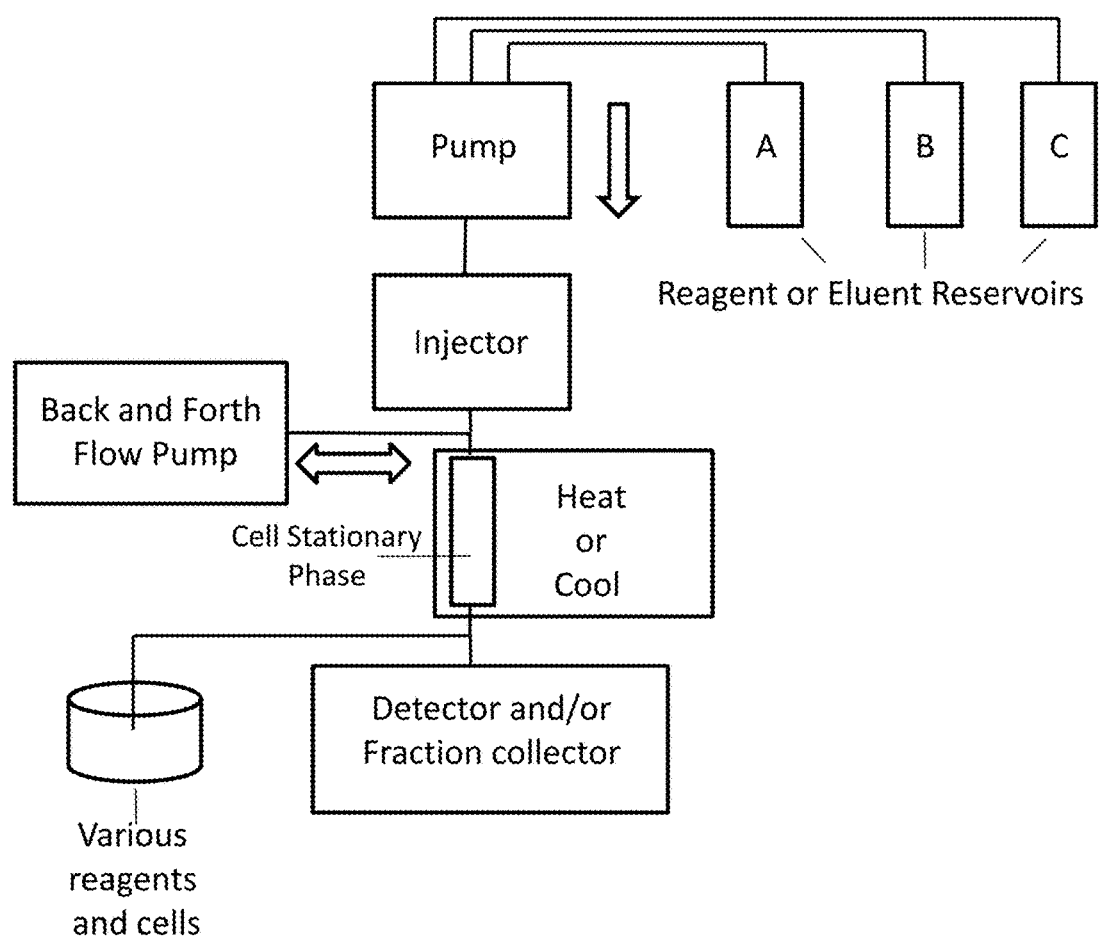
FIG. 12 is a depiction of a unidirectional flow column liquid chromatograph with a cell stationary phase column that operates using unidirectional flow. This instrument also contains a bidirectional flow pump for loading the cells onto the stationary phase. The instrument can be used for cell purification and diagnostic applications and cell stationary phase applications.

A more general instrument where unidirectional flow and bidirectional flow is used is shown in FIG. 12. The instrument may be used for cell purification, cell diagnostics or cell stationary phase chromatography.

The instrument is fully automated with a flow path of eluent reservoirs, pump, injector, living cell stationary column with optional column temperature control, detector and optional fraction or effluent collector. The pump may be a piston, peristaltic, air or gas pressure or syringe type pump. In some embodiments, there are two 3-way valves located at the column inlet and exit in order to optionally incorporate bi-directional flow through the column. Cells may be loaded onto the column and purified in this manner. The liquid chromatography instrument may be used for purification and recovery of cells either with cell sample injected into the column with the injector or loaded using back and forth flow. The cells may be eluted and recovered from the column and detected by changing the eluent pumped through the column. The liquid chromatography system is very useful for studying the differential interactions of analytes with the cell-based solid phase.

The chromatographic purification procedure may include combinations of unidirectional flow and bi-directional flow. For example, in the procedures described above, the cells may be loaded or captured by the column with back and forth flow and then the rest of the procedure performed with unidirectional flow.

In this configuration, not only is the column compatible with the cells so that they are not harmed, the tubing, tubing connections, valves, flow detectors and fraction collector are all cell compatible so that the cells are not harmed. This includes making certain the flow path does not contain any sharp edges or surfaces that may puncture the cell wall. In addition the flow path does not contain chemicals such as metal oxides that may chemically harm cells or adsorb cells.

The liquid chromatograph may optionally include temperature control of the sample that is captured, fluid that is pumped through the column and/or the column. Fluid may be pumped through the column to provide nutrients and preserving the cells of the stationary phase column. The fluid may contain glycerol and other material to slow metabolism to preserve the cells of the stationary phase column. The temperature may be lowered to preserve the cells of the stationary phase column.

Detection may be continuous or fractions may be collected and analyzed. Analyte measurements include retention time, capacity factor, selectivity coefficient, breakthrough curve parameters. Examples of detectors include Cell flow Cytometer, U V and Fluorescent, Refractive Index, Chemiluminescence, Electrochemical Detectors, PCR or other nucleic acid measuring detector, and Mass Spectrometer Detector.

Applications of cell-based stationary phase liquid chromatography include drug discovery, drug development (including personal drug development) and cell research. In drug discovery, the interaction of a library of compounds may be studied for a particular type of cell. In drug development, the interaction of a particular drug candidate, class of drug candidates, or analogs of a drug candidate may be studied. In cell research, the interaction of a compound with a particular cell or component of a cell may be measured and studied.

Measurement of Analytes and Cells in Cell Stationary Phase Liquid Chromatography Partitioning, gradient and displacement chromatography with a cell stationary phase may require the presence of competing entities to interact with the cell stationary phase. In the case of an antibody analyte interacting with the marker on the cell surface of a stationary phase, the eluent may contain another antibody or fragment of an antibody or a protein that has an affinity for a cell marker.

Displacement chromatography and frontal/breakthrough chromatography may be performed with or without a competing entity. Frontal chromatography is usually performed with unidirectional flow. These types of chromatography may be performed at different mobile phase ionic strengths, with different buffers and at a different pH to determine the extent of interaction of the analyte with the stationary phase.

Analytes may be small molecules or metabolic materials. These analyte materials may have rapid and reversible interactions with the stationary phase. In these cases, partitioning, gradient, step gradient, displacement or frontal chromatography may be performed. In other cases, the interactions of the small molecule or metabolic materials may be slow and even difficult to reverse. Competitive mobile eluents, having different mobile phase ionic strengths, with different buffers may be used to determine the extent of interaction of an analyte with the cell-based stationary phase.

It is possible to study how analyte libraries interact with cells for drug discovery, drug treatment or drug development.

Both the mobile phase analytes and the stationary phase functional group(s) can be analyzed and measured in this type of chromatography. No previously-described chromatography systems have this capability. Using the system, the interaction between analyte materials introduced into the cell-based stationary phase and the cells themselves can be characterized. For both the analyte and the cells, it is possible to determine whether or not there was an interaction and the extent to which the materials interacted. This examination can determine which material or materials interacted with the stationary phase, the manner in which they interacted, the extent of interaction (or non-interaction), which part of the cell stationary cell the material(s) interacted with and/or the effect of the interaction. This information can be exploited for a variety of downstream applications.

Stationary phase cells can be examined after they are used as a stationary phase. This examination is another means to determine the interaction of materials with a cell.

For example, a cancer cell stationary phase can be used to measure antibody interaction. The antibody may contain another material such as a toxin. The toxin can be delivered to the cell surface or into the cell.

Another example is a stationary phase comprised of bacterial cells used to examine antibacterial agent interaction and outcome.

Another example would be a stationary phase of epithelial cells in which cell signaling materials are used to measure interaction. After exposure to an analyte, the cell could be removed from the column and analyzed.

The interaction of an analyte with a cell may be measured by any type of chromatography. The ability to take up an analyte can be measured. Then, after optional removal of the analyte, the cells that make up the stationary phase may be examined to study the interaction.

After chromatography is performed, cells can be removed from the stationary phase and examined to see if they remain alive or are dead. In some embodiments, cell viability can be determined on column. Stains can be introduced to determine cell viability. The dead cells can be measured individually or together to determine if a reagent remains bound to the cells. The relative number or percentage of dead cells and live cells may be measured. The extent of damage to the cell membrane of a dead cell may be measured optically. A dye can be added that will only enter the cell if it is living. The ratio of dead cells and live cells may be measured as a function of time after exposure to a material.

Components, such as DNA, RNA, organelles, proteins, lipids, carbohydrates, etc. of the dead cells may be examined to determine the cause of the cells changing characteristics or dying. For example, the cell may be examined to determine if a reagent or portion of the reagent is associated with the cells and if the cells are alive or dead.

The treatment and manipulation of the cells must be gentle, both physical treatment and chemical treatment. Normal physical and chemical manipulation of a cell can cause damage to a cell and cause the cell to die. Measurements of cells loaded onto a resin to make a stationary phase but not used as a stationary phase is considered to be a background killing of cells which can serve as a control. These cells are not measured or their measurement is subtracted from the measurement signal.

These steps can be used for making and using a cell-based stationary phase.
1. Load or pack column with base resin beads.
2. Load column with an antibody or cell binding reagent.
3. Load column with cells. (In some embodiments, attach the cells to the beads and then pack the beads into the column.)
4. Expose column to a material with injection, block treatment, or breakthrough treatment and optionally measure interaction of the material with the cell stationary phase.
5. Optionally, wash the column.
6. Optionally, remove the cells from the column.
7. Analyze the cells for specific properties or characteristics.

Cell Stationary Phases with Controlled Mobile Phase Concentration:

Impervious resin may also be used for cell purification. Since antibodies and other affinity reagents that are used to functionalize the resin do not enter the matrix of the bead but are only in the interstitial space and channels of the column, then the concentration of the reagents are effectively much higher when they enter and travel through the column. They are not diluted by that volume of liquid that is within the resin matrix. Higher concentrations of the antibody, aptamer and other reagents is useful because less reagent will be needed to functionalize the resin and the conditions needed to functionalize the resin will be lower. A higher concentration of reagents can make it possible to drive equilibrium reactions to completion.

Cell stationary phase columns can be based on substrates that are swollen with water. These include agarose, Sepharose, dextran, cellulose and other hydrophilic polymers that swell with water. When reagents are introduced or pumped through columns containing these substrates, cells if present will travel to the surface. Cells may not be able to enter the stationary phase matrix because the pores may not be large enough. However water molecules, buffer molecules and other small size reagents may enter the pores of the resin substrate. Reagents such as aptamers, antibodies, FABs, and other affinity reagents may enter the stationary phase matrix.

This phenomenon can make it difficult to control of the chemical environment surrounding the cells. Reagents can be concentrated if they do not enter the pores of the substrate while reagents that enter the pore may become diluted. In any case, the concentration of any particular reagent after it enters the column and as it travels down the column is unknown and unpredictable. But it is important to determine the concentration of the reagents in order to practice chromatography in the most predictable manner.

In some embodiments of the invention, the substrate used to contain the cell stationary phase is solid and impervious. Water and buffers do not enter the stationary phase matrix. Examples of this are impervious silica and zirconia and other inorganic materials, solid impervious polystyrene and other polymers. With these materials, the reagents and cells do not enter the matrix or interior of the bead when the bead is exposed to reagents and cells. But rather they reside in the space between the beads or in the interstitial space of the media and channels or they reside on the surface of the media. The concentration of the reagents only changes if they react with the affinity phase and are not diluted or concentrated by water or reagents entering the stationary phase matrix.

In certain embodiments, an impervious resin is utilized. The reduction in non-useable surface area will decrease reagent costs and the rigid structure will facilitate an easier packing procedure. This is shown in Example 18 which describes the synthesis of *E. coli* with water-swollen agarose stationary phase and an impervious silica cell stationary phase. Impervious resins can be used for the capture and recovery of cells as well as for cell-based stationary phase liquid chromatography.

Drug Development

The cell-based stationary phase can be used for drug development applications. In some embodiments, cells can be immobilized on a column and then challenged with different entities such as libraries or pools of molecules (e.g., small molecule drug leads or biologics). In other embodiments, cells can be immobilized on a column and the interaction with other cells can be examined. Conversely, drug candidates can be immobilized on the column and challenged with different cell types.

In one example, a library of small molecule drug candidates labeled for identification can be exposed to cells immobilized on a column. A wash step can be performed and the cells can be eluted from the column. Those cells that have a drug candidate bound can be identified. Mass spectrometry can be used to identify the drug candidate and its target on the cell.

A number of techniques can be used to screen for potential drug leads. As mentioned previously, target cells can be immobilized on a column. When done in multiplex, multiple cell-immobilized columns can be screened in parallel. Multiplex operation can be performed with between 2 and 1536 columns simultaneously. Each column can be subjected to a different drug lead to screen for the desired cell interaction or signaling event. The following techniques can be used.
1. Eluting the cells and performing qPCR (e.g., to measure a change in gene expression or particular mRNA). For example, expression of genes involved in programmed cell death could be measured.
2. Use cells transfected with a reporter gene such as GFP or luciferase. The reporter gene would be engineered with a promoter region corresponding to the desired cellular event. If the promoter is induced by a drug lead, the cell would express the reporter. Detection of the reporter gene expression can be performed on column or after cells are eluted from the column. As an example, differentiation of stem cells could be measure with a reporter gene.
3. If the drug is designed to induce a regenerative cellular event, cell growth and doubling can be monitored as the final assay. Cells could be eluted and grown in cell culture.

In one example, cells having a known drug target could be used to identify potential drug as follows.
Put cells having a validated target on the column.
Challenge the cells on the column with library of fluorescently-labeled drug candidates.
Wash
Elute cells
Count/separate the labeled cells in a cell sorter.
Analyze cells or components of cells by mass spectrometry by LC/MS, MALDI, etc.

As an alternative to fluorescent labels, drug candidates could be labeled with DNA barcodes. PCR could then be used to identify particular candidates able to bind cells.

In another example, an unlabeled library can be used and drug candidates can be identified using a cell viability assay.
Put cells having a validated target on the column
Challenge with library of drug candidates
Wash
Add live/dead cell stain on column
Wash
Elute cells Alternatively, the cells can be stained after elution. The results could be evaluated using fluorescence microscopy or flow cytometry. A column in which the cells were not challenged with the drug candidate could serve as a negative control.

A variety of detection methods can be applied to the methods described herein. Non-limiting examples follow.
cell sorter or flow cytometry
fluorescence microscopy
light microscopy (e.g., to examine cell capture, viability or morphology)
mass spectrometry
PCR
sequencing
On-column or in-line detection
electrophoresis In another example it may be desirable to investigate the response of different cell types to a drug. For example, a known cancer drug effective on one cell type may also bind to or be effective against another cell type. The following experiment could be performed.
Attach labelled drug to the column (or could attach cells)
Add cancer cells of a different type
Wash
Elute
Count/separate labelled cells in cell sorter As mentioned above, partitioning may be useful in some instances. For example, partitioning can be used to distinguish between several promising drug candidates, all of which bind the cells with relatively low affinity.
Immobilize cells on a column
Add mixture of several labelled drug candidates
Collect fractions or use in-line detection In this experiment, the relative binding efficacy of each drug candidate is determined by its elution order. This technique can also be used to characterize the relative binding efficacy of different monoclonal antibodies. Cells can be immobilized on the column and challenged with different monoclonal antibodies. In some embodiments, a known drug might be tweaked for instance by mutagenesis or synthesis. The relative binding of different drug analogues could then be investigated using partitioning.

In another embodiment, the following experiment could be performed to simultaneously identify drug targets and drug leads.
1. Immobilize cell of choice on column
2. Screen DNA bar-coded small molecule drug libraries, antibodies or antibody derivatives
3. Present drug libraries to cell-immobilized columns
4. For a negative control, do not present drug libraries
5. Wash
6. Release negative control cells and cells in complex with drug leads
7. Disrupt negative control cells and cells in complex with drug leads to generate membrane fragments consisting of cell-surface proteins and cell surface proteins bound to drug leads
8. Run non-denaturing gels of negative control membrane fractions and experimental membrane fractions.
9. Identify, through gel shift, membrane protein-drug complexes.
10. Extract leads and use mass spec to identify membrane protein and drug lead.

In certain embodiments, cells can be immobilized on the column and displacement chromatography can be used. For example, it may be desirable to compete off a naturally-occurring ligand with a drug for a pathway blocking drug application.

Breakthrough or frontal chromatography can be used in some instances, particularly for drug maturation studies. Breakthrough curves such as the one shown in FIG. 9 can aid in identifying entities having the desired binding kinetics, regardless of whether they're fast or slow. Several drug candidates or analogues can be compared in this manner.

The use of columns is advantageous for sequential additions of different molecules or compounds. For example, to examine calcium-dependent interactions, calcium could be added to the cells immobilized on a column, followed by the addition of a library.

Liquid-Sealed Chromatographic System

The sealed chromatographic system is a liquid chromatography column that operates without exposure to ambient conditions. Once sealed, the components of the chromatographic device and liquids within the device cannot be contaminated by materials outside the sealed system. Ambient conditions are defined herein as the conditions of the surrounding environment. The sample, wash and elution solutions are passed through the column in a closed environment. The column can be sterile and can be used to isolate cells or enrich cells in a sterile environment. The column itself and the solutions passed through the column can be sterile. The entire chromatographic process is performed under sealed or closed conditions including sample loading onto the column, column washing, and column elution. The purified product is recovered in a closed receiving container. The sealed format prevents contaminants from entering the system. The system may contain one or more vents. However the vents must operate in a way that materials may only leave the system and not enter the system. Examples of vents may include check valves that only let material out, or a 0.2 micron filter that lets gases leave or enter but does not let bacteria or other contaminants enter the system.

As with other embodiments described herein, cells can be captured using affinity, hydrophobic interaction, reverse phase, normal phase, ion pairing, ion exchange or other strategies. Alternatively, an enrichment can be performed in which the desired cell types pass through the column while other non-desired materials are retained.

Liquids flow from a feed bag or reservoir to a receiving bag/reservoir. Flow through the column can be bidirectional or unidirectional. Bidirectional or back and forth flow can optionally be used for any or all of the equilibration, capture, wash and elute processes. The sealed system does not contain flow restrictions or backpressure to flow that will restrict the flow of liquid with the pumps used by the system. Of course, restrictions that provide backpressure that stop or slow the flow are harmful. But even small restrictions to flow are harmful because they could make the flow through the system unpredictable and unreliable. A pump may appear to work with a sealed system, but changing a parameter such as the tubing, column or fitting may marginalize the system to render the sealed system unreliable. Sealing the inlet reservoir may allow the pump to work for a time period, but may stop working if a negative pressure develops preventing feed of the liquid into the pump. Likewise, sealing the outlet reservoir may allow the pump to work for a time period, but may stop working if a positive pressure increases the resistance of flow out of the system.

Figure 14:
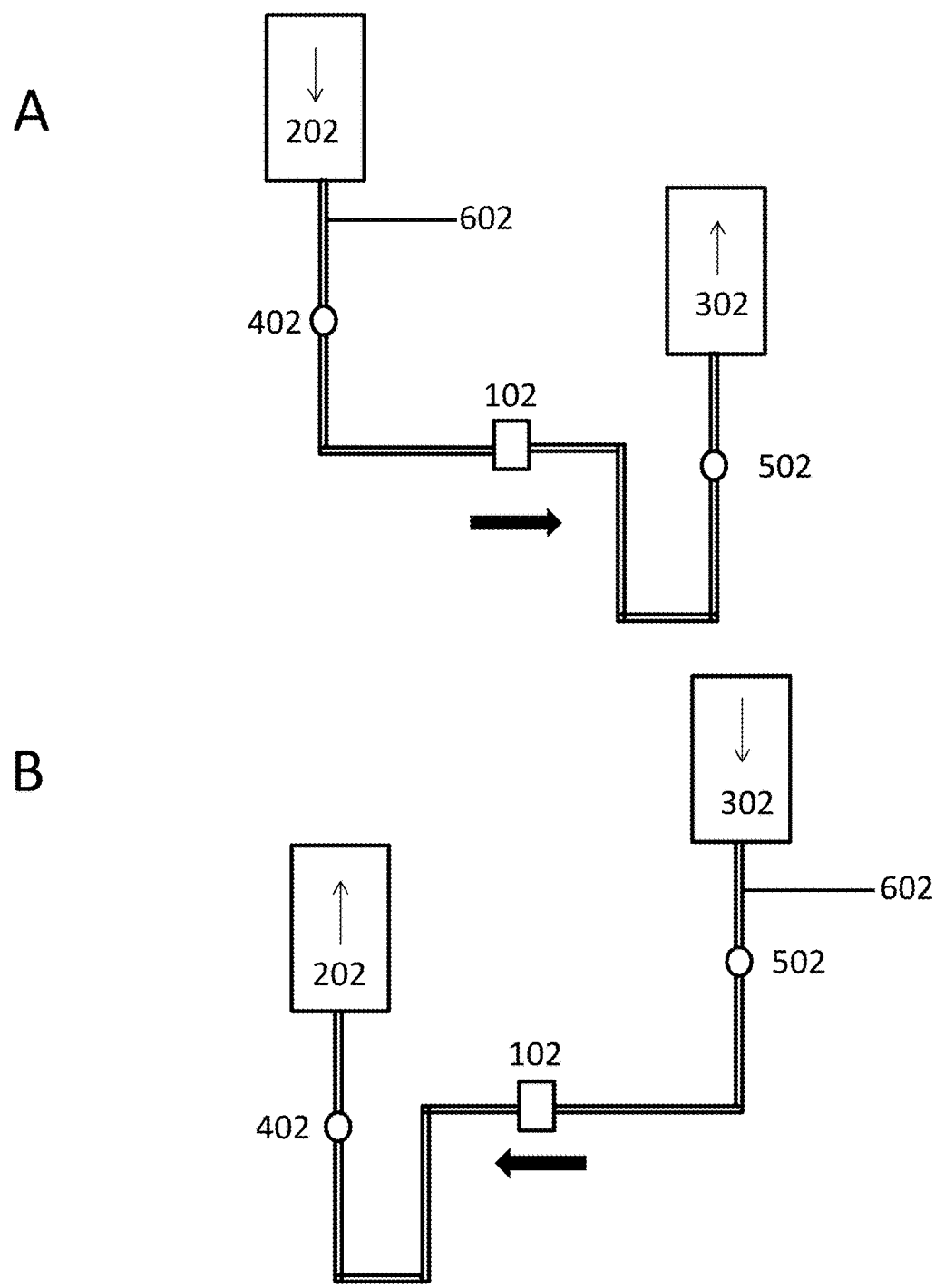
FIG. 14 depicts an embodiment of a closed column system for capture of cells with a back and forth flowing system.

FIG. 14 shows an example of a sealed column system for cell capture with a back and forth flowing system. The flow is controlled by the relative differences in the height of the feed and receiving closed containers. The system contains column 102 and reservoirs, 202 and 302. Depending on the direction of flow, a given reservoir can either be a feed to column 102 or the reservoir can receive flow from column 102. In some embodiments, the sealed column system may also contain on/off valves 402 and 502 to allow flow or stop flow. Reservoirs 202 and 302 are connected to valves 402 and 502 and column 102 with flexible tubing 602.

The flow through the column, 102 can be controlled by several different options. In one method, the relative difference in height of feed and receiving sealed containers will apply a positive pressure on one side of the column and a negative pressure on the other side of the column. In FIG. 14A, reservoir 202 is positioned above column 102 and reservoir 302 is positioned lower than reservoir 202. This will cause flow from reservoir 202 through the column 102 and into reservoir 302 as depicted by the arrow below column 102. The flow rate can be increased by changing the relative position of the two reservoirs, for example by increasing the height of reservoir 202 or lowering reservoir 302. Reservoir 302 may be placed below column 102 or above the height of column 102.

Reversing the positions of the two reservoirs as shown in FIG. 14B will reverse the flow through column 102 as shown by the arrow going from right to left below the column. Flow will stop when the feed reservoir is depleted or the receiving reservoir is full.

In some embodiments, flow through sealed column 102 may be powered by peristaltic pumps. For example, valve 402 and/or 502 may be replaced with a peristaltic pump or pumps. When a peristaltic pump is used, the tubing can remain sealed. Flow through the sealed column may also be performed with syringe pumps. For example, reservoirs 202 and/or 302 can be replaced with syringe pumps. In this embodiment, feed and receiving chambers 202 and 302 remain sealed.

Figure 15:
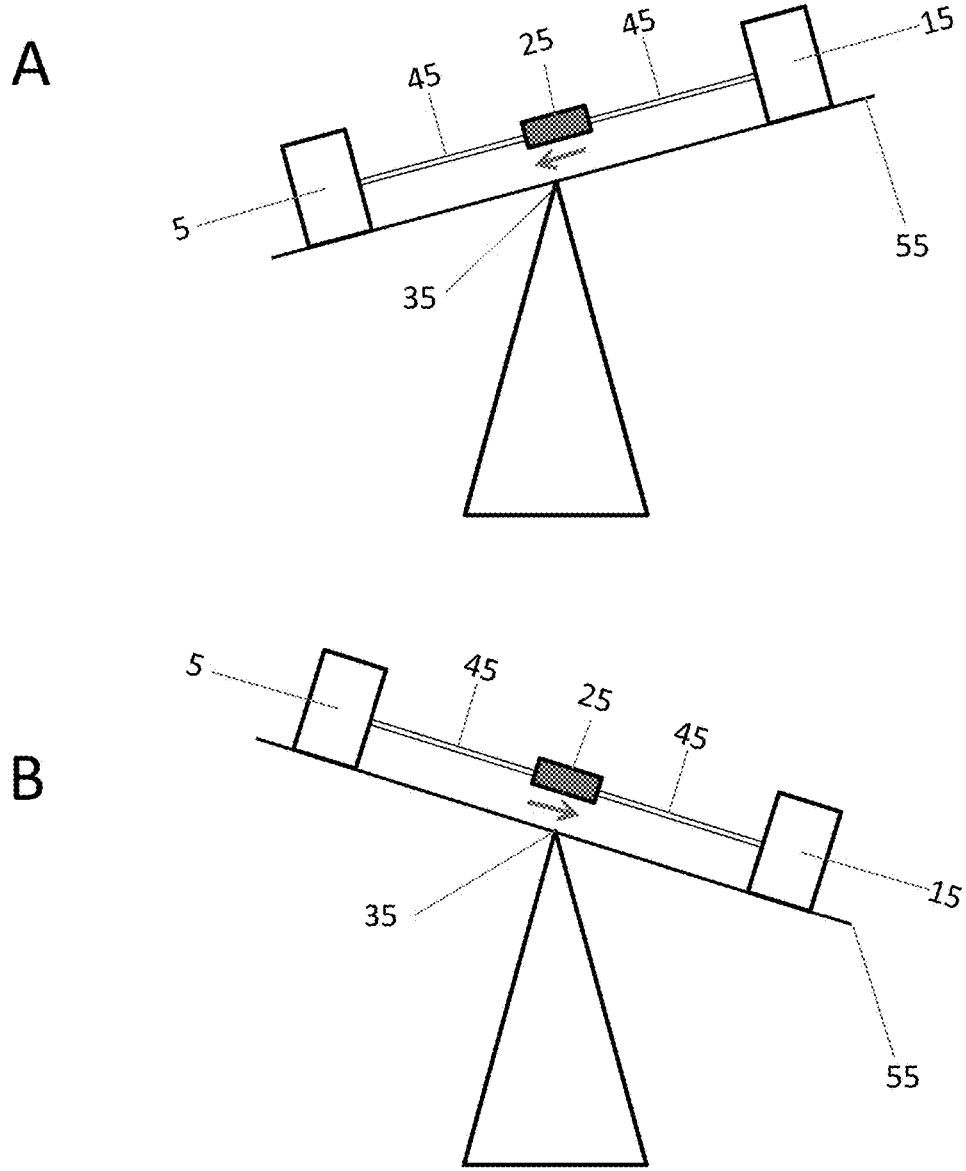
FIG. 15 depicts an embodiment of a closed column system for capture of cells with a back and forth flowing system with two each feed and receiving containers on each side of the column.

FIG. 15 shows an alternate embodiment of a sealed column system for capture of cells with a back and forth flowing system. The system contains column 25 and reservoirs 5 and 15. Depending on the direction of flow, a given reservoir can either provide feed to column 25 or receive effluent flow from the column. The reservoirs are connected to the column through tubing which can be flexible sealed tubing. The flow through the column 25 is controlled by placing the reservoirs and column on platform 55 where fulcrum 35 is positioned at or near column 25. The reservoirs are raised and lowered relative to each other by tilting platform 55 at fulcrum 35.

The relative difference in height of the feed and receiving sealed containers will apply a positive pressure on one side of the column and negative pressure on the other side of the column. In some embodiments the positive pressure of the feed reservoir can be in the range of 5 psi, 4.5 psi, 4 psi, 3.5 psi, 3 psi, 2.5 psi, 2 psi, 1.5 psi, 1 psi, 0.5 psi, 0.25 psi, 0.1 psi, 0.01 psi or 0.001 psi. Likewise, the pressure in the receiving reservoir can be in the same range, however it is also possible for the pressure of in the receiving reservoir to be 0. Flow will stop when the feed reservoir is depleted or the receiving reservoir is full.

Figure 16:
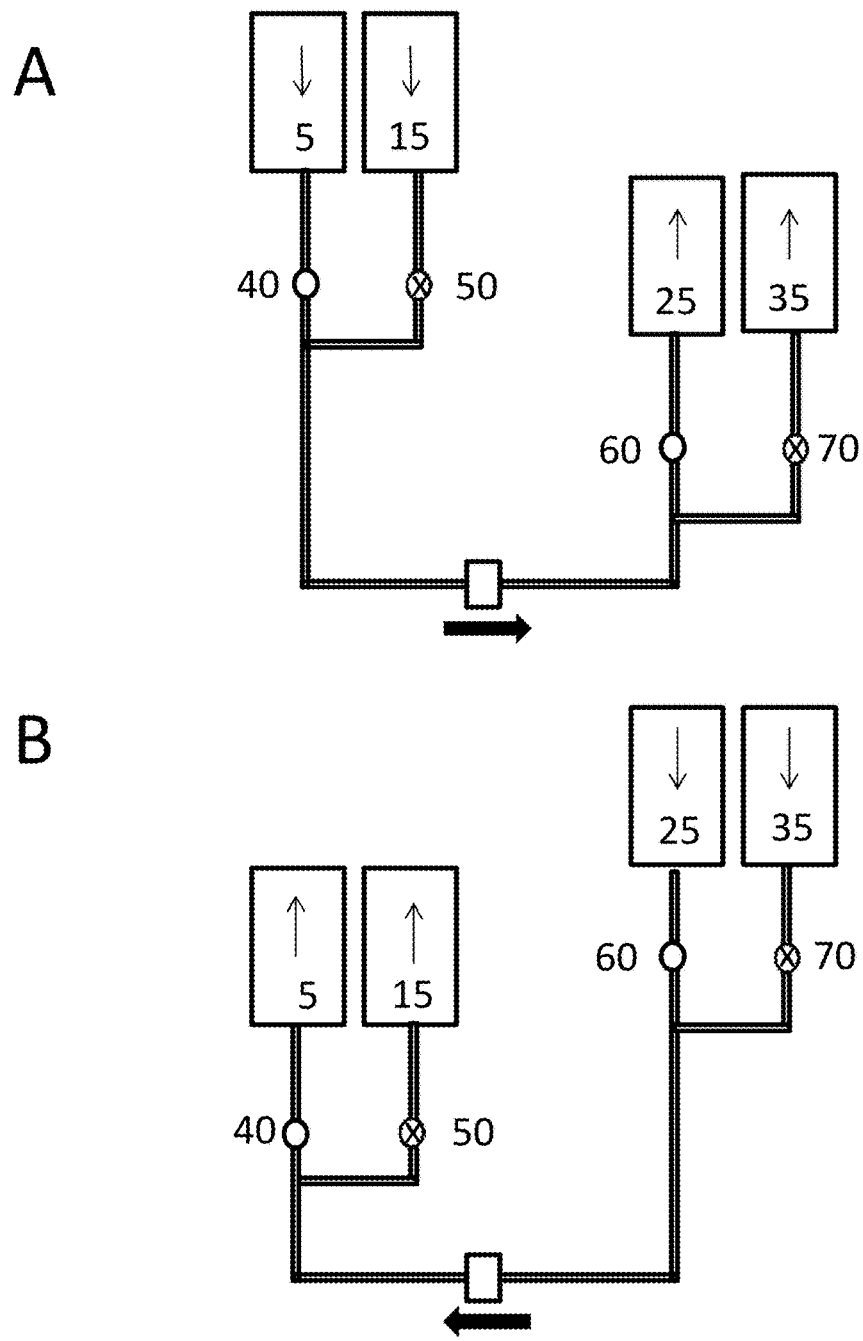
FIG. 16 depicts an embodiment of a closed chromatography column system for capture of cells with a back and forth flowing system with two each feed and receiving containers on each side of two optionally closed system columns.
Figure 17:
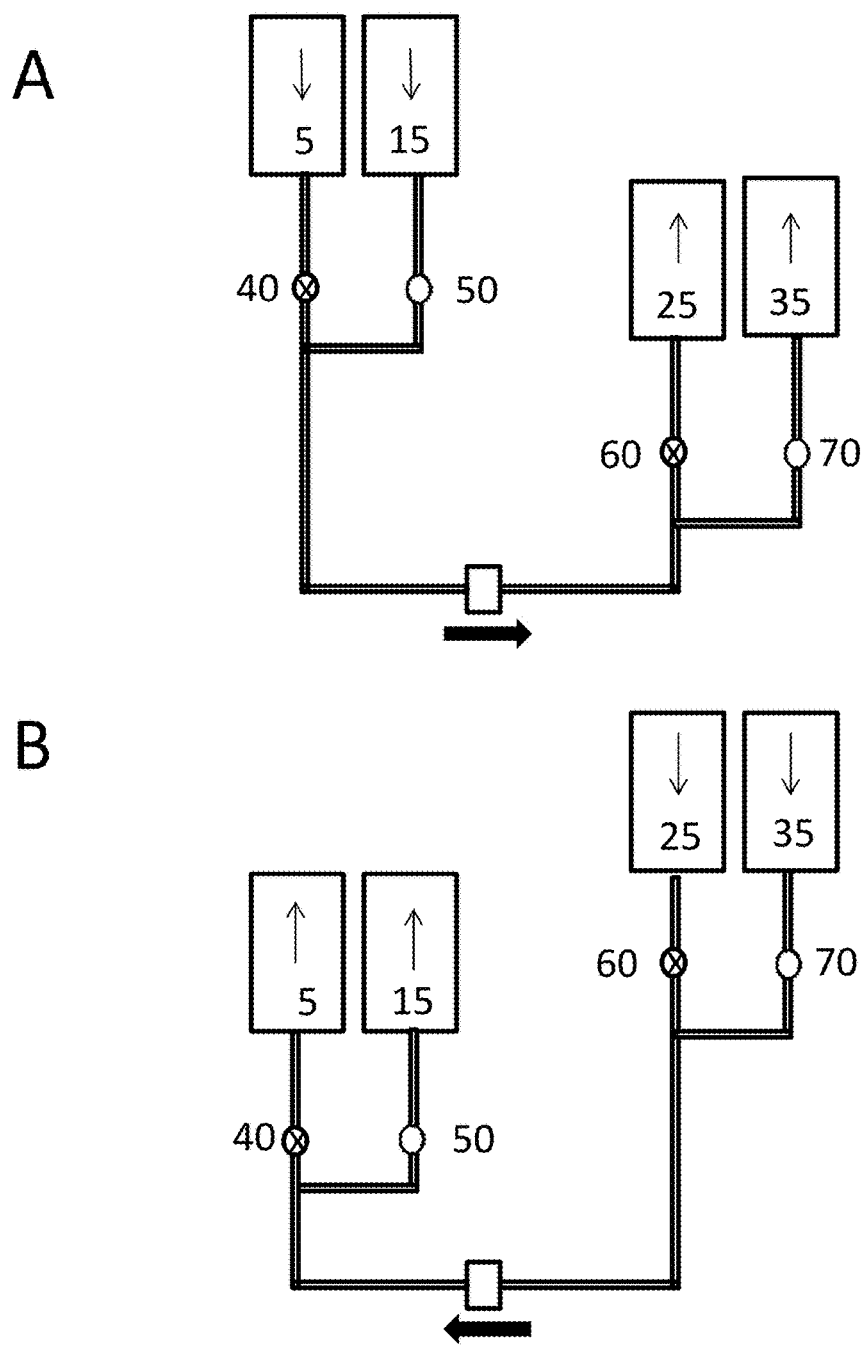
FIG. 17 depicts an embodiment of a closed chromatography column system for capture of cells with a back and forth flowing system with two each feed and receiving containers on each side of two optionally closed system columns.

FIG. 16 depicts a sealed column system for capture of cells with a back and forth flowing system with two feed and receiving containers on each side of the column. The on/off valves control the flow into and out of a particular container. In FIGS. 16A and 16B, valves 50 and 70 are closed and flow is between closed containers 15 and 35. FIGS. 17A and 17B depict the same system architecture in an alternate configuration in which valves 50 and 70 are open while valves 40 and 60 are closed.

Figure 18:
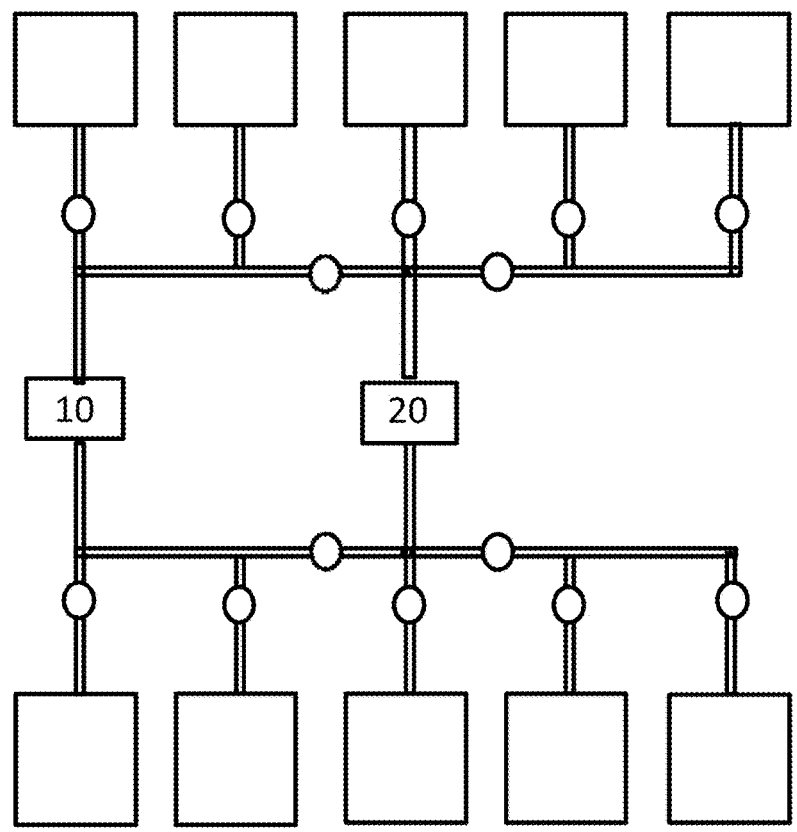
FIG. 18 depicts an alternative configuration of a sealed liquid chromatography column system for capturing cells using a flowing system with five each feed and receiving containers. The system may be used with unidirectional flow or back and forth flow. The pumping system may be gravity, pressure, vacuum, or peristaltic pumping.

FIG. 18 depicts an alternative configuration of a sealed liquid chromatography column system for capturing cells using a flowing system with five each feed and receiving containers. The system may be used in unidirectional flow or back and forth flow. The pumping system may be gravity, pressure, vacuum, or peristaltic pumping. In this configuration, there are two columns 10 and 20. Column 20 has five feed and receiving containers on each side of the column. The on/off valves control the feed and receiving container that is in use and the particular column that is used as described in FIG. 15. A specified purification, washing and recovery method uses a controlled sequence of valves (pictured as small ovals) opening and closing. Second column 10 gives the option of using a second chemical treatment on purified and recovered cells from column 20. The sealed chromatography system is described in more detail below in Example 22.

In some embodiments, a manifold can be used to introduce other liquid into the column in a sealed system including wash and elution solutions. A third bag can be configured to receive purified cells. A second column can be configured to clean the purified cells for materials including antibodies, biotin, etc. with the cells received into a fourth bag. In some embodiments, the system can be used to remove cancer cells or pathogens from blood. In all cases, back and forth flow can be used if necessary to achieve a complete reaction processes.

Pressures applied to the sealed chromatography system column and reservoirs are complex. The separation column has an additional backpressure or resistance to flow force exerted upon it. This is due to the eluent flowing out of the column which is in direct fluid contact with the reservoir of fluid collected from the column. The backpressure will change depending on the relative volumes of liquid above and below the columns (inlet and outlets) and the positions of the inlet and outlet volumes. It is not possible to predict the pressures as they are variable. It is surprising that that flow of fluids can be initiated (in either direction), maintained and established with the column configuration and design constraints. It is also surprising that the capture, washing and recovery of cells can be accomplished with variable flow rates and variable pressures. It is also surprising that the process can be performed reproducibly and predictably (predictable purity, concentration and volume).

In the sealed system, resistance of liquid and cell flow through the column is caused not only by the column but also by the receiving container which is in intimate contact with the fluid. A positive pressure is needed to expand the receiving container as it is filled from the column effluent. There may also be a pressure pushing back against or resisting the flow caused by the receiving container attempting to contract rather than expand. This resistance to flow through the column is in addition of the liquid attempting to flow through the column and the cells themselves having a resistance of transversing the column. Thus, the positive force needed to pump the cells and liquid through the column must overcome all of these forces in a sealed system. The positive force pushing the liquid through the column will be variable and, if gravity is used, will become exceedingly small, as the amount of liquid on top of the column approaches zero force with depletion of the liquid above the column. Nevertheless, all of the liquid can be pumped through the column.

The pumping force for a sealed system can be any peristaltic pump, positive pressure pump, piston pump, diaphragm pump, negative pressure pump, syringe pump, pipette pump, or gravity pump. The pump may force the liquids to flow through the system in back and forth flow bidirectional modes, unidirectional flow modes, single pass unidirectional mode, circulating pass mode or combinations of these flow modes.

Non-limiting examples of the ways in which the columns and methods of the invention can be used include the following.
1. capture and release of cells
2. depletion of cells from a complex mixture and retention of remaining cells
3. capture labeled cells, then release and count
4. Capture cells, lyse cells on column or after the cells have been eluted from the column. Collect DNA, RNA or proteins or other cellular components and analyze.
5. Purify sperm from other cells or from the environment.
6. Purify sperm from a crime scene away from other cells and other materials and perform DNA analysis to identify the source of the sperm
7. After cell capture, the column is washed and cells can optionally be reacted with a dye to label the captured cells. The resin may be removed from the column and plated or spread on a surface. The resin beads containing attached cells may be sorted and counted or analyzed by any means.
8. Capture a group or class of cells based on a specific parameter and then perform a secondary capture step to produce and recover a subset of cells.
9. Capture and recover cells from blood, fluid, marrow, skin and tissue.
10. Capture and recovery of live cells from the examples listed above from various samples including, blood, fluid, marrow, skin and tissue.
11. Capture and recovery of cells including T cells, organ cells, and stem cells. Cells are then used for therapeutic purpose.
12. Capture and recovery of large number of cells on a pipette tip column having a body size in the range of 2 mL-100 mL.
13. Therapeutic screening
14. Cell clean-up
15. Diagnostics for food, medical, environmental, forensics, etc.
16. Drug discovery
17. Drug development
18. Cell metabolic research
19. Organ cell device and methods where cells of a particular cell organ type are loaded onto a column.

EXAMPLES

Example 1. Sperm is Captured, Separated from Cells and DNA Analysis is Performed In forensics, it is often desired to obtain DNA profiles from old stains, body fluid samples and other possible samples. The primary goal is to preferentially separate sperm from vaginal cells and other materials, a necessity for DNA analysis in rape cases, for example.

DNA aptamers which are short strands of DNA were developed by SomaLogic (Boulder, Colo.) to bind sperm heads, and used to both identify and immobilize the sperm heads for purification and later DNA analysis. These aptamers are used in a column bed system of the invention with biotin and Streptavidin linkers to selectively capture sperm cells. The aptamer sequences bind preferentially to both the outer protein membrane and the stripped perinuclear calyx of sperm cells in the presence of non-sperm epithelial cells.

Sperm cells (research vials, prepared by density gradient centrifugation and subsequent washing) are purchased from California Cryobank. Washed sperm cells are prepared using three washes and suspension in a buffer supplemented with Triton X100 detergent and NaCl to final concentrations of 1% v/v and 600 mM HeLa cells to simulate non-sperm epithelial cells are added and the mixtures are incubated for ten minutes.

Cotton swabs are used to simulate capturing the sperm sample. The sample is removed from the cotton swab with a buffer. Aptamers with biotin linkers are added to the solution and incubated. After washing of the sample the mixture is passed through a streptavidin packed bed column of the invention. The sperm is captured and subsequently washed by passing wash buffer through the column.

The sperm is eluted from the column by passing a buffer through the column breaking up the aptamer/sperm column. Eluted aptamer DNA are purified and then amplified for DNA analysis.

Example 2. Antibody Purification of Sperm

This example uses antibodies rather than aptamers to capture sperm cells in the presence of other cells. A cocktail of antibodies specific to sperm cell surface antigens are anchored to Protein A affinity beads packed into a column of the invention. The specificity of antibody-antigen binding selectively captures sperm cells from samples that are comprised of a mixture of sperm cells, white blood cells, epithelial cells, cell lysates, etc. Alternatively, the antibodies are added to the sample mixture first and then captured by the column. After washing with a neutral buffer, the sperm cells are eluted with low pH or high pH buffers and the DNA is analyzed.

The antibodies may be tagged with His tags for example. In this case, IMAC beads may be packed into columns of the invention to capture the antibodies which are used in turn, to capture the sperm. In this case, the antibody sperm combination may be eluted, the cell lysed and the DNA analyzed. Other tags may be used such as FLAG-ANTI FLAG, etc.

Peptide tags are used for capture. These include AviTag, a peptide allowing biotinylation by the enzyme BirA so the protein can be isolated by streptavidin, Calmodulin-tag, a peptide bound by the protein calmodulin, FLAG-tag, a peptide recognized by an antibody, HA-tag, a peptide recognized by an antibody, Myc-tag, a short peptide recognized by an antibody, SBP-tag, a peptide which binds to streptavidin, Softag 1, for mammalian expression, Softag 3, for prokaryotic expression, V5 tag, a peptide recognized by an antibody, and Xpress tag.

Covalent tags include Isopeptag which binds covalently to pilin-C protein and SpyTag which binds covalently to Spy-Catcher protein.

Protein tags include BCCP (biotin Carboxyl Carrier Protein), a protein domain recognized by streptavidin, glutathione-S-transferase-tag, a protein which binds to immobilized glutathione, green fluorescent protein-tag, a protein which is spontaneously fluorescent and can be bound by nanobodies, maltose binding protein-tag, a protein which binds to amylose agarose, Nus-tag, Strep-tag, a peptide which binds to streptavidin or the modified streptavidin called Strep-Tactin and Thioredoxin-tag.

Example 3. Circulating Tumor Cells

A cancerous tumor sheds small numbers of tumorous cells into its immediate vasculature. These cells then make their way into the circulatory system, and are thus called circulating tumor cells (CTCs). CTC information is used cancer prognosis, therapy monitoring and metastasis research.

Circulating tumor cells (CTCs) are important targets for study to understand, diagnose, and treat cancers. However, CTCs are found in blood at extremely low concentrations which makes isolation, enrichment and characterization challenging. A typical concentration in a human cancer patient is approximately 1-100 CTCs per mL of blood.

CTC purification with the columns of the invention capture many or most of the CTCs in the blood sample (high capture efficiency) and are selective with very few other cells accidently isolated. The samples are processed with sufficient speed and without battering of the cells so that cells remain viable in many cases.

The columns of the invention operate by coating the column media with an antibody (anti-EpCAM) and then bonding the antibody to the epithelial adhesion molecules (EpCAM) of CTCs. After capture of anti-EpCAM labeled CTCs from a blood sample, CTC identification and enumeration are achieved using immunostaining.

During one experiment 2 to 80 spiked breast cancer cells are isolated from 1 mL of mice blood sample with 90% capture efficiency. A 200 µL bed column with a 1 mL pipette tip body is used for one experiment. Whole blood is processed through the column with bidirectional flow for 5 cycles at 200 µL/min flow rate. The column is washed with buffer and then the cells are eluted with 500 mM citric acid.

Example 4. Capture of Cells from Blood

The purification and analysis processes used in example 3 are used for other cell types including white blood cells, stem cells, T cells, B cells and others. In this example, the medium used can be capable of capturing each cell type. Alternatively, the medium may capture other sample components, thereby enriching for the desired cell type.

Example 5. Capture of Cells from Blood

The purification and analysis processes used in examples 3 and 4 are used except the pumping methods for flowing the fluids through the column are changed as follows. The pumping method is bidirectional, unidirectional, gravity flow and gravity flow plus vacuum and/or pressure.

In addition, the method is performed with two different column configurations. In one configuration, there is an air gap above the column bed, while in the other configuration, there is no air gap above the column bed.

Example 6. Capture of Cells from Blood

The purification and analysis processes used in examples 3, 4 and 5 are used except the column has a bed volume of 1 mL inside a 10 mL pipette body. The flow rates are approximately 10 times faster with this column so samples sizes approximately 10 times greater are processed in approximately the same time.

In this example the cells are released from the column by enzymatic and chemical cleavage of the linker. The cells are collected and counted.

Example 7. Capture of Cells from Tissue

For tissue samples composed of different types of cells, heterogeneous cell populations will be present. To obtain as much information as possible about an individual cell type, biologists have developed ways of dissociating cells from tissues and separating the various types. A mild procedure is used to collect whole, intact cells. Homogenized cells are kept at low temperatures to prevent autolysis and kept in an isotonic solution to prevent osmotic damage.

The first step in isolating cells of a uniform type from a tissue that contains a mixture of cell types is to disrupt the extracellular matrix that holds the cells together. For example, viable dissociated cells are obtained from fetal or neonatal tissues. The tissue sample is treated with proteolytic enzymes (such as trypsin and collagenase) to digest proteins in the extracellular matrix and with agents (such as ethylenediaminetetraacetic acid, or EDTA) that bind, or chelate, the $Ca^{2+}$ on which cell-cell adhesion depends. The tissue can then be teased apart into single living cells by gentle agitation to make a cell suspension.

Columns of the inventions are loaded with antibodies that have an affinity for fetal cells. The suspension is passed with bidirectional flow through the column to capture the cells. After washing, the cells are released with by treatment with trypsin to digest the antibodies. The cells may be visually tagged by using an antibody coupled to a fluorescent dye to label specific cells.

Given appropriate surroundings, most plant and animal cells can live, multiply, and even express differentiated properties in a tissue-culture dish. The cells can be watched continuously under the microscope or analyzed biochemically, and the effects of adding or removing specific molecules, such as hormones or growth factors, can be explored. In addition, by mixing two cell types, the interactions between one cell type and another can be studied. Experiments performed on cultured cells are sometimes said to be carried out in vitro (literally, "in glass") to contrast them with experiments using intact organisms, which are said to be carried out in vivo (literally, "in the living organism"). These terms can be confusing, however, because they are often used in a very different sense by biochemists. In the biochemistry lab, in vitro refers to reactions carried out in a test tube in the absence of living cells, whereas in vivo refers to any reaction taking place inside a living cell (even cells that are growing in culture).

Example 8. Capture of Bacterial Cells

An *E. coli* culture is grown at 37° C. The *E. coli* strain is engineered using recombinant DNA techniques so that surface proteins on the cell contain histidine tags. A spike of *Salmonella* is added to the sample so that the sample contains 10% *Salmonella* cells, 90% *E. coli* cells, media and other materials.

A 1 mL bed size column containing Ni form IMAC affinity media is used to treat or process a 3 mL sample with unidirectional single pass flow under gravity. Some air pressure is used to push the last remaining solution through the column. The *E. coli* cells are removed from the mixture and are captured on the column while the *Salmonella* cells remain in the sample.

Example 9. Capture of Cells from Culture

Most plant and animal cells can live, multiply, and even express differentiated properties in a tissue-culture dish. The cells can be watched continuously under the microscope or analyzed biochemically, and the effects of adding or removing specific molecules, such as hormones or growth factors can be explored. In addition, by mixing two cell types, the interactions between one cell type and another can be studied. After growing the cells, the specific cells are captured according to processes similar to those described in examples 7 and 8.

After capture, the column is washed and optionally reacted with a dye to label the captured cells. The resin may be removed from the column and plated or spread on a surface. The resin beads containing attached cells may be sorted and counted or analyzed by any means.

Example 10. Companion Diagnostic to Antibody or Fab Based Drug

Often it is unknown whether a particular antibody or Fab drug will be effective against a particular cancer case. The treatment process can be trial and error, trying one drug and then if it is not effective, trying the next drug and so on. Columns of the invention may be used to determine the potential effectiveness of a series of drugs. Tagged drug antibodies and Fabs are prepared. A series of columns of the invention are prepared each with a single antibody bound through the tag to the media of the column. In this way, each available drug is represented by a column. Then a blood sample from a cancer patient is treated by the series of columns in an attempt to capture circulating tumor cells. The columns are washed and the cells, if present, are recovered and analyzed by fluorescence, DNA, microscopy or any suitable analytical technology. Specific drugs that may be effective against the cancer are captured containing drug based affinity media. Then a treatment program is designed using the antibody/Fab drugs that have the highest affinity for the tumor.

Example 11. Nickel-IMAC Column Sterilization 1-ml pipette tip columns containing 80 μL of Ni-IMAC resin were manufactured and 100% glycerol was added to the columns so that the glycerol filled the resin bed up to several millimeters above the bed. The columns were placed in a pipette tip box and the box was autoclaved at 132° C. for 45 minutes.

To verify column sterility, the column resin and a piece of the column body were placed on an LB plate and the plate was incubated at 37° C. After 3 days, no bacterial growth was evident.

The performance of the autoclaved columns was compared with identical columns that had not been autoclaved. His-tagged enhanced green fluorescent protein (eGFP) was purified on the columns using an E4 XLS pipette (Rainin) as shown in Table 1.

After the sample was loaded onto the columns, two washes were performed. The column was washed with 10 mM $NaH_2PO_4$, 5 mM Imidazole, 0.3 M NaCl, pH 7.4 followed by 10 mM $NaH_2PO_4$, 0.3 M NaCl, 20 mM Imidazole, pH 7.4. Next the eGFP was eluted with 10 mM $NaH_2PO_4$, 0.14M NaCl, 0.25M Imidazole, pH 7.4.

TABLE 1

E4 XLS pipette settings:

|  | Volume mL | Cycles | Speed |
|---|---|---|---|
| Equilibration | 0.50 | 1 | Medium |
| Sample | 0.50 | 4 | Medium |
| Wash 1 | 0.50 | 2 | Medium |
| Wash 2 | 0.50 | 2 | Medium |
| Elute | 0.24 | 4 | Medium |

The absorbance of the eluate was read at 488 nm and the yield of purified eGFP was determined. Both the autoclaved column and the column that had not been autoclaved were able to capture eGFP as shown in Table 2 below.

TABLE 2

Columns 1 and 2 were autoclaved and columns 3 and 4 were not autoclaved.

| Column | eGFP excitation peak | Absorbance | Concentration mg/mL | Volume mL | Yield mg |
|---|---|---|---|---|---|
| 1 | 488 | 0.075 | 0.331 | 0.733 | 0.242 |
| 2 | 488 | 0.074 | 0.326 | 0.741 | 0.242 |
| 3 | 488 | 0.081 | 0.357 | 0.753 | 0.269 |
| 4 | 488 | 0.079 | 0.348 | 0.740 | 0.258 |

Example 12. Protein-A Column Sterilization 1-ml pipette tip columns containing 80 μL of ProA resin (PhyNexus, Inc., San Jose, Calif.) were placed in a pipette tip box and the box was autoclaved at 132° C. for 45 minutes. Some of the columns contained glycerol while others did not.

To verify column sterility, the column resin and a piece of the column body were placed on an LB plate and the plate was incubated at 37° C. After 3 days, no bacterial growth was evident.

IgG was loaded on the columns and the columns were operated with an E4 XLS pipette (Rainin) as shown above in Table 1. After the sample was loaded, the columns were washed with phosphate buffered saline (Wash 1) and 140 mM NaCl (Wash 2). The protein was eluted with 200 mM $PO_4$, 140 mM NaCl @ pH 2.5.

The protein yield from the autoclaved columns was compared with the yield obtained from identical columns that had not been autoclaved. The yield of purified IgG obtained the autoclaved proA columns was comparable to those columns that had not been autoclaved.

Example 13. Column Sterilization

Four, 1-ml pipette tip columns containing 80 μL of agarose resin were autoclaved at 132° C. for 45 minutes. Two different agarose resins were used; agarose 1 and agarose 2. Prior to autoclaving, glycerol was added to one column of each resin type. After autoclaving, it was observed that the resin dried out in the columns that did not contain glycerol while the two columns with glycerol added remained wet as shown in Table 3.

TABLE 3

Column sterilization

| Resin | Glycerol | Autoclaved | Dried Out |
|---|---|---|---|
| Agarose1 | No | Yes | Yes |
| Agarose1 | Yes | Yes | No |
| Agarose2 | No | Yes | Yes |
| Agarose2 | Yes | Yes | No |

Example 14. Negative Isolation of Stem Cells

In this example, a sample is enriched for stem cells by removing other cell types. A column is assembled in which the medium is comprised of antibodies that bind undesired cells. The sample is loaded onto the column and the undesired cells are captured on the column. The column flow-through is collected and shown to be enriched for the desired cells.

Example 15. Negative Selection of T Cells from Peripheral Blood Mononuclear Cells T cells are isolated by depletion of all non-T cells such as B cells, macrophages, and natural killer cells. Peripheral blood mononuclear cells (PBMC) are incubated with a mixture of monoclonal antibodies to coat unwanted cells. The suspensions are then loaded onto a column comprised of IgG, which binds the antibody-coated cells. The column flow-through is collected and shown to be enriched for the T cells.

Example 16. Negative Selection of T Cells

The method from Example 15 is applied to different samples such as cells from spleen, lymph node, tumor, and peritoneal fluid.

Example 17. Purification of Sperm Cells by Aptamer Binding

An RNA aptamer having the following sequence is synthesized. Ggcagtccgt ccgtcAZCGA CGCGZGZGZG ZZZGZCZZCZ ZGZZZGZZGZ CGZGCgccag aagcagaagg acg Z is the modified base, 5-(N-benzylcarboxyamide)-2'-deoxyuridine. A photocleavable linker is conjugated in between the beads and the aptamer to elute the bound cells from the RNA aptamer in one step by UV irradiation.

The synthesized aptamer is incubated with streptavidin beads in a 1 ml pipette-tip column containing 80 μl of streptavidin resin. A 1 ml sample comprised of sperm cells mixed with other cells is eluted from a swab obtained from sexual assault evidence and diluted in 40 mM Hepes pH 7.5, 350 mM NaCl, 1 mM EDTA, 0.5 mM EGTA, and 0.1% Triton X100 detergent.

The sample is aspirated and expelled from the pipette tip column three times at a rate of 150 μl/min. Non-specifically bound material is removed from the column by washing the column three times with 1 ml of 40 mM Hepes pH 7.5, 350 mM NaCl, 1 mM EDTA, 0.5 mM EGTA, and 0.1% Triton X100. To cleave the aptamer and cells from the resin, the column is subjected to UV irradiation at 1050 mW/cm2 for 5 min. The cells are eluted by aspirating and expelling two times with 500 μl of 40 mM Hepes pH 7.5, 350 mM NaCl, 1 mM EDTA, 0.5 mM EGTA, and 0.1% Triton X100 detergent.

Example 18. Biotinylated Silica Resin

The procedure outlines the creation of antibody conjugated silica beads for capture of E. coli. Silica beads were conjugated to biotin. Subsequently, the beads were reacted with aqueous avidin and then E. coli antibody tagged with biotin.

Piranha Solution Treatment
Goal: Adding hydroxyl groups to surface of silica.
SIGMA g4649-100G 106 um silica beads acid washed
95% sulfuric acid stock
30% peroxide stock
Methanol
1. Slowly add 13.1 mL sulfuric acid to 11.9 mL water to make 50% sulfuric acid.
2. Slowly add 25 mL 30% peroxide solution to 50% sulfuric acid solution to make Piranha solution.
3. Add 25 grams of silica beads to solution and mix every 15 minutes for 60 minutes at room temperature.
4. Add silica bead solution to Buchner funnel with #2 filter paper.
5. Wash with dH$_2$O.
6. Wash with methanol.
7. Store powder in beaker at room temperature to dry.

Silanol Conjugation
Goal: Adding amine groups to surface of silica by reacting silanol with hydroxyl groups.
Toluene
APES (3 aminopropyl triethoxy silane)
Alcohol (Anhydrous Reagent 97% Isopropanol)
1. Add glass beads to round bottom flask.
2. Mix 10 mL APES with 90 mL toluene and add it to flask.
3. Spin intermittently on rotovac for 2 hours at room temperature.
4. Add to Buchner funnel with #2 filter.
5. Wash with alcohol (Anhydrous Reagent 97% Isopropanol).
6. Store powder in beaker at room temperature to dry.

Biotin Conjugation
Goal: Adding biotin to surface of silica by reacting NHS with amine groups.
CAYMAN CHEMICAL COMPANY Item 13315 Biotin NHS (Biotin N-Hydroxysuccinimide Ester)
DMSO
Alcohol (Anhydrous Reagent 97% Isopropanol)
1. Dissolve 500 mg biotin NHS in 100 mL DMSO.
2. Add glass beads to 250 mL round bottom flask.
3. Add 50 mL biotin solution to round bottom flask.
4. Mix by hand every 8 minutes for 2 hours at room temperature.
5. Add to Buchner funnel with #2 filter
6. Wash with alcohol (Anhydrous Reagent 97% Isopropanol).
7. Store powder in 50 mL conical tube in refrigerator.

Example 19. Packing Pipette Tip Columns

Column Packing—Antibody Pipette Tip Columns
1. Add powdered biotin-conjugated resin to tip body.
2. Dispense alcohol (Anhydrous Reagent 97% Isopropanol) into pipette tip column.
3. Store in 50 mL conical tube at room temperature Column Packing—Ion Exchange Tip Columns Strong Base Anion Exchange Resin Tip Columns
1. Suspend strong anion exchange agarose resin in water.
2. Aliquot into reservoir
3. Mix with pipette then pipette 500 uL into Eppendorf tube.
4. Continually add resin to column body and allow to drain until 500 uL has been added
5. Keep in 50 mL tube with dH$_2$O at room temperature

Example 20. Capturing and Eluting E. coli Cells on Pipette Tip Columns

Loading E. coli Cells onto the Column Substrates
Experiment
Using pipette tip columns packed with experimental avidin resin, determine whether DH5α E. coli cells can be captured. Compare purification process with pipette tip columns packed with ion exchange agarose.
Prepare Sample
1) Inoculate 5 mL TB medium with single colony of DH5α.
2) Incubate at 37° C. for approximately 16 hours with shaking at 350 rpm.
3) Measure absorbance at 600 nm until reading reaches 2.4.
4) Aliquot 1 mL culture into 1.5 mL microfuge tubes.
5) Centrifuge at 5,000 rpm for 5 minutes or until medium is clear.
6) Discard medium with a pipette tip.
7) Wash cells—resuspend in 1 mL H$_2$O, centrifuge at 5,000 rpm for 5 minutes, and discard water.
8) Repeat wash two more times for a total of 3 washes.
9) Resuspend cells in 0.5 mL water.
10) Measure absorbance at 600 nm.
11) Make a dilution to a concentration of $1\times10^9$ cells/mL or OD 1.4. Label "Concentrated Cells"
12) Sample=100 μL of Concentrated cells+400 μL H$_2$O, or 100 million cells.

Conjugate Avidin to Biotin Pipette Tip Columns
1) Equilibrate pipette tip columns with 500 μL phosphate buffered saline (PBS), 1 cycle, 0.5 mL/min, 20 second pauses.
2) Prepare avidin
Avidin is supplied as lyophilized 5 mg powder (Prospec, pro-500-a)
The molecular weight of avidin is 68 kDa, the bottle contains 73.5 nmoles of avidin
Use a syringe needle to vent the bottle
Use another syringe and needle to resuspend the powder in 735 uL H$_2$O to make a 100 uM solution. Make 100 μL aliquots and freeze.
Make 100 uL of 10 uM avidin: 10 μL 100 uM avidin+90 uL H$_2$O.
Load 100 picomoles per pipette tip column: 10 μL 10 μM avidin+240 μL H$_2$O
3) Load avidin onto biotin-derivatized pipette tip columns
Capture with 4 cycles, 0.5 mL/min, 20 second pauses
4) Wash pipette tip columns with 500 μL PBS, 1 cycle, 0.5 mL/min, 20 second pauses.
5) Load biotin-antibody (Pierce, PA1-73035)
Antibody is supplied as 1 mL solution at 4 mg/mL
The molecular weight of IgG is 150 kDa
The solution is 0.0267 μM
Make 200 μL aliquots and freeze.
Load 0.5 picomoles of Antibody per pipette tip column: 18.7 μL of 0.0267 μM IgG+231.3 μL H$_2$O
Capture with 4 cycles, 0.5 mL/min, 20 second pauses
6) Wash pipette tip columns with 500 μL PBS, 1 cycle, 0.5 mL/min, 20 second pauses.

Load Cells
1) Equilibrate pipette tip columns with 500 μL PBS, 1 cycle, 0.5 mL/min, 20 second pauses.
2) Load pipette tip columns with 500 μL Cell Solution, 4 cycles, 0.5 mL/min, 20 second pauses.

3) Wash pipette tip columns with 500 μL PBS, 1 cycle, 0.5 mL/min, 20 second pauses.
4) Elute Avidin pipette tip columns: 300 μL Buffer C (200 mM phosphate pH 2.5, 140 mM NaCl), 3 cycles, 0.5 mL/min, 20 second pauses Ion exchange pipette tip columns: 300 μL 1M $Na_2SO_4$, 3 cycles, 0.5 mL/min, 20 second pauses Analyze 1) Visual inspection Note sample turbidity after each capture cycle Note turbidity of elution 2) Measure absorbance at 600 nm on disposable plastic 1.5 mL cuvettes.

*E. coli* Column Capture Loading Experiment Results

Figure 13:
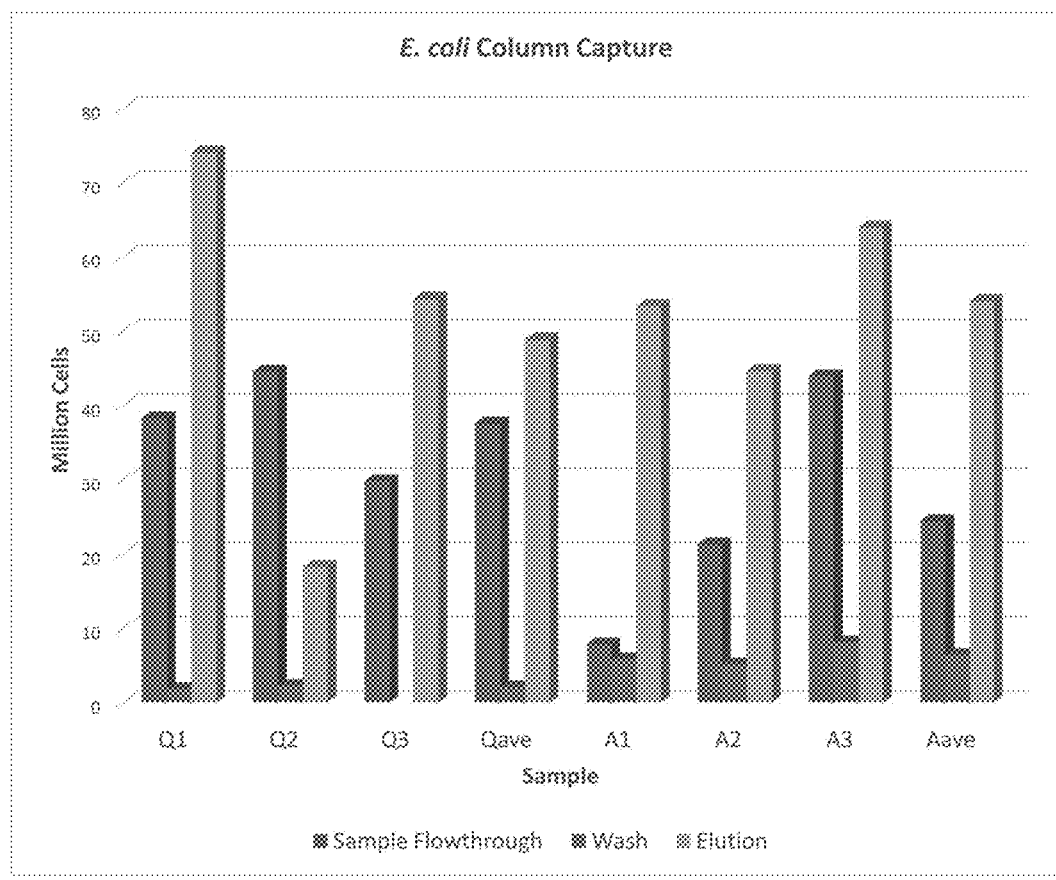
FIG. 13 is a graph showing the number of E. coli cells that are captured on an agarose quaternary ammonium resin (Q) and a silica solid resin (A).

The results indicated that cells can be captured and eluted with pipette tip columns. Six samples were run through the columns using the MEA workstation (PhyNexus, Inc. San Jose, Calif.) as described above. There were three ion exchange columns (Q1-Q3) and three antibody-based columns (A1-A3). Each column was exposed to 100 million cells during the capture cycle and the average number of cells eluted was in the range of 50 million (FIG. 13). The concentration of each individual sample was measured via $OD_{600}$ reading which was then converted to concentration per mL via a ratio calculated from previous experiments. *E. coli* is captured on a strong anion exchange resin due to surface markers on the cell that contained anion exchange groups.

Six samples were run through the six columns and the number of cells in the sample flow-through, wash, and elution were counted via OD reading for each column. Very few cells were released in the washing stage indicating that both resins were able to retain cells until the elution step.

TABLE 4

The total number of cells counted is in the range of 95 million.

| Sample | Total Million Cells Counted |
|---|---|
| Q1 | 114 |
| Q2 | 65 |
| Q3 | 84 |
| A1 | 67 |
| A2 | 71 |
| A3 | 116 |
| Original | 95 |

The data indicate that the creation of a cell capture pipette tip column was successful. The cell stationary phases are now ready to be used for chromatography.

Example 21. Evaluation of Stem Cell Multi-Potency

One method to evaluate stem cell multi-potency is to measure expression cell surface antigens e.g. CD105, a positive marker for hMSC. These surface antigens can be used to purify multipotent stem cells from a mixture of non-multipotent stem cells and other material. An antibody to CD105 or other specified surface markers can be attached to the affinity resin. The cell culture is passed through the column to capture the multipotent stem cells. Non-specifically bound materials, cells and reagents, are washed from the column. Finally, the purified multipotent stem cells are eluted from the column. The cells are viable and ready for use for therapeutic or research applications.

Example 22. Step Gradient Liquid Chromatography with Pipette Tip Cell Stationary Phase Columns An eight-channel E4 pipette (Mettler Toledo) is fitted to pipette tip column outfitted with adapters that allows them to fit into a 96-well deep well plate. The pipette is programmed with firmware and software to be about to operate with back and forth flow while freestanding in the well. The pipette is moved manually from well to well for the various operations. The 1000 mL pipette tip columns are packed with 100 μL bed volume of PS/DVB resin beads with an average diameter of 50 μm. The beads are surface reacted with streptavidin functional groups.

Cancer cell lines are used as a model for anti-cancer drug testing. A panel of cell lines derived from lung cancer is tested systematically. The panel consists of cells that grow in suspension such as COR-L26. The cells are biotin tagged for immobilization to streptavidin-derivatized beads. Terminal amines of cell surface proteins are labeled, on average of one label per cell, using NHS biotin tags available from Thermo Fisher Pierce (Cat. #20217).

An antibody or biomolecule library is screened for binding to the cell stationary phase columns. The library is injected on the column with bidirectional flow. Step gradient chromatography is used to elute the antibody or biomolecule from the cell stationary phase with increasing stringency steps. The antibody drug leads or biomolecules are selected through their stringency binding properties. Antibodies with the lowest selectivity for the column are eluted first. The strength of the eluent is increased to elute or displace tighter binding antibodies or antibodies or other molecules that have a higher selectivity for the stationary phase. The highest selectivity or the tightest binding antibodies or biomolecule are eluted last. The relative affinity of the molecules is measured and compared.

Pipette tip columns are equilibrated in 1 mL of PBS buffer using two cycles of back and forth flow. A cycle consists of aspiration of the buffer volume minus 50 μL at a flow rate of 250 μL per minute, pause of 20 seconds, dispense of the buffer volume minus 50 μL at a flow rate of 250 μL per minute, pause of 20 seconds, while maintaining the end of the pipette tip column 1 mm above the bottom on the 96-well deep-well plate.

Pipette tip columns are moved to wells containing 1 mL of biotin-labeled COR-L26 cells. The cells are immobilized to the beads using 4 cycles of capture to form the cell stationary phase column. The pipette tip columns are moved to wells containing 1 mL of PBS buffer and the resin is washed using 1 cycle.

The pipette tip columns are next moved to wells containing a 1 mL solution consisting of a commercially available antibody library. The pipette tip columns are loaded with antibody using 4 cycles of capture.

Stringency elution is performed by subjecting the pipette tip columns to a step gradient chromatography, each buffer with a lower pH. The pipette tip columns perform 4 cycles in 300 μL of PBS buffer adjusted to pH 7.2, 7.0, 6.8, 6.6, 6.4, 6.2, 6.0, 5.8, 5.6, 5.4, 5.2, and 5.0 in a step-wise manner. Each condition will be analyzed by mass spectrometry to identify antibodies released under those conditions. The eluted antibodies may be analyzed with MALDI mass spec, or they may be digested with an enzyme and analyzed with LC-MS. In another set of experiments, the elution gradient is a single step gradient after an optional wash step.

In another set of experiments, a living cell stationary phase column is subjected to a potential binding antibody or biomolecule under specified capture conditions or a specified set of capture conditions. The after capture of the antibody or biomolecule, the column is washed and the antibody or biomolecule is eluted and the amount measured. The ability to capture the antibody or biomolecule under different chemical conditions is a measure of the affinity of the antibody or biomolecule for the cell stationary phase.

Example 23. Step Gradient Liquid Chromatography with Flow Through Cell Stationary Phase Columns Experiments described in example 22 are performed with flow through cell stationary phase columns and apparatus as described in the specification.

Example 24. Sealed Chromatographic System

A column was assembled by gluing a frit on one end, packing the column and then gluing the frit on the top of the column. A 37 micron pore, 60 micron thick Nitex screen frits was attached to the end of an acrylic tube 0.750 inches long, 0.500 inch outer diameter and 0.375 inch inner diameter. The tube with frit side down was placed on a deep well plate for packing. Packing was accomplished by standing the column on a stand with hole beneath that allowed the flow of liquid out of the lower end. An aqueous slurry of agarose resin, 45-165 micron particle size, was placed into the column by pipette. The packing material was not compressed. Excess liquid drained away filling the column with resin. Additional slurry was added until the bed of the column reached the top of the column. The end frit of a Nitex screen of the same material was glued onto the column end using a methylene chloride solvent.

Silicone tape was wrapped round the column to increase the diameter. Then two 10-mL plastic syringe bodies and male luer connections were cut to the 1 mL volume mark and placed on the end of the column. The column body was wrapped with stretchable silicone tape to seal the column body.

Male luer connections were connected to the inside of clear flexible Tygon tubing 0.25 inch outer diameter with pinch valve. The tubing was connected to 1000 mL Kendall cat no 763656 adapted to be a flexible closed feed/receiving bag containers. 250 mL of DI water was added to one of the containers and sealed. At this point, no air remained in the system and the entire column and receiver/feed system was closed to the outside.

The feed bag was filled with 250 mL of DI water with the tube pinch valve pinched closed and placed on a stand. The receiving bag was placed on stand 10 inches below the feed bad. The pinch valve was opened and the fluid flowed from the feed bag through the feed bag into the receiving bag in a closed system. Flow was controlled by the relative difference in height of the two bag containers. Flow as low as a couple of μL/min was employed to as high as 20 mL/min for this particular column. Higher flow rates are possible with greater height differences, lower backpressure columns or the use of peristaltic or bag compression pumping.

After the flow through the column was completed, the relative position of the feed bag and receiving bag was reversed by simply lowering the feed bag (now the receiving bag) and raising the receiving bag (now the feed bag), reversing the flow through the column. This can process can be performed as often as necessary to provide complete capture of the cell or other process.

In another set of experiments, the flow through the column is performed with a peristaltic pump or other type of pumping device. In this apparatus, the relative positions of feed and receive reservoirs is not important.

The invention claimed is:

1. A method of making a cell-based chromatography column and performing chromatography, comprising the steps of:
    a) providing at least one column, wherein the column is comprised of a packed bed of particles, wherein the packed bed of particles has a bed volume, wherein the packed bed of particles is retained between two frits, a lower frit and an upper frit, wherein the packed bed of particles is comprised of physical channels, and wherein the particles are capable of capturing cells;
    b) providing a biological sample comprised of viable cells, wherein the biological sample has a sample volume, wherein the sample volume is larger than the bed volume;
    c) aspirating the biological sample through the column using bidirectional flow, wherein the sample is aspirated through the lower frit, into the packed bed of particles and then through the upper frit;
    d) expelling the biological sample, wherein the biological sample is expelled through the upper frit, into the packed bed of particles and then through the lower frit;
    e) repeating steps (c) and (d) multiple times, wherein the viable cells pass through the physical channels in the packed bed of particles without being trapped, wherein a portion of the viable cells are captured on the particles, whereby the viable cells captured on the column comprise the cell-based chromatography column;
    f) performing chromatography by providing a second sample, wherein the second sample is comprised of antibodies, wherein the antibodies are further comprised of a drug or drug candidate, wherein the drug or drug candidate is specific for a cell surface marker present on diseased cells; and
    g) passing the second sample through the cell-based chromatography column, wherein the second sample is passed through the chromatograph using a chromatography method selected from the group consisting of step gradient chromatography, displacement chromatography, partitioning chromatography and breakthrough curve chromatography.

2. The method of claim 1, wherein step (g) is performed using unidirectional flow.

3. The method of claim 1, wherein step (g) is performed using bidirectional flow.

4. The method of claim 1, wherein following step (g), the cells are removed from the column and analyzed.

5. The method of claim 1, wherein the particles in the packed bed are impervious to reagents.

6. The method of claim 1, wherein the method is automated.

7. A method of making a cell-based chromatography column and performing chromatography, comprising the steps of:
    a) providing at least one column, wherein the column is comprised of a bed of particles, wherein the bed of particles is retained between two frits, a lower frit and an upper frit, wherein the bed of particles is comprised of physical channels, and wherein the particles are capable of capturing cells;

b) providing a biological sample comprised of viable cells, wherein the viable cells are comprised of a surface marker;
c) aspirating the biological sample into the column through the lower frit;
d) expelling the biological sample out of the column through the lower frit;
e) repeating steps (c) and (d) multiple times, wherein the viable cells pass through the physical channels in the bed of particles without being trapped, wherein a portion of the viable cells are captured on the particles in the bed of particles, wherein the viable cells are attached to the particles via the surface marker, whereby the viable cells captured on the column comprise the cell-based chromatography column;
f) performing chromatography by providing a second sample, wherein the second sample is comprised of antibodies, wherein the antibodies are further comprised of a drug or drug candidate, wherein the drug or drug candidate is specific for a cell surface marker present on diseased cells; and
g) passing the second sample through the cell-based chromatography column, wherein the second sample is passed through the cell-based chromatography column using bidirectional flow.

8. The method of claim 7, wherein the particles impervious to reagents.

9. The method of claim 7, wherein the method is automated.

10. The method of claim 1, wherein the viable cells are cancer cells.

11. The method of claim 7, wherein the viable cells are cancer cells.

12. The method of claim 1, wherein the antibody drug or antibody drug candidate is specific for infectious disease, diabetes, heart disease, Parkinson's, Alzheimer's or liver disease.

13. The method of claim 7, wherein the antibody drug or antibody drug candidate is specific for infectious disease, diabetes, heart disease, Parkinson's, Alzheimer's or liver disease.

* * * * *